(12) United States Patent
Moyle

(10) Patent No.: US 7,001,597 B1
(45) Date of Patent: Feb. 21, 2006

(54) METHODS FOR ALTERING FERTILITY

(76) Inventor: William R. Moyle, 952 River Rd., Piscataway, NJ (US) 08854

( * ) Notice: Subject to any disclaimer, the term of this patent is extended or adjusted under 35 U.S.C. 154(b) by 0 days.

(21) Appl. No.: 08/867,587

(22) Filed: Jun. 2, 1997

Related U.S. Application Data

(62) Division of application No. 08/199,382, filed on Feb. 18, 1994, now abandoned.

(51) Int. Cl.
A61K 39/395 (2006.01)

(52) U.S. Cl. .............................. 424/130.1; 424/133.1; 424/135.1; 424/143.1; 424/145.1; 424/158.1; 424/172.1

(58) Field of Classification Search ................ 530/398, 530/387.1, 388.24, 389.2; 424/130.1, 139.1, 424/145.1, 156.1, 158.1, 133.1, 135.1, 143.1, 424/172.1
See application file for complete search history.

(56) References Cited

U.S. PATENT DOCUMENTS 5,284,778 A * 2/1994 Canfield et al. ............ 436/536
5,508,261 A * 4/1996 Moyle et al. .................. 514/8

FOREIGN PATENT DOCUMENTS

WO 9116922 * 11/1991

OTHER PUBLICATIONS

Huston, Proc. Natl. Acad. Sci. 85:5879-5883, 1988.*
Thau (1979) Fertil Steril 31(2):200.*
Thau (1980) Fertil Steril 33(3):317.*
Yamamcto (1984) Am J. Reprod Immunol 5(4):164 (abstract).*
Moyle (1987) J Biol Chem 262 (35):16920, 1987.*
Moyle et al, Journal of Biological Chemistry, 1990, vol. 265, pp. 8511-8518.*
Tortola et al, Principles of Anatomy and Physiology (text), 1984, p. 791.*
Clark, Protein Engineering of Antibody Molecules for Prophylactic and Theraputic Applications in Man, 1993, p. 1.*
Fitzgerald et al, Journal of Animal Science, 1985, vol. 60, pp. 749-754. (abstract).*
Dale et al, Human Reproduction, 1992, vol. 7, pp. 1085-1089. (abstract).*

* cited by examiner

Primary Examiner—Karen A. Canella
(74) Attorney, Agent, or Firm—Richard R. Muccino

(57) ABSTRACT

The present invention relates to methods for enhancing fertility by reducing the activities and/or levels of circulating glycoprotein hormones having lutropin (LH) activity. The molecules of the invention are antibodies or other binding agents that reduce the biological activities of LH. The present invention also relates to novel methods for devising and/or selecting antibodies to specific portions of proteins including LH and human chorionic gonadotropin (hCG) to permit their biological activities to be reduced to desired degrees. The present invention also relates to the preparation of single subunit gonadotropins and gonadotropin antagonists for use in stimulating and inhibiting fertility and for controlling ovarian hyperstimulation. In a preferred embodiment, the present invention pertains to a method for stimulating fertility in mammals by reducing the activity of glycoprotein hormones having luteinizing hormone activity in circulation and thereby stimulating the production of follicle stimulating hormone which comprises administering to the mammal a therapeutically effective amount of a binding agent that binds luteinizing hormone.

11 Claims, 19 Drawing Sheets

A: N-[Beta-Subunit or Analog]-(Heptad Repeat)$_i$-C  i>2

B: N-[Beta-Subunit or Analog]-(GXY Repeat)$_i$-C  i>6

Immunoglobulin Domain
(Long line = Heavy Chain)
(Short line = Light Chain)

Immunoglobulin Heavy Chain
(minus variable and first constant domains)

E: N-[Beta-Subunit or Analog]-(GS Repeat)$_i$-[Alpha-Subunit or Analog]-C  i>2

N-(Heptad Repeat #1)-[Alpha Subunit or Analog]-C    $i>2$
         $i$

G:

N-[Beta Subunit or Analog]-(Heptad Repeat #2)-C    $j>2$
                                         $j$

---

N-(Heptad Repeat #1)$_i$-[Alpha Subunit or Analog]

Figure 6

Coding Sequence for Single Chain Gonadotropin Analog #1 and Primers (underlined)

```
     M  E  M  F  Q  G  L  L  L  L  L  L  S  M  G  G  T  W  A  S  K  E  P  L
5'-ATGAAATCGACGGAATCAGACTCGAGCCAAGATGTTCCAGGGGCTGCTCGTGTTGCTGCTGTGAGCATGGGCGGGACATGGGCATCCAAGGAGCCGCTT-
     3'-GGTTCCTACCTCTACAAGGTCCCCGACGACGACAAACGACGACTCGTACCCGCCCTGTACCGTAGGTTCCTCGGCGAA-
     ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCCCATCAATGCCACCCTGGCTGTGGAGAAGAGGGCTGCCCCGTGTGCATCACCGTCAACACCACCATCTGCCGGCTACTGCCCCACCATGACC-
GCCGGTGCCACGGCCGGGGTAGTTACGGTGGGACCGACACCTCTTCCTCCGACGGGCACACGTAGTAGCAGTTGTGGTAGACACCGGCCGATGACGGGGTGGATCTGG-

R  V  L  Q  G  V  L  R  A  L  P  Q  V  V  C  N  Y  R  D  V  R  F  E  S  I  R  L  P  G  C  P  R  G  V  N  P  V
CGCGTGCTGCAGGGGGTCCTGCGCGGCCCTGCCTCAGGTGGTGTGCAACTACCGCGATGTGCGCTTCGAGTCATCGGCTTCCTGGCTGCCGCGGGCGTGAACCCGTG-
GCGCACGACGTCCCCCAGGACGGCCGGGACGGAGTCCACCACGTTGATGGCGCTACACGCGAAGCTCAGGTAGCGCCGAAGGACCGACGGCCGCCACTTGGGCAC-
       cctnagg(MstII)

V  S  Y  A  V  A  L  S  C  Q  C  A  L  C  R  R  S  T  T  D  C  G  G  P  K  D  H  P  L  T  C  D  D  P  R  F  Q
GTCTCCTACGCGGTGGCTCTCAGCTGTCAATGTGCACTCTGCCGCGGCAGCACCACTGACTGCGGGGGTCCAAGGACCACCCTTGACCTGTGATGACCCCGCTTCAG-
CAGAGGATGCGCCACCGACAGTCGACAGTTACACGTGAGACGGCGGCGTCGTGGTGACTGACGGCCCCCAGGGTCCTGGTGGGAACTGGACACTACTGGGGCGAAGGTC-

D  S  S  S  K  A  P  P  P  S  L  P  S  P  S  R  L  P  G  P  S  D  T  P  I  L  P  Q  G  S  G  G  S  G  G  S
GACTCTCTTCCTCAAAGGCCCCTCCCCCAGCCTTCCAAGCCATCCAGACTTCCGGGACCTCCGGGACCCGGATCTCCCCCAAGGATCCGGTAGGGATCTGGTAGC-
CTGAGAGAAGGAGTTTCCGGGGAGGGGGTCGGAAGGTTCGGATAGGTCTGGAAGGCTGAGGGCTGTGGGGCTAGGAGGGGTTCCTAGGCCATCCCTAGACCATCG-
       ggatcc(BamHI)      agc A  P  D  V  Q  D  C  P  E  C  T  L  Q  E  N  P  F  F  S  Q  P  G  A  P  I  L  Q  C  M  G  C  C  F  S  R  A  Y
GCTCCTGATGTGCAGGATTGCCCAGAATGCACGCTACAGGAGAACCCATTCTTCTCCCAGCCGGGTGCCCAATACTTCAGTGCATGGGCTGCTGCTTCTCTAGAGCATAT-
CGAGGACTACACGTCCTAACGGTCTTACGTGCGATGTCCTTTGGTAAGAAGAGGGTCGGCCACGGGTTATGAAGTCACGTACCCGACGACGAAGAGATCTCGTATA-
gct(Eco47III)

P  T  P  L  R  S  K  K  T  M  L  V  Q  K  N  V  T  S  E  S  T  C  C  V  A  K  S  Y  N  R  V  T  V  M  G  G  F
CCCACTCCACTAAGGTCCAAGAAGACGATGTTGGTCCAAAGAAGGTCACCTCAGAGTCCACTTGCTGTGTAGCTAAATCATATAACAGGGTCACAGTAATGGGGGTTTC-
GGGTGAGGTGATTCCAGGTTCTTCTGCTACAACCAGGTTTCTTGCAGTGGAGTCTCAGGTGAACGACACATCGATTTAGTATATTGTCCAGTGTCATTACCCCCAAAG-

K  V  E  N  H  T  A  C  H  C  S  T  C  Y  Y  H  K  S  *
AAAGTGGAGAACCACCACGCGTCGCCACTGCAGTACTTGTTATTATCACAAATCTTAAGGTACC-3'                    SEQ ID NO: 42
TTTCACCTCTTGGTGCTGCCGCACGGTGACGTCATGATGAACAATAATAGTGTTTAGAATTCATGCCTAGGTAGAGTTCGATTAGGCCT-5'   SEQ ID NO: 43
                      (KpnI)ggtaccggatcc(BglII)                                          SEQ ID NO: 44
```

Figure 7

Coding Sequence for Single Chain Gonadotropin Analog #2 and Primers (underlined)

```
                  M  E  M  F  Q  G  L  L  L  L  L  L  S  M  G  G  T  W  A  S  K  E  P  L
5'-ATGAAATCGACGGAATCAGACTCGAGCCAAGGATGGAGATGTTCCAGGGGCTGCTGCTGTTGCTGCTGAGCATGGGCGGACATGGGCATCCAAGGAGCCGCTT-
   3'-GGTTCCTACCTCTACAAGGTCCCCGACGACGACAACGACGACTCGTACCCGCCTGTACCCGTAGGTCCTCGGCGAA-
      ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCCCCCATCAATGCCACCCTGGCTGTGGAGAAGGAGGGCTGCCCCGTGTGCATCACCGTCAACACCACCATCTGTGCCGGCTACTGCCCCACCATGACC-
GCCGGTGCCACGGCGGGGTAGTTACGGTGGGACCGACACCCTTCCTCCGACGGGGCACACGTAGTGGCAGTTGTGGTGGTAGACACGGCCGATGACGGGGTGGATCTGG-

R  V  L  Q  G  V  L  R  A  L  P  Q  V  V  C  N  Y  R  D  V  R  F  E  S  I  R  L  P  G  C  P  R  G  V  N  P  V
CGGGTGCTGCAGGGGGTCCTGCGCGCCCTGCCCCAGGTGGTGTGCAACTACCGCGATGTGCGCTTCGAGTCCATCCGGCTTCCCTGGCTGCCCCGGGGCGTGAACCCCGTG-
GCCCACGACGTCCCCAGGACGGCGGGACGGGGACGGAGTCCACCACACGTTGATGGCGCTACACCGCGAAGCTCAGGTAGGCCGAGGACCGACGGCGGCCGCACTTGGGCAC-

V  S  Y  A  V  A  L  S  C  Q  C  A  L  C  R  R  S  T  T  D  C  G  G  P  K  D  H  P  L  T  C  D  D  P  R  G  S
GTCTCCTACGCCGTGGCTCTCAGCTGTCAGTGTGCACTCTGCCCGCCGCAGCACCACTGACTGCGGGGGTCCAAGGACCACCCTTGACCTGTGATGACCCGCGGGATCC-
CAGAGGATGCGGCACCGACAGTCGACAGTTACAGTCGAGACGGGCGGTCGTGGTGACTGACGCCCCCAGGTTCCTGGTGGGAACTGGACACTACTGGGCGCCCTAGG-
                                                                       (SstII)ccgcggggatcc(BamHI)

G  S  G  S  S  A  P  D  V  Q  D  C  P  E  C  T  L  Q  E  N  P  F  F  S  Q  P  G  A  P  I  L  Q  C  M  G  C
GGTAGCGGATCTGTAGCGCTCTGATGTGCAGGATTGCCCAGAATGCACGCTACAGGAAAACCATTCTTCTCCCAGCCGGGTGCCCAATACTTCAGTGCATGGGCTGC-
CCATCGCCTAGACCATCGCGAGACTACACGTCCTAACGGGTCTTACGTGCGATGTCCTTTTGGGTAAGAAGAGGGTCGGCCCACGGGGTTATGAAGTCACGTACCCACG-
  agcgct(Eco47III)

C  F  S  R  A  Y  P  T  P  L  R  S  K  K  T  M  L  V  Q  K  N  V  T  S  E  S  T  C  C  V  A  K  S  Y  N  R  V
TGCTTCTCTAGAGCATATCCCACTCCACTAAGGTCAAGAAGACAATGTTGGTCCAAAAGAACGTCACCTCAGAGTCCACTTGCTGTGTAGCTAAATCATATAACAGGGTC-
ACGAAGAGATCGTATAGGGTGAGGTGATTCCAGTTCTTCTGTTACAACCAGGTTTTCTTGCAGTGGAGTCTCAGGTGAACGACACATCGATTTAGTATATTGTCCCAG-

T  V  M  G  G  F  K  V  E  N  H  T  A  C  H  C  S  T  C  Y  Y  H  K  S  *
ACAGTAATGGGGGGTTTCAAAGTGGAGAACCACACGGCGTGCCACTGCAGTACTTGTTATTATCACAAATCTTAAGGTACC-3'
TGTCATTACCCCCCAAAGTTTCACCTCTTGGTGTGCCGACACGGTGACGTCATGAACGAACAATAATAGTGTTTAGAATTCCATGG-5'
                                                                ggtacc(KpnI)
```

SEQ ID NO: 45
SEQ ID NO: 46
SEQ ID NO: 47

Figure 8

Coding Sequence for Single Chain Gonadotropin Analog #3 and Primers (underlined)

```
              M  E  M  L  Q  G  L  L  L  L  L  S  M  G  G  A  W  A  S  R  E  P  L
5'-ATGAAATCGACGGAATCAGACTCAGCCAAGGAATGAGATGCTCCAGGGGCTGCTGCTGTTGCTGCTGAGCATGGGCGGGGCATGGGCATCCAAGGAGCCGCTT-
          3'-GGTTCCTTACTCTACGAGGTCCCCGACGACGACAACGACGACTCGTACCGCCCCGTACCCGTAGGTCCCTCGGCGAA-
          ctcgag(XhoI)

R  P  W  C  H  P  I  N  A  I  L  A  V  E  K  E  G  C  P  V  C  I  T  V  N  T  T  I  C  A  G  Y  C  P  T  M  M
CGGCCATGGTGCCACCCCATCAATGCCATCCTGGCTGTGGAGAAGGAGGGCTGCCCCGTGTGCATCACCGTCAACACCACCATCTGTGCCGGCTACTGCCCCACCATGATG-
GCCGGTACCACGGTGGGGATGTTACGGTAGGACACGTCTTCCTCCGACGGGGACACGTAGTGGCAGTTGTGGTAGACACGGCCGATGACGGGGGTGTACTAC-

R  V  L  Q  A  V  L  P  P  L  P  Q  V  V  C  T  Y  R  D  V  R  F  E  S  I  R  L  P  G  C  P  R  G  V  D  P  V
CGGGTGCTGCAGGCGGTCCTGCCGCCCCTGCCTCAGGTGGTGTGCACCTACCGTGATGCCGTTCAGTCGCTTGAGTCCATCCGGCTCCCTGGCTGCCGGGTGGACCCGTG-
GCCCACGACGTCCGCCAGGACGGCGGGGACGGAGTCCACCACAGTGGATGGCACTACACGGTGGAGAAGTCAGGTAGGCCGAGGGACCGACGGCCGACCTGGGCAC-
                                 cctnagg(MstII)

V  S  F  P  V  A  L  S  C  R  C  G  P  C  R  R  S  T  S  D  C  G  G  P  K  D  H  P  L  T  C  D  H  P  Q  G  S
GTCTCCTTCCCTGTGGCTCTGAGCTGTCGCTGTGACCCTGCCGCCCGAGCACCTCTGACTTGACCTGTGACCACCCCAAGGATCC-
CAGAGGAAGGGACACCGAGAGTCGACAGCGACACGAGACTCGGACGGACGCGGGCGTCGTGGAGACTGACACCGCAGGTTTCTGGTGGGAACTGACACTGGTGGGGGTTCCTAGG-
                                                                              (BamHI)ggatcc G  S  G  S  G  S  A  P  D  V  Q  D  C  P  E  C  T  L  Q  E  N  P  F  F  S  Q  P  G  A  P  I  L  Q  C  M  G  C
GGTAGCGGATCGGTAGCGCTCCTGATGTGCAGATGCCCAGAATGCCACGCTACAGGAAAACCCATTCTTCCCAGCCGGGTGCCCAATACTTCAGTCATGGGCTGC-
CCATCGCCTAGACATCGCGAGGACTACACGTCCTAACGGGTCTTACGTGCGATGTCCTTTTGGGTAAGAAGAGGTCGGCCCACGGGTTATCGAAGTCAGTCACGTACCGACG-
         agcgct(Eco47III)

C  F  S  R  A  Y  P  T  P  L  R  S  K  K  T  M  L  V  Q  K  N  V  T  S  E  S  T  C  C  V  A  K  S  Y  N  R  V
TGCTTCTCTAGAGCATATCCCACTCCACTTAAGGTCCAAGAAGACGATGTTGGTCCAAAAGAACGTCACCTCAGAGTCCACTTGTGTGTAGCTAAATCATATACAGGGTC-
ACGAAGAGATCTCGTATAGGGTGAGGTGATTCCAGGTTCTTCGTTCTTCGTTCTTGCTCAAACCAGGTTTTTCTTGCAGTGGAGTCTCAGGTGAACGACACATCGATTTAGTATATGTCCAG-

T  V  M  G  G  F  K  V  E  N  H  T  A  C  H  C  S  T  C  Y  Y  H  K  S  *
ACAGTAATGGGGGTTTCAAAGTTGAAGAACCACACGGGCGTGCCACTGCACTACTTGTTATTATCACAAATCTTAAGGTACC-3'         SEQ ID NO: 48
TGTCATTACCCCCCAAAGTTTCACCTCTTGGTGTGCCGACGGTGACGTCATGAACAATAATAGTGTTTAGAATTCCATGG-5'           SEQ ID NO: 49
                                                                 ggtacc(KpnI)                   SEQ ID NO: 50
```

Figure 9

Coding Sequence for Single Chain Gonadotropin Analog 4 and Primers (underlined)

```
             M  K  T  L  Q  F  F  F  L  F  C  C  W  K  A  I  C  C  N  S  C  E  L  T  N
5'-ATGAAATCGACGGAATCAGACTCGAGCCAAGGATGAAGACACTCCAGTTTTTCTTCCTTTTCTGTTGCTGGAAAGCAATCTGCTGCAATAGCTGTGAGCTGACCAAC-
  3'-GGTTCCTACTTCTGTGAGGTCAAAAAGAAGGAAAAGACACGACCTTTCGTTAGACGACGTTATCGACGACTCGACTGGTTG-
                                                                        ctcgag(XhoI)

I  T  I  A  I  E  K  E  E  C  R  F  C  I  S  I  N  T  T  W  C  A  G  Y  C  Y  T  R  D  L  V  Y  K  D  P  A  R
ATCACCATTGCAATAGAGAAAGAAGAATGTCGTTTCTGCATAAGCATCAACACCACTTGGTGTCGTGGCTACTGCTACACCAGGGATCTGGTGTATAAGGACCCAGCAGG-
TAGTGGTAACGTTATCTCTTTCTTCTTACAGGACAAAGACGTAGGCGTAGTTGTGGTGAACCACACGATGACGATGTGGTCCCTAGACCACATATTCCTGGGTCGGTCC-

P  K  I  Q  K  T  C  T  F  K  E  L  V  Y  E  T  V  R  V  P  G  C  A  H  H  A  D  S  L  Y  T  Y  P  V  A  T  Q
CCCAAAATCCAGAAAACATGTACCTTCAAGGAACTGGTATATGAAACAGTGAGAGTGCCCGGCTGTGCTCACCATGCACAGATTCCTTGTATACATACCCAGTGGCCACCCAG-
GGGTTTTAGGTCTTTTGTACATGGAAGTTCCTTGACCATACTTTGTCACTCTCACGGGCCGACACGAGTGGTACGTCTAAGGAACATATGTATGGGTCACCGGTGGGTC-
                                                                                              tggca(BalI)

C  H  C  G  K  C  D  S  D  S  T  D  C  T  V  R  G  L  G  P  S  Y  C  S  F  G  E  M  K  E  G  S  G  G  S  G  G
TGTCACTGTGGCAAGTGTGACAGCGACAGCACTGACTGATTGTACTGTGCGAGGCCTGGGGCCCAGCTACTGCTGCTCCTTTGGTGAAATGAAAGAAGGATCCGGTAGCGGATCTGGT-
ACAGTGACACCGTTCACACTGTCGCTGCTGACTGACTAACATGACACACGCTCCGGACCCGGGTCGATGACGAGGAAACCACTTTACTTCTTCCTAGGCCATCGCCTAGACCA-
                                                                 gggccc(ApaI)                   ggatcc(BamHI)

S  A  P  D  V  Q  D  C  P  E  C  T  L  Q  E  N  P  F  F  S  Q  P  G  A  P  I  L  Q  C  M  G  C  C  F  S  R  A
AGCGGCTCCTGATGTGCAGGATTGCCCAGATGCACGTACAGGAAAACCCATTCTTCTCCCAGCCGGGTGCCCAATACTTCAGTGCATGGGCTGCTGCTTCTCTAGAGCA-
TCGCCGAGGACTACACGTCCTAACCGGTCTTACGTGCGATGTCCTTTTGGGTAAGAAGAGGTCGGCCCACCGGGGTATGAAGTCACGTACCCGACGACGAAGAGATCTCGT-
agcgct(Eco47III)

Y  P  T  P  L  R  S  K  K  T  M  L  V  Q  K  N  V  T  S  E  S  T  C  C  V  A  K  S  Y  N  R  V  T  V  M  G  G
TATCCCACTCCACTAGGTCCAAGAAGACGATGTTGGTCCAAAAGAACGTCACCTCAGAGTCCACTTGCTGTGTAGCTAAATCATATAACAGGGTCACAGTAATGGGGGT-
ATAGGGTGAGGTGATTCCAGGTTCTTCTGCTACAACCAGGTTTTCTTGCAGTGGAGTCTCAGGTGAACGACACATCGATTTAGTATATTGTCCCAGTGTCATTACCCCA-

F  K  V  E  N  H  T  A  C  H  C  S  T  C  Y  Y  H  K  S  *                    SEQ ID NO: 51
TTCAAAGTGGAGAACCACACGGCGTGCCACTGCAGTACTTGTTATTATCACAAATCTTAAGGTACC-3'          SEQ ID NO: 52
AAGTTTCACCTCTTGGTGTGCCCACGGTGACGTCATGAACAATAATAGTGTTTAGAATTCCATGG-5'           SEQ ID NO: 53
                                                    ggtacc(KpnI)
```

Figure 10

Coding Sequence for Single Chain Gonadotropin Analog #5 and Primers (underlined)

```
          M  E  M  F  Q  G  L  L  L  L  L  L  S  M  G  G  T  W  A  S  K  E  P  L
5'-ATGAAATCGACGGAATCAGACTCGAGCCAAGGATGGAGATGTTCCAGGGCTGCTGCTGTGCTGCTGAGCATGGGCGGGACATGGGCATCCAAGGAGCCGCTT-
   3'-GGTTCCTACCTCTACAAGGTCCCCGACGACGACAACGACGACGACTCGTACCCGCCCGTACCGTAGGTTCCTCGGCGAA-
   ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCCCATCAATGCCACCCTGGCTGTGAGAAGGAGGGCTGCCCCGTGCCCATCTGTGCCGGCTACTGCCCCACCATGACC-
GCCGGTGCCACGCGGGGTAGTTACGGTGGACCGACACACCTCTTCCTCCGACGGGCACACGTAGTGGCAGTTGGTTGTGGTAGAACACGGCCGATGACGGGTGGATCTGG-

R  V  L  Q  G  V  L  R  A  L  P  Q  V  V  C  N  Y  R  D  V  R  F  E  S  I  R  L  P  G  C  P  R  G  V  N  P  V
CGCGTGCTGCAGGGGGTCCTGCCGCCCTGCCTCAGGTGGTGTGCAACTACCGGCGATGTGCGCTTCGAGTCCATCCGGCTTCCCGGCTGCCCGCGGGGTGAACCCGTG-
GCGCACGACGTCCCCAGGACGGCGCCGGACGGAGTCCACCACAGTTGATGGCGCTACACGCGAAGCTCAGGTAGGCGGACGACGGGGCGCCGCCACTTGGGCAC-
                                                                cctnagg(MstII)

V  S  Y  A  V  A  L  S  C  Q  C  A  L  C  D  S  D  S  T  D  C  T  V  R  G  L  G  P  S  Y  C  S  F  G  E  M  K
GTCTCCTACGCCGTGGCTCTCAGTTGCCAGTGTGCACTCTGCGACAGCGACAGCACTGATTGTACTGTCGAGGCCTGGGGCCAGCTACTGTCCTTTGGTGTGAAATGAAA-
CAGAGGATGCGGCACCGACAGTCGACAGTTACACGGTCAGACGCTGTCGCTGTCGTGACTAACATGACACGTCCGGACCTGCGATGACGAGGAAACCACTTTACTTT-
                                                                 gggccc(ApaI)

E  G  S  G  S  G  G  S  A  P  D  V  Q  D  C  P  E  C  T  L  Q  E  N  P  F  F  S  Q  P  G  A  P  I  L  Q  C
GAAGGATCCGGTAGCGGATCTGGTAGCGCTCCTGATGTGCAGGATTGCCCAGAATGACAGCTACAGGAGAAAACCATTCTTCTTCTCCCAGCCGGGTGCCCAATACTTCAGTGC-
CTTCCTAGGCCATCGCCTAGACCATCGCCGAGGACTACACGTCCTAACGGTCTTACGTGTCCTTTGGGTAAGAAGAGGGTCGGCCCACGGGTATGAAGTCACG-
ggatcc(BamHI)      agcgct(Eco47III)

M  G  C  C  F  S  R  A  Y  P  T  P  L  R  S  K  K  T  M  L  V  Q  K  N  V  T  S  E  S  T  C  C  V  A  K  S  Y
ATGGGCTGCTGCTTCTCTAGAGCATATCCCACTCCACTAAGGTCCAAGAAGACGATGTTGGTCCAAAAGAACGTCACCTCAGAGTCCACTTGCTGTGTAGCTAAATCATAT-
TACCCGACGACGAAGAGATCTCGTATAGGGTGAGGTGATTCCAGGTTCTTGCTACAACCAGGTTTTCTTGCAGTGGAGTCTCAGGTGAACGACACATCGATTTAGTATA-

N  R  V  T  V  M  G  G  F  K  V  E  N  H  T  A  C  H  C  S  T  C  Y  Y  H  K  S  *
AACAGGGTCACAGTAATGGGGGGTTCAAAGTGGAGAACCACACGCGTGCCACTGCCAGTACTTGTTATTATCACAAATCTTAAGGTACC-3'                    SEQ ID NO: 54
TTGTCCCAGTGTCATTACCCCCCAAGTTTCACCTCTTGGTGTGCCGCACGGTGACGTCATGAACAATAATAGTGTTTAGAATTCCATGG-5'                    SEQ ID NO: 55
                                                                  ggtacc(KpnI)                                   SEQ ID NO: 56
```

Figure 11

Coding Sequence for Single Chain Gonadotropin Analog #6 and Primers (underlined)

```
      M  E  M  F  Q  G  L  L  L  L  L  L  S  M  G  G  T  W  A  S  K  E  P  L
5'-ATGAAATCGACGACGAATCAGACTCGAGCCAAGGATGGAGATGTTCCAGGGGCTGCTGCTGTTGCTGCTGAGCATGGGCGGACATGGCACTTGACCCGTAGGTTCCTCGGCGAA-
3'-GGTTCCTACCTCTACAAGGTCCCCGACGACGACAACGACGACTCGTACCCGCTGTACCGTGAGGTTCCTCGGCGAA-
   ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCCCATCAATGCCACCCTGGCTGTGGAGAAGGAGGGCTGCCCCGTGTGCATCACCGTCAACACCACCATCTGTGCCGGCTACTGCCCCACCATGACC-
GCCGGTGCCACGGCGGGTAGTTACGGTGGACCGACACCTCTTCCCCGACGGGCACACGTAGTGGCAGTTGTGGTGTAGACACGGCCGATGACGGGGTGGATCTGG-

R  V  L  Q  G  V  L  R  A  L  P  Q  V  V  C  N  Y  R  D  V  R  F  E  S  I  R  L  P  G  C  P  R  G  V  N  P  V
CGGGTGCTGCAGGGGGTCCTGCGGGCCCTGCCCCAGGTGGTGTGCAACTACCGCGATGTGCGCTTCGAGTCCATCCGGCTCCCGGCTGCCCGGGGCGTGAACCCGTG-
GCCCACGACGTCCCCCAGGACGCCCGGGACGGGGTCCACCACACGTTGATGGCGCTACACGCGAAGCTCAGTAGGCCGAGGACCGACGGGGCCGCGCACTTGGGCAC-
                                               cctnagg(MstII)

V  S  Y  A  V  A  L  S  C  Q  C  A  L  C  R  R  S  T  T  D  C  T  V  R  G  L  G  P  S  Y  C  S  F  G  E  M  K
GTCTCTACGCGTGGCTCTCAGTGCTGTCAATGTCACTCTGCCGCCGACAACTCTGCGCCGCAGACCACTGACTGCACTGTGCGGGGCCCTGGGCGCCAGTCCTGCTCCTTTGGTGAAATGAAA-
CAGAGGATGCGCACCGACCGACAGTGTCACAGTTACACGTGAGACGCGGCGCTGTTGACACGCGTCGTGACTGACGCTCCGACACGTGACTGACGAGGAAACCACTTTACTTT-
                                                                                                    gggccc(ApaI)

E  G  S  G  G  S  G  G  S  A  P  D  V  Q  D  C  P  E  C  T  L  Q  E  N  P  F  F  S  Q  P  G  A  P  I  L  Q  C
GAAGGATCCGGTAGGCGATCTGGTAGCGCTCTGATGTGCAGGATTGCCCAGAATGCACGCTACAGGAAATGCCACGCTACAGGAAAACCCATTCTTCTCCCAGCGGGTGCCCAATACTTCAGTGC-
CTTCCTAGGCCATCGCCATCGACGAGCTAGACCATCGCGAGGACTACAGCGTCCTAACGGGTCTTACGTGCGATGTCTTTTGGGTAAGAAGAGGTCGGCCACGGGTTATGAAGTCACG-
   ggatcc(BamHI)        agcgct(Eco47III)

M  G  C  C  F  S  R  A  Y  P  T  P  L  R  S  K  K  T  M  L  V  Q  K  N  V  T  S  E  S  T  C  C  V  A  K  S  Y
ATGGGCTGCTGCTTCTCTAGAGCATATCCCACTCCACTGCGTAAGGTCAAGAAGACGATGTTGGTCCAAAAGAACGTCACCTCAGAGTCCACTTGCTGTGTGAGTCAAATCATAT-
TACCCGACGACGAAGAGATCTCGTATAGGGTGAGGTGATCCAGGTTCTTCGTACAAACCAGGTTTTCTTGCTACAACAAGGTTTCTTGCAGTGGAGTCTCAGTGAACGACACATCGATTAGTATA-

N  R  V  T  V  M  G  G  F  K  V  E  N  H  T  A  C  H  C  S  T  C  Y  Y  H  K  S  *
AACAGGGTCACAGTAATGGGGGGTTTCAAAGTGGAGAACCACACGGCGTGCCACTGCAGTACTTGTTATTATCACAAATCTTAAGGTACC-3'
TTGTCCAGTGTCATTACCCCCCAAAGTTTCACCTCTTGGTGTGCCGCACGGTGACGTCATGAACACATATAGTGTTTAGAATTCCATGG-5'
                                                                             ggtacc(KpnI)
```

SEQ ID NO: 57
SEQ ID NO: 58
SEQ ID NO: 59

Figure 12
Coding Sequence for Single Chain Gonadotropin Analog #7 and Primers (underlined)

```
            M   E   M   F   Q   G   L   L   L   L   L   L   S   M   G   G   T   W   A   S   K   E   P   L
5'-ATGAAATCGACGAATCAGACTCGAGCCAAGGATGGAGATGTTCCAAGGGGCTGCTGTTGCTGCTGCTGAGCATGGGCGGGACATGGGCATCCAAGGAGCCGCTT-
3'-GGTTCCTACCTCTACAAGGTCCCCGACGACGACAACGACGACGACGACTCGTACCCGCCCTGTACCGTAGGTTCCTCGGCGAA-
  ctcgag(XhoI)

R   P   R   C   R   P   I   N   A   T   L   A   V   E   K   E   G   C   P   V   C   I   T   V   N   T   T   I   C   A   G   Y   C   P   T   M   T
CGGCCACGGTGCCGCCCCATCAATGCCACCCTGGCTGTGGAGAAGGAGGGCTGCCCCGTGTGCATCACCGTCAACACCACCATCTGTGCCGGCTACTGCCCCACCATGACC-
GCCGGTGCCACGGCGGGGTAGTTACGGTGGGACGACACCTCTTCCTCCGACGGGCACACTAGTAGCAGTTGTGGTAGACACGGCCGATGACGGGGTGGATCTGG-

R   V   L   Q   G   V   L   R   A   L   P   Q   V   V   C   N   Y   R   D   V   R   F   E   S   I   R   L   P   G   C   P   R   G   V   N   P   V
CGCGTGCTGCAGGGGGTCCTGCGGGCCCTGCCTCAGGTGGTGTGCAACTACCGCGATGTGCGCTTCGAGTCCATCCGGCTCCTGCCCGGCTGCCCGCGGGGTGAACCCCGTG-
GCGCACGACGTCCCCAGGACGCCCGGGACGGCGGGACGGAGTCCACCACACGTTGATGGCGCTACACGCGAAGCTCAGGTAGGCCGAGGACCGAGGGGCGCGCCACTTGGGGCAC-
        cctnagg(MstII)

V   S   Y   A   V   A   L   S   C   Q   C   A   L   C   R   R   S   T   T   D   C   T   V   R   G   L   G   P   S   Y   C   S   F   G   E   G   S
GTCTCCTACGCCGTGGCTCTCCAGCTGTCAATGTGACTCTGCCGCCCGACAGCACCACTGACTGACTGCGAGGCCTGGGGCCCAGCTACTGCTCTTTGGTGAAGGATCC-
CAGAGGATGCCGCACCGACAGTTACAGTACGACAGACACTCGTGTGACTGACTGACGACGCTCCGACACCCGGGTCGATGACGAGGAAACCACTTCCTAGG-
            agcgct(Eco47III)                                              gggccc(ApaI)                ggatcc(BamHI)

G   S   G   S   G   S   A   P   D   V   Q   D   C   P   E   C   T   L   Q   E   N   P   F   F   S   Q   P   G   A   P   I   L   Q   C   M   G   C
GGTAGCGGATCTGTAGCGCTCCTGATGTGCAGGATTGCCCAGAATGCACGCTACAGGAAAACCCATTCTTCTCCCAGCCGGGTGCCCAATACTTCAGTCATGGGCTGC-
CCATCGCCTAGACCATCGCGAGGACTACAGCTCTAACGGGTCTTACGTGCGATGTCCTTTGGGTAAGAAGAGGGTCGGCCACGGGTATGAAGTCACGTACCCGACG-
  agcgct(Eco47III)

C   F   S   R   A   Y   P   T   P   L   R   S   K   K   T   M   L   V   Q   K   N   V   T   S   E   S   T   C   C   V   A   K   S   Y   N   R   V
TGCTTCTCTAGAGACATATCCCACTCCACTAAGGTCCAAGAAGACATGTTGGTCCAAAAGAACGTCACCTCAGAGTCCACTTGCTGTGTAGCTAAATCATATAACAGGGTC-
ACGAAGAGATCTCGTATAGGGTGAGGTGATTCCAGGTTCTTCTGCTACAACCAGGTTTCTTGCAGTGGAGTCTCAGGTGAACGACATCGATTAGTATTGTCCCAG-

T   V   M   G   G   F   K   V   E   N   H   T   A   C   H   C   S   T   C   Y   Y   H   K   S   *
ACAGTAATGGGGGTTTCAAAGTGGAGAACCACACCGCGTGCCACTGCAGTACTTGTTATTATCACAAATCTTAAGGTACC-3'        SEQ ID NO: 60
TGTCATTACCCCCAAAGTTTCACCTCTTGGTGTGCCGCACGGTGACGTCATGAACACAATAATAGTGTTTAGAATTCCATGG-5'       SEQ ID NO: 61
                                                                      ggtacc(KpnI)            SEQ ID NO: 62
```

Figure 13

Coding Sequence for Single Chain Gonadotropin Analog #8 and Primers (underlined)

```
         M   E   M   F   Q   G   L   L   L   L   L   L   S   M   G   G   T   W   A   S   K   E   P   L
5'-ATGAAATCGACGGAATCGAGCCAAGGATGGAGATGTTCCAGGGGCTGCTGCTGTTGCTTGCTGCTGAGCATGGGCGGACATGGGCATCCAAGGAGCCGCTT-
                                      3'-GGTTCCTACCTCTACAAGGTCCCCGACGACGACAACGACGACGACTCGTACCCGCCTGTAGGTTCCTCGGGGAA-
                                        ctcgag(XhoI)

R   P   R   C   R   P   I   N   A   T   L   A   V   E   K   E   G   C   P   V   C   I   T   V   N   T   T   I   C   A   G   Y   C   P   T   M   T
CGGCCACGGTGCCGCCTCAATGCCACCCTGGCTGTGGAGAAGGAGGGCTGCCCCGTGCACATCACCGTCAACACCACCATCTGTGCCGGCTACTGCCCCACCATGACC-
GCCGGTGCCACGGCGGAGTTACGGTGGGACCGACACCTCTTCCTCCGACGGGGCACACGTAGTTGGTGGTAGACACCGGCCGATGACGGGGTGGATCGG-

R   V   L   Q   G   V   L   R   A   L   P   Q   V   V   C   N   Y   R   D   V   R   F   E   S   I   R   L   P   G   C   P   R   G   V   N   P   V
CGCGTGCTGCAGGGGGTCCTGCGGGCCCTGCCTCAGGTGGTGTGCAACTACCGCGATGTGCGCTTCAGTCCATCCGGCTCCTGGCTGCCCGGCCGTGAACCCGTG-
GCGCACGACGTCCCCAGGACGGCCGGGACGGAGTCCACCACAACGACGTTGATGGCGCTACACGCGAAGTCAGGTAGGCCGAGGGACCGACGGGCCGCCGCACTTGGGCAC-
                        cctnagg(MstII)

V   S   Y   A   V   A   L   S   C   Q   C   A   L   C   R   R   S   T   T   D   C   T   V   R   G   L   G   P   S   Y   C   D   D   P   R   G   S
GTCTCCTACGCCGTGGCTCTCAGCTGTCAATGCCACTCTGCCGCCGCAGCACCACTGACTGCACTGTGCGAGGCCTGGGGCCCAGCTACTGCGATGACCGCGGGATCC-
CAGAGGATGCGGCACCGACAGTTACGACGTGAGACGTTACGGTGAGACGGCGGTCGTGGTGACTGACGCTGACACGCTCCGGACCCGGGTCGATGACGCTACTGGCGCCCTAGG-
                                                                                gggccc(ApaI)    (SstII)ccgcggggatcc(BamHI)

G   S   G   S   A   P   D   V   Q   D   C   P   E   C   T   L   Q   E   N   P   F   F   S   Q   P   G   A   P   I   L   Q   C   M   G   C
GGTAGCGGATCTGGTAGCGCTCCTGATGTGCAGGATTGCCCAGAATGCACGCTACAGGAGAAAACCATTCTTCTCCAGCCGGTGCCCAATACTTCAGTGCATGGGCTGC-
CCATGCCTAGACCATCGCCGAGGACTACACGGTCCTAACGGGTCTTACGTGCGATGTCCTTTTGGGTAAGAAGAGGGTCGGCCACGGGTTATGAAGTCACGTACCGACG-
    agcgct(Eco47III)

C   F   S   R   A   Y   P   T   P   L   R   S   K   K   T   M   L   V   Q   K   N   V   T   S   E   S   T   C   C   V   A   K   S   Y   N   R   V
TGCTTCTCTAGAGCATATCCCACTCCACTAAGGTCCAAGAAGACAATGTTGGTCCAAAAGAACGATGCTCACCTCAGAGTCCACTTGCTGTGTAGCTAAATCATATAACAGGGTC-
ACGAAGAGATCTCGTATAGGGTGAGGTGATTCCAGGTTCTCAGGTTCTTCTACAACCAGGTTTTCTTGCAGTGGAGTCTCAGGTGAAGTCAGGTGAACGACCATCGATTAGTATATTGTCCAG-

T   V   M   G   G   F   K   V   E   N   H   T   A   C   H   C   S   T   C   Y   Y   H   K   S   *
ACAGTAATGGGGGGTTTCAAAGTGGAGAACCACACGGCCGTGCCACTGCCACTGCACTTGTTATTATCACAAATCTTAAGGTACC-3'          SEQ ID NO: 63
TGTCATTACCCCCCAAAGTTTCACCTCTTGGTGTGCCGACGGTGACGTCATGAACAATAATAGTGTTTAGAATTCCATGG-5'              SEQ ID NO: 64
                                                                        ggtacc(KpnI)              SEQ ID NO: 65
```

Figure 14
Coding Sequence for Single Chain Gonadotropin Analog 9 and Cassette (underlined)

```
              M  K  T  L  Q  F  F  F  L  F  C  C  W  K  A  I  C  C  N  S  C  E  L  T  N
5'-ATGAAATCGACGGAATCAGACTCGAGCCAAGGATGAAGACACTCCAGTTTTTCTTCCTTTTCTGTTGCTGGAAAGCAATCTGCTGCATAGCTGTGAGCTGACCAAC-
3'-GGTTCCTACTTCTGTGAGGTCAAAAAGAAGGAAAAGACAACGACCTTTCGTTAGACGACGTTATCGACACTCGACTGGTTG-
   ctcgag(XhoI)
```

```
   I  T  I  A  I  E  K  E  E  C  R  F  C  I  S  I  N  T  T  W  C  A  G  Y  C  Y  T  R  D  L  V  Y  K  D  P  A  R
ATCACCATTGCAATAGAGAAAGAAGAATGTCGTTTCTGCATAAGCATCAACACCACTTGGTGTGCTGGCTACTGCTACACCAGGGATCTGTGTATAAGGACCCAGCAGG-
TAGTGGTAACGTTATCTCTTTCTTCTTACAGCAAAGACGTAGTTCGTAGTTGTGGTGAACCACACGACGATGTGGTCCTAGACCACATATTCCTGGGTCGGTCC-
```

```
   P  K  I  Q  K  T  C  T  F  K  E  L  V  Y  E  T  V  R  V  P  G  C  A  H  H  A  D  S  L  Y  T  Y  P  V  A  T  Q
CCCAAAATCCAGAAAACATCCAAGGAACTGGTATATGAAACAGTGAGAGTGCCCGGCTGTGCTCACCATGCAGATTCCTGTATACATACCCAGTGGCCACCCAG-
GGGTTTAGGTCTTTTGTACAGGTCTTCTTGACCATATACTTTGTCACTCTCACGGGCCGACACGAGTCGTACGTTAAGGACATATGTATGGGTCACCGGTGGGTC-
                                                                           tggcca(BalI)
```

```
   C  H  C  G  K  C  D  S  D  S  T  D  C  T  V  R  G  L  G  P  S  Y  C  S  F  G  E  G  S  G  S  G  S  S  A  P
TGTCACTGTGGCAAGTGTGACAGCGACACTGATTGTACTGTGCGAGGCCTGGGACCCCAGCTACTGCTCCTTTGGTGAAGGATCCGGTAGCGGATCTGGTAGCGCTCCT-
ACAGTGACACCGTTCACACTGTCGCTGTCGTGACTAACATGACACGCTCCGGACCCTGGGGTCGATGACGAGGAAACCACTTCCTAGGCCATCGCCTAGACCATCGCGAGGA-
               gggccc(ApaI)     (BamHI)ggatcc                              agcgct(Eco47III)
```

```
   D  V  Q  D  C  P  E  C  T  L  Q  E  N  P  F  F  S  Q  P  G  A  P  I  L  Q  C  M  G  C  C  F  S  R  A  Y  P  T
GATGTGCAGGATTGCCCAGAATGCACGCTACAGGAAAACCCATTCTTCTCCCAGCCGGGTGCCCAATACTTCAGTGCATGGGCTGCTGCTTCTCTAGAGCATATCCACT-
CTACACGTCCTAACGGTCTTACGTGCGATGTCCTTTTGGGTAAGAAGAGGGTCGGCCCACGGGTTATGAAGTCACGTACCCGACGACGAAGAGATCTCGTATAGGTGA-
```

```
   P  L  R  S  K  K  T  M  L  V  Q  K  N  V  T  S  E  S  T  C  C  V  A  K  S  Y  N  R  V  T  V  M  G  G  F  K  V
CCACTAAGGTCCAAGAAGACCATGTTGGTCCAAAAGAACGTCACCTCAGAGTCCACTTGCTGTGTAGCTAAAGGGTCACGTAATAACAGGGTCACGTAATGGGGGGTTCAAGTG-
GGTGATTCCAGGTTCTTCTGCTACAACCAGGTTTTCTTGCAGTGGAGTCTCAGGTGAGTCAGGTCTCAGGTCAACGACACATCGATTAGTATATTGTCCCAGTGTCATTACCCCCAAGTTCAC-
```

```
   E  N  H  T  A  C  H  C  S  T  C  Y  Y  H  K  S  *
GAGAACCACACGGCGTGCCACTGCAGTACTGTGTTATTATCACAAATCTTAAGGTACC-3'               SEQ ID NO: 66
CTCTTGGTGTGCCGACACGGTGACGTCATGAACAATAATAGTGTTTAGAATTCCATGG-5'              SEQ ID NO: 67
                                                ggtacc(KpnI)                 SEQ ID NO: 68
```

Figure 15

Coding Sequence for Single Chain Gonadotropin Analog 10 and Cassette (underlined)

```
            M  K  T  L  Q  F  F  F  L  F  C  C  W  K  A  I  C  C  N  S  C  E  L  T  N
5'-ATGAAATCGACGGAATCAGACTCGAGCCAAGGATGAAGACACTCCAGTTTTTCTCCTTTCTTTGTGTTGCTGGAAAGCAATCTGCTGCAATAGCTGTGAGCTGACCAAC-
    3'-GGTTCCTACTTCTGTGAGGTCAAAAAGAAGAAAGAGAAAGACAACAACCTTTCGTTAGACGACGTTATCGACACTGACTGGTTG-
       ctcgag(XhoI)

I  T  I  A  I  E  K  E  E  C  R  F  C  I  S  I  N  T  T  W  C  A  G  Y  C  Y  T  R  D  L  V  Y  K  D  P  A  R
ATCACCATTGCAATAGAGAAGAAGAATGTCGTTTCTGCATAAGCATCAACACCACTTGGTGTGCTACTGCTACACCAGGATCTGGTGTATAAGGACCCAGCCAGG-
TAGTGGTAACGTTATCTCTTCTTCTTACAGCAAAGACGTAGGCTAGTTGTGGTGAACCACGACGATGACGATGACGATGGTCCCTAGACCACATATTCCTGGTCGGTCC-

P  K  I  Q  K  T  C  T  F  K  E  L  V  Y  E  T  V  R  V  P  G  C  A  H  H  A  D  S  L  Y  T  Y  P  V  A  T  Q
CCCAAAATCCAGAAAACATGTACCTTCAAGGAACTGGTATATGAAACAGTGAGAGTGCCCGGCTGTGCTCACCATGCAGATTCCTTGTATACATACCCAGTGGCCACCCAG-
GGGTTTTAGGTCTTTTGTACATGGAAGTTCCTTGACCATATCACTTTGTCACTCTCGACACGAGTGTACGTCTAAGGAACATATGTATGGTCACCGGTGGTC-
                                                                                tggcca(BalI)

C  H  C  G  K  C  D  S  D  S  T  D  C  T  V  R  G  L  G  P  S  Y  C  G  S  G  S  G  S  A  P  D  V  Q  D
TGTCACTGTGGCAAGTGTGACAGCGACAGCACTGATTGTACTGTGCGAGGCCTGGGGCCCAGCTACTCCGGATCCGGTAGCGGATCTGGTAGCGCTCCTGATGTGCAGGAT-
ACAGTGACACCGTTCACACGTCGCTGTCGCTGACTAACATGACACGTCCGACTGATGACGCCTAGGCCATCGCCTAGACCATCGCGAGGACTACACGTCCTA-
                                                          gggccc(ApaI)        (BamHI)ggatcc    agcgct(Eco47III)

C  P  E  C  T  L  Q  E  N  P  F  F  S  Q  P  G  A  P  I  L  Q  C  M  G  C  C  F  S  R  A  Y  P  T  P  L  R  S
TGCCCAGAATGCACGCTACAGGAAAACCCATTCTTCTCCCAGCCGGGTGCCCAATACTTCAGTGCATGGCTGCTGCTTCTCTAGAGCATATCCCACTCCACTAAGGTCC-
ACGGGTCTTACGTGCGATGTCCTTTTGGGTAAGAAGAGGGTCGGCCACGGGGTTATGAAGTCACGTACCGACGACGAAGAGATCTCGTATAGGGTGAGGTGATTCCAGG-

K  K  T  M  L  V  Q  K  N  V  T  S  E  S  T  C  C  V  A  K  S  Y  N  R  V  T  V  M  G  G  F  K  V  E  N  H  T
AAGAAGACGATGTTGGTCCAAAAGAACGTCACCTCAGAGTCCACTTGCTGTGTAGCTAAATCATATAACAGGGTCACAGTAATGGGGGGTTTCAAAGTGGAGAACCACACG-
TTCTTCTGCTACAACCAGGTTTTCTTGCAGTGGAGTCCAGGTGAACGACATCGATTAGTATATTGTCCCAGTGTCATTACCCCCAAAGTTTCACCTCTTGGTGTGC-

A  C  H  C  S  T  C  Y  Y  H  K  S  *
GCGTGCCACTGCAGTACTGTTATTATCACAAATCTTAAGGTACC-3'              SEQ ID NO: 69
CGCACGGTGACGTCATGACAATAATAGTGTTTAGAATTCCATGG-5'              SEQ ID NO: 70
                                  ggtacc(KpnI)              SEQ ID NO: 71
```

Figure 16

Preparation of an alpha-subunit coding region lacking oligosaccharide signal sequences

```
  C  G  S  G  S  G  S  A  P  D  V  Q  D  C  P  E  C  T  L  Q  E  N  P  F  F  S  Q  P  G  A  P  I  L  Q  C
TGCGGATCCGGTAGCGGATCTGGTAGCGGCTCCTGATGTGCAGGATTGCCCAGAATGCACGCTACAGGAAAACCCATTCTTCTCCCAGCCGGGTGCCCAATACTTCAGTGC-
ACGCCTAGGCCATCGCCTAGACCATCGCCGAGGACTACACGTCCTAACGGGTCTTACGTGCGATGTCCTTTGGGTAAGAAGAGGGTCGGCCCACGGGGTTATGAAGTCACG-
     (BamHI)ggatcc     agcgct(Eco47III)
```

```
 M  G  C  C  F  S  R  A  Y  P  T  P  L  R  S  K  K  T  M  L  V  Q  K  Q  V  T  S  E  S  T  C  C  V  A  K  S  Y
ATGGGCTGCTGCTTCTCTAGAGCATATCCCACTCCACTAAGGTCCAAGAAGACGATGTTGGTCCAAAAGCAAGTCACCTCAGAGTCCACTTGCTGTGTAGCTAAATCATAT-
TACCCGACGACGAAGAGATCTCGTATAGGGTGAGGTGATTCCAGGTTCTTCTGCTACAACCAGGTTTTCGTCAGTGGAGTCTCAGTGAACGACACATCGATTTAGTATA-
     tctaga(XbaI)
```

```
 N  R  V  T  V  M  G  G  F  K  V  E  Q  H  T  A  C  H  C  S  T  C  Y  Y  H  K  S  *                          SEQ ID NO: 72
AACAGGGTCACAGTAATGGGGGGTTTCAAAGTGGAGCAACACACGGCCGTGCCACTGCAGTACTTGTTATTATCACAAATCTTAAGGTACC-3'                SEQ ID NO: 73
TTGTCCCAGTGTCATTACCCCCCCAAAGTTTCACCTCGTTGTGTGCCGCACGGTGACGTCATGAACAATAATAGTGTTTAGAATTCCATGGCCATG-5'           SEQ ID NO: 74
                                                                                        ggtacc(KpnI)
```

Figure 17

Preparation of a beta-subunit coding region lacking asn-linked oligosaccaride signal sequences

```
               M  E  M  F  Q  G  L  L  L  L  L  L  L  S  M  G  G  T  W  A  S  K  E  P  L
5'-ATGAAATCGACGGAATCAGACTCGAGCCAAGGATGGAGATGTTCCAGGGGCTGCTGTTGCTGCTGCTGAGCATGGGCGGACATGGGCATCCAAGGAGCCGCTT-
3'-GGTTCCTACCTCTACAAGGTCCCCGACGACGACAACGACGACGACTCGTACCCGCCCTGTACCGTAGGTTCCTCGGGAA-
   ctcgag(XhoI)

R  P  R  C  R  P  I  Q  A  T  L  A  V  E  K  E  G  C  P  V  C  I  T  V  N  T  T  I  C  A  G  Y  C  P  T  M  T
CGGCCACGGTGCCGCCCCATCCAAGCCACCCTGGCTGTGGAGAAGGAGGGCTGCCCCGTGCATCACCGTCAACACCACCATCTGTGCCGGCTACTGCCCACCATGACC-
GCCGGTGCCACGGCGGGGGTAGGTTCGGTTCGGTGGACCGACACCTCTTCCTCCGACGGGCACACGTAGTAGCAGTTGTGGTAGACACGGCCGATGACGGGGTGGATCTGG-

R  V  L  Q  G  V  L  R  A  L  P  Q  V  V  C  N  Y  R  D  V  R  F  E  S  I  R  L  P  G  C  P  R  G  V  N  P  V
CGGTGCTGCAGGGGTCCTGCGGGCCTGCCTCAGGTGGTGCAACTACCGCGATGTGCGGTTCGAGTCCATCCGGCTCCCGGCTGCCCGGGGCGTGAACCCGGTG-
GCCACGACGTCCCCAGGACGGCCGGACGAGTCCACCACGTTGATGGCGCTACACGCGAAGCTCAGGTAGGCCGGACGACGGCCGCCGACTTGGGGAC-
               cctnagg(MstII)

V  S  Y  A  V  A  L  S  C  Q  C  A  L  C  R  R  S  T  T  D  C  G  G  P  K  D  H  P  L  T  C  D  D  P  R  F  Q
GTCTCTACGCCGTGGCTCTCAGCTGTCAATGTCACTGTGCCCGCCGCAGCACCACTGACTGCGGGGTCCCAAGGACCACCCCTTGACCTGTGATGACCCCGCTTCCAG-
CAGAGGATGCGGCACCGACAGTCGACAGTTACACGTGAGACGCCGGCGTCGTGGTGACTGACGCCCCCAGGGTTCCTGGTGGGAACTGGACACTACTGGGGCGAAGGTC-

D  S  S  S  K  A  P  P  P  S  L  P  S  P  S  R  L  P  G  P  S  D  T  P  I  L  P  Q  G  S  G  S  G  S  G  S
GACTCCTCTTCCTCAAAGGCCCCTCCCCCCAGCCTTCCAAGCCCAATCCGAGTCCCGGGCCCTCGGACACCCCGATCCTCCCCAAGGATCCGGTAGGGATCGGTAGC-
CTGAGGAGAAGGAGTTTCCGGGGAGGGGTCGGAAGGTTCGGGTAGGGCTGAGGGCCTGAGGCCTAGGAGGCTAGGAGGGGGTTCCTAGGCCATCGCCTAGGACCATCG-
                                                                                    gggccc(ApaI)              ggatcc(BamHI)     agc A  P  D  V  Q  D  C  P
GCTCCTGATGTGCAGGATTGCCCA
CGAGGACTACACGTCCTAACGGGT
gct(Eco47III)
```

APDVQDCP    SEQ ID NO: 75
            SEQ ID NO: 76
            SEQ ID NO: 77

Figure 18

Coding Sequence for Single Chain Gonadotropin Analog #1a

```
          M   E   M   F   Q   G   L   L   L   L   L   L   S   M   G   G   T   W   A   S   K   E   P   L
5'-ATGAAATCGACGGAATCAGACTCGAGCCAAGGATGTTCCAGGGGCTGCTGTTGCTGCTGCTGAGCATGGGCGGACATGGGCATCCAAGGAGCCGCTT-
3'-GGTTCCTACCTCTACAAGGTCCCCGACGACGACAACGACGAGACTCGTACCCGCCTGTACCCGTAGGTTCCTCGGCGAA-
   ctcgag(XhoI)

R   P   R   C   R   P   I   N   A   T   L   A   V   E   K   E   G   C   P   V   C   I   T   V   N   T   T   I   C   A   G   Y   C   P   T   M   T
   CGGCCACGGTGCCGCGCCCATCAATGCCACCCTGGCTGTGGAGAAGGAGGGCTGCCCGTGTCATCACCGTCAACACCACCATCTGTGCCGGCTACTGCCCCACCATGACC
   GCCGGTGCCACGGCGGGGTAGTTACGGTGGGACCGACACCTCTTCCTCCCGACGGGCACACGTAGTGGCAGTTGTGGTGGTAGACACGGCCGATGACGGGGTGGATCTGG

R   V   L   Q   G   V   L   R   A   L   P   Q   V   V   C   N   Y   R   D   V   R   F   E   S   I   R   L   P   G   C   P   R   G   V   N   P   V
   CGGTGCTGCAGGGGTCCTGCGCCCTGCCTCAGGTGGTGTGCAACTACCGCAGTCGACGATGCGGTTCGAGTCCATCCGGCTGCCTGCCGGCGTGAACCCGTG
   GCCACGACGTCCCCAGGACGCGGACGGAGTCCACCACACGTTGATGGCGCTAGCTGCCTACACGCCAAGCTCAGTAGGCTCAGTAGGCCGAGGACCGACGGCCGCCCACTTGGGCAC
   cctnagg(MstII)

V   S   Y   A   V   A   L   S   C   Q   C   A   L   C   R   R   S   T   T   D   C   G   G   P   K   D   H   P   L   T   C   D   D   P   R   F   Q
   GTCTCCTACGCCGTGGCTCTCAGTGTCTGCACTCTGCCGCCGCAGCACTGACTGCGAGGGGTCCCAAGGACCACCCCTTGACCTGTGATGACCCCGCTTCCAG
   CAGAGGATGCGGCACCGACAGTCGACAGTTACACCGTGAGACGGCGGTCGTCGTGACTGACTGACGCGCTCCCAGGGTTCCTGGTGGGAACTGGACACTACTGGGGCGAAGTC

D   S   S   S   K   A   P   P   P   S   L   P   S   P   S   R   L   P   G   P   S   D   T   P   I   L   P   Q   G   S   G   S   G   S
   GACTCCTCTTCCTCAAAGGCCCCTCCCCCAGCCTTCCAAGCCATCCGAGCCTCGACTCCGGGCCCTCGACCACCCCGATCCTCCCCAAGGATCCGGTAGCGGATCGGTAGC-
   CTGAGGAGAAGGAGTTTCCGGGGAGGGGGTCGGAAGGTTCGGAATCTCGGCGGGCCGAGGGCCCGGGACCTGTGGGCTAGGAGGGGTTCCTAGGCATCGCTAGACCATCG
                                                                 gggccc(ApaI)              ggatcc(BamHI)              agc A   P   D   V   Q   D   C   P   E   C   T   L   Q   E   N   P   F   F   S   Q   P   G   A   P   I   L   Q   C   M   G   C   C   F   S   R   A   Y
   GCTCCTGATGTGCAGGATTGCCCAGAATGCACGCTACAGGAAAAACCATTCTTCTCCAGCCGGGTGCCCAATACTTCAGTGCATGGCTGCTGCTTCTCTAGAGCATAT
   CGAGGACTACACGTCCTAACGGGTCTTACGTGCCATGTCCTTTTGGGTAAGAAGAGGTCGGCCACGGGGGTTATGAAGTACGTACCCGACGACGAAGAGATCTCGTATA-
   gct(Eco47III)

P   T   P   L   R   S   K   K   T   M   L   V   Q   K   Q   V   T   S   E   S   T   C   C   V   A   K   S   Y   N   R   V   T   V   M   G   G   F
   CCCACTCCACTAAGGTCCAAGAAGACGATGTTGGTCCAAAAGCAAGTCACCTCAGAGTCCACTTGTGTGTAGCTAAATCATATAACGAGGGTCACGTAATGGGGGTTTC-
   GGGTGAGGTGATTTCCAGGTTCTTCTGCTACAACCAGGTTTCGTTCAGTGGAGTCTCAGGTGAACGACACACTGATTTAGTATTGTCCCAGTGTCATTACCCCCAAAG-

K   V   E   Q   H   T   A   C   H   C   S   T   C   Y   Y   H   K   S   *
   AAAGTGGAGCAACACACGGCGTGCCACTGCAGTACTTGTTATTATCACAAATCTTAAGGTACC-3'                                  SEQ ID NO: 78
   TTTCACCTCGTTGTGTGCCGACACGGTGACGGTCATGAACAATAATAGTGTTTAGAATTCCATGGCCTAGGAGAGTTCGATTAGGCCT-5'         SEQ ID NO: 79
                                        (KpnI)ggtaccggatcc(BglII)                                     SEQ ID NO: 80
```

METHODS FOR ALTERING FERTILITY

This is a divisional application of patent application Ser. No. 08/199,382, filed Feb. 18, 1994 now abandoned.

BACKGROUND OF THE INVENTION

1. Field of the Invention

The present invention relates to methods for enhancing fertility by reducing the activities and/or levels of circulating glycoprotein hormones having lutropin (LH) activity. The molecules of the invention are antibodies or other binding agents that reduce the biological activities of LH. The present invention also relates to novel methods for devising and/or selecting antibodies to specific portions of proteins including LH and human chorionic gonadotropin (hCG) to permit their biological activities to be reduced to desired degrees. The present invention further relates to novel glycoprotein hormone agonists and antagonists that reduce the activities of hormones with LH activities and/or increase the activities of hormones with follitropin activity.

2. Description of the Background

The disclosures referred to herein to illustrate the background of the invention and to provide additional detail with respect to its practice are incorporated herein by reference and, for convenience, are numerically referenced in the following text and respectively grouped in the appended bibliography.

The glycoprotein hormone family (1) consists of three $\alpha,\beta$ heterodimeric glycoproteins found in the anterior pituitary gland where they are made. The glycoprotein hormones are luteinizing hormone (also known as lutropin or LH), follicle stimulating hormone (follitropin or FSH), and thyroid stimulating hormone (also known as thyrotropin or TSH). The hormones from humans are known as hLH, hFSH, and hTSH, respectively. In some species, a glycoprotein hormone structurally similar to LH called chorionic gonadotropin or CG, is made by the placenta and released into the circulation. In humans, this glycoprotein hormone is termed hCG. In primates, significant quantities of all the hormones are also found as excretion products in urine. After menopause, when the secretion of LH and FSH from the anterior pituitary is greatly increased, significant quantities of LH and FSH are found in the urine. Gonadotropin extracts of urine from menopausal women are termed human menopausal gonadotropins (hMG). Unlike hCG, which interacts like LH with LH receptors but only weakly with FSH receptors, hMG interacts with both LH and FSH receptors. The dual activity of hMG is due to the presence of hLH, hFSH, and their metabolites in the urinary extract. Urines from pregnant and menopausal women are major sources of gonadotropin activities and have important commercial uses.

Gonadotropins such as FSH, LH, and, in some species, CG play a major role in the reproductive process (1–6), while the structurally related hormone, TSH, is important for thyroid function (1). Both LH and FSH are essential for puberty and normal reproductive function. Lack of sufficient FSH, LH, or hCG at appropriate times results in infertility or termination of pregnancy. Excessive amounts of these hormones can result in premature puberty or hyperstimulation of the gonads. In the male, FSH is essential for the onset and maintenance of spermatogenesis (7,8). Immunoneutralization of FSH leads to a diminution in spermatogenesis and a loss in fertility. In the female, FSH is essential for follicular development leading to the production of the female gamete at ovulation. Polycystic ovarian disease is a common cause of infertility in women and is a condition characterized by incomplete follicular development. Fertility can usually be restored by administration of FSH or hMG. Fertility can also often be restored by treatments with antiestrogens, compounds that inhibit the negative feedback effect of estrogens on FSH secretion thereby allowing FSH levels to rise. In males, LH is required for puberty and, in its absence, there is a failure to acquire the sexual attributes and fertility of an adult. LH is primarily responsible for the synthesis of androgens in the testis. These steroids have a beneficial influence on spermatogenesis and abnormally high levels of androgens can maintain spermatogenesis once it has been initiated (9). In females, LH is essential for ovulation and formation of the corpus luteum. LH also has a synergistic influence with FSH on follicle development (4) and is well-known to promote the synthesis of follicular androgens. These androgens serve as precursors for FSH-stimulated estrogen formation. LH may also augment the effect of FSH on granulosa cells, particularly in the later stages of follicle maturation when the granulosa cells have acquired LH receptors. hCG made by the trophoblast is important for maintenance of progesterone secretion from the corpus luteum during early human pregnancy. The clinical activities of these hormones and their uses are reviewed extensively in several standard textbooks including that by Yen and Jaffe (2).

The differences in the effects of FSH and LH and the complex endocrine interactions between the two hormones cause them to have synergistic actions on follicular development and estradiol synthesis (4). For example, normal ovarian estrogen production is due to the effect of LH on androgen formation and the influence of FSH on the conversion of androgens to estradiol. In turn, estradiol can suppress FSH secretion from the pituitary gland. During the normal menstrual cycle, FSH levels decline as the follicle enlarges and secretes increasing amounts of estradiol. When estradiol levels reach a sufficient amount during the follicular phase, they can trigger an increase in LH secretion from the pituitary gland that causes ovulation. The ratio of LH/FSH activity as well as the absolute hormone levels in blood are important for reproductive functions such as follicle maturation and ovulation of the proper number of oocytes during the menstrual and estrus cycles.

While the secretion of both LH and FSH can be inhibited by steroid hormones, the secretion of FSH is usually more sensitive than that of LH to negative feedback regulation by estrogens. Indeed, in many species, high levels of estrogens can increase the secretion of LH, particularly if progesterone levels are low. Administration of anti-estrogens, compounds that disrupt the normal negative feedback regulation of estradiol on FSH secretion, often leads to increased FSH release and increased gamete production. Clinically, anti-estrogens are widely used to increase the probability of ovulation in women having polycystic ovarian disease. Unfortunately, since the negative effects of estradiol on FSH secretion are partly responsible for controlling the number of follicles that develop to the point of ovulation, disruption of the normal estrogen-FSH negative feedback loop can result in inappropriate numbers of ova being shed. A mechanism that results in increased FSH secretion without eliminating the negative feedback control of FSH secretion would have a valuable use in increasing fertility.

Purified FSH is capable of stimulating follicle development in women, particularly when some endogenous LH is also present. The ratio of FSH/LH is highest at the time of the menstrual cycle when follicular development is initiated. However, both hormones are essential for fertility. Immunoneutralization of LH leads to infertility in males and females. (10–12). Likewise immunoneutralization of CG, a hormone which acts via LH receptors was shown to block fertility in primates (13–16). Antibodies to LH have not been shown previously to stimulate fertility.

Monoclonal antibodies to hCG (termed hCG-mAb) have been shown to inhibit the binding of hCG to its receptor in vitro (17). Depending on the location of their epitopes, hCG-mAbs have differing abilities to inhibit binding of hCG to LH receptors. B105 and B110 are examples of monoclonal antibodies that recognize epitopes on hCG and LH that remain exposed when the hormones bind to LH receptors (17). Complexes of the hormones with these monoclonal antibodies bind to LH receptors, albeit with lower affinity than the free hormones. Consequently, these antibodies inhibit binding of the hormones to LH receptors. However, the maximal degree of inhibition observed in the presence of excess antibody is less than 100% and lower than that of antibodies which form complexes with the hormones that do not bind to LH receptors. In the presence of sufficient B105 or B110, the amount of hormone needed to induce a biological response is increased. Thus, even a massive excess of either antibody sufficient to bind virtually all the free hCG or LH in the assay is incapable of preventing a response to either hormone when the concentrations of the hormone-antibody complexes exceed a threshold level.

As discussed earlier, immunoneutralization of LH was shown several years ago to prevent fertility. This phenomena occurs because the antisera that were used in these studies neutralized the biological activity of LH. However, when appropriate antisera or antibodies like B105 or B110 are used, the biological activity of LH is not eliminated. Rather it is reduced by a predetermined amount. When this happens, androgen synthesis is reduced. Since androgens are precursors of estrogens, estrogen synthesis is also reduced. The decline in estradiol has a larger impact on FSH secretion than on LH secretion. The secretion of FSH will be enhanced and this will lead to an increased ratio of FSH/LH and enhanced follicular development. In females, this ratio of FSH/LH will lead to increased follicle development. In males, this ratio of FSH/LH will lead to increased Sertoli cell function and increased spermatogenesis.

An approach to increasing fertility that is based on reducing LH levels has not been used previously. In part, this is due to the many reports that antibodies to LH inhibit fertility and because methods for making and selecting antibodies that reduce but do not neutralize LH activity were previously unknown. Thus, one would not expect that this approach to fertility would be successful. As will be discussed later, this approach to increasing fertility has several advantages relative to current techniques, principly in women who make and release LH and FSH from their pituitary glands. Since reducing LH levels does not disrupt the normal endocrine feedback relationships between estradiol and FSH on pituitary function, it has a much less likely chance to induce ovarian hyperstimulation than existing techniques. This means that there will be less need for expensive and demanding patient monitoring. In addition, only one or at most a few treatments will be required to induce fertility.

Another novel method for increasing fertility is to employ an LH antagonist during the follicular phase of the menstrual cycle. For several years it is known that the oligosaccharide chains on the glycoprotein hormones are essential for their abilities to elicit signal transduction (1). Glycoprotein hormones lacking carbohydrate residues have impaired abilities to elicit a biological response. These analogs can be used to block binding of LH to its receptors. This will reduce the activity of circulating LH and thereby improve fertility. Deglycosylated gonadotropins have been found to have short biological half-lives and were found not to be useful for their original intended use, namely to inhibit fertility by reducing luteal progesterone synthesis and causing abortion. By moving the carbohydrate residues to alternate portions of the hormone by removing glycosylation signals (i.e., the amino acid sequences Asparagine-X-Threonine or Asparagine-X-Serine, where X is any amino acid except Proline) from one site and by creating glycosylation signals at alternate sites of the α- and β-subunits, it is possible to design analogs with reduced agonist activity that have sufficiently long half-lives to be useful. In addition, by preparing single chain gonadotropins in which the α- and β-subunits are covalently linked, it is possible to increase the stability of the hormones in circulation. This is because the receptor binding activities and the plasma half-lives of the heterodimeric gonadotropins are greater than either of the subunits. Covalent linkage prevents the dissociation of the two subunits in circulation.

While stimulation of fertility is important to restore fertility to infertile couples, inhibition of fertility is often desirable as a method of family planning. In addition, inhibition of fertility would be useful in the commercial production of livestock since it would eliminate the need for castration or it would prevent the development of heat in cattle held in the feedlot. Inhibition of fertility in other animals including dogs and cats would also be desirable as a replacement for spaying or castrating them. Inhibition of fertility in horses would also be preferable to gelding, particularly if it can be reversed. As noted above, fertility can be inhibited by administration of neutralizing antibodies to LH or FSH. It can also be inhibited by using a vaccine to induce the formation of these antibodies. Due to the action of hCG in maintaining pregnancy, treatments that lead to diminished hCG secretion or activity would also be expected to cause infertility. In women, it would be more desirable to inhibit fertility by inhibiting hCG rather than hLH or hFSH. This is because treatments that neutralized hLH or hFSH would cause cessation of ovarian function and hasten the onset of problems associated with menopause. In cattle and other domestic animals, it would be more important to inhibit LH to prevent puberty or to disrupt heat. As noted earlier, appropriate antibodies to chorionic gonadotropin are able to inhibit fertility in primates and women and the development of antibodies to hCG has been recognized to be an important potential method of contraception for many years (18). Since hCG is produced by a large number of human cancers and since antibodies to hCG can disrupt these tumors, immunization would also have a beneficial impact on cancer therapy or prevention (19).

Several attempts have been made to devise such an hCG-based contraceptive vaccine taking into account the differences between hCG and the other glycoprotein hormones (14,18). Unfortunately, development of the vaccine has been hampered by the structural homologies between all the glycoprotein hormones. The preferred immunogen must be highly antigenic yet not induce; antibodies that crossreact with the other glycoproteins such as human FSH, LH, or TSH. Based on the knowledge of glycoprotein hormone activities outlined above, a vaccine that induced antibodies that interacted with LH, FSH, or TSH would also cause infertility and/or inhibition of thyroid function. Unfortunately, neutralization of LH or FSH would also result in cessation of normal menstrual cycles and the loss of estrogen production that is associated with fertility in women.

Termination of ovarian function would be likely to result in premature development of osteoporosis and other problems associated with menopause. Inhibition of thyroid function would lead to hypothyroidism. Similarities in the structures of hCG and hLH have made it particularly difficult to design an appropriate immunogen that does not generate crossreacting antibodies. Most efforts have been devoted to making antibodies against the unique C-terminus of the hCG β-subunit since this portion of the molecule is not found in hLH (1). However, this region is not very antigenic. Efforts to devise immunogens have also employed peptides obtained from the β-subunit (14), conjugates of the β-subunit with other proteins (20), or heterodimers containing hCG β-subunits conjugates, and ovine α-subunits (18). Unfortunately, most of these immunogens are not very effective and a better immunogen is needed to make this method practical.

The difficulty of devising a vaccine based on hCG can be appreciated by an understanding of the structures of the glycoprotein hormones. All of the glycoprotein hormones contain a common α-subunit. While the conformation of parts of the α-subunit differ in all the hormones and can be recognized by selected monoclonal antibodies (21), portions of the α-subunit have the same conformation in each glycoprotein hormone. Thus, many antibodies to the α-subunit recognize LH, FSH, hCG, and TSH. Since anti-α-subunit antibodies are often capable of blocking the activities of the hormones (22), an immunogen which induced a response to the α-subunit is likely to have unwanted side effects. Therefore, most strategies for devising a contraceptive vaccine are directed at the hormone specific β-subunit of hCG.

The β-subunit of hCG is most closely related to the β-subunit of hLH. Many antibodies directed against the intact hCG β-subunit will also combine with the LH β-subunit. While the β-subunits of the other hormones differ considerably from that of hCG, some of the residues in all the β-subunits are identical and there is the possibility, albeit small, that some anti-β-subunit antibodies will crossreact with these hormones as well. The carboxy terminal 31 amino acids of the hCG β-subunit (CTP) are unrelated to any of the residues in the other glycoprotein hormones. In theory, antibodies to this region cannot elicit any crossreaction with the other hormones. As expected, when this region is used as an immunogen, antibodies are developed that do not crossreact with any of the other glycoprotein hormones. Unfortunately, the antibodies that are produced to synthetic CTP peptides do not bind with high affinity to hCG. In part, this is due to the observation that this region of hCG contains four potential serine-linked glycosylation sites and is highly glycosylated. Furthermore, much of this region of hCG is not essential for interaction with LH receptors. Thus, the antibodies directed against the CTP of hCG bind to hCG receptor complexes and are primarily of the nonneutralizing type. Consequently, they do not inhibit hCG action similar to antibodies like B101 (22) that prevent hCG from binding to LH receptors.

Efforts have also been made to devise antibodies against other portions of the hCG β-subunit. One region that has been investigated extensively is that found between cysteine residues 38 and 57. This portion of the protein is known to form a large loop and studies have shown that this loop is capable of stimulating steroidogenesis (23,24). Thus, one would anticipate that antibodies against this loop would be of the neutralizing type. Indeed, B101, an antibody which has been shown to recognize residues within this loop (22,25,26) is capable of neutralizing hCG activity. The problem with using this loop structure is that the antibodies that are produced are often of low affinity. In addition, since hCG and hLH are similar in this region of the molecule (i.e., there are only three amino acids that differ), immunization with this loop is expected to cause the production of antibodies against hLH. Indeed, B101, an antibody that binds to this region of the molecule has an unacceptably high affinity for hLH.

Recent efforts at identifying the tertiary structure of the glycoprotein hormones have depended on characterizing the binding sites of panels of monoclonal antibodies (26). Antibodies have been identified that prevent the biological activity of hCG or that only partially neutralize its biological activity. As outlined in example 7 of the present specification, these and similar antibodies can be used to devise immunogens that have the potential to neutralize hCG but not hLH using the positive and a negative selection procedure outlined in examples 6 and 7 set out below. While the hormone has been crystallized and a crystal structure would be valuable in determining the types of immunogens that would give a high titer immune response to particular parts of the molecule, difficulties in solving the crystal structure have precluded this approach. Thus, at the present state of the knowledge of hCG structure, there is no good method that could be used to predict the type of immunogen that would be most effective.

Another useful method for increasing fertility is to increase the levels of FSH activity. One way of accomplishing this is to administer small doses of long-acting follitropins. These can be made by coupling molecules with follitropin activity to molecules with long plasma half-lives (i.e., immunoglobulins) or by preparing single-chain gonadotropin analogs having follitropin activity (Tables 1 and 2). Alone, or in combination with antibodies to LH and/or LH antagonists, these hormones facilitate follicle development in women with polycystic ovarian disease.

BRIEF DESCRIPTION OF THE FIGURES

FIG. 6 illustrates the coding sequence for single chain gonadotropin analog #1 and primers (underlined).

FIG. 7 illustrates the coding sequence for single chain gonadotropin analog #2 and primers (underlined).

FIG. 8 illustrates the coding sequence for single chain gonadotropin analog #3 and primers (underlined).

FIG. 9 illustrates the coding sequence for single chain gonadotropin analog 4 and primers (underlined).

FIG. 10 illustrates the coding sequence for single chain gonadotropin analog #5 and primers (underlined).

FIG. 11 illustrates the coding sequence for single chain gonadotropin analog #6 and primers (underlined).

FIG. 12 illustrates the coding sequence for single chain gonadotropin analog #7 and primers (underlined).

FIG. 13 illustrates the coding sequence for single chain gonadotropin analog #8 and primers (underlined).

FIG. 14 illustrates the coding sequence for single chain gonadotropin analog 9 and cassette (underlined).

FIG. 15 illustrates the coding sequence for single chain gonadotropin analog 10 and cassette (underlined).

FIG. 16 illustrates the preparation of an alpha-subunit coding region lacking oligosaccaride signal sequences.

FIG. 17 illustrates the preparation of a beta-subunit coding region lacking asn-linked oligosaccaride signal sequences.

FIG. 18 illustrates the coding sequence for single chain gonadotropin analog #1a.

SUMMARY OF THE INVENTION

Figure 1:
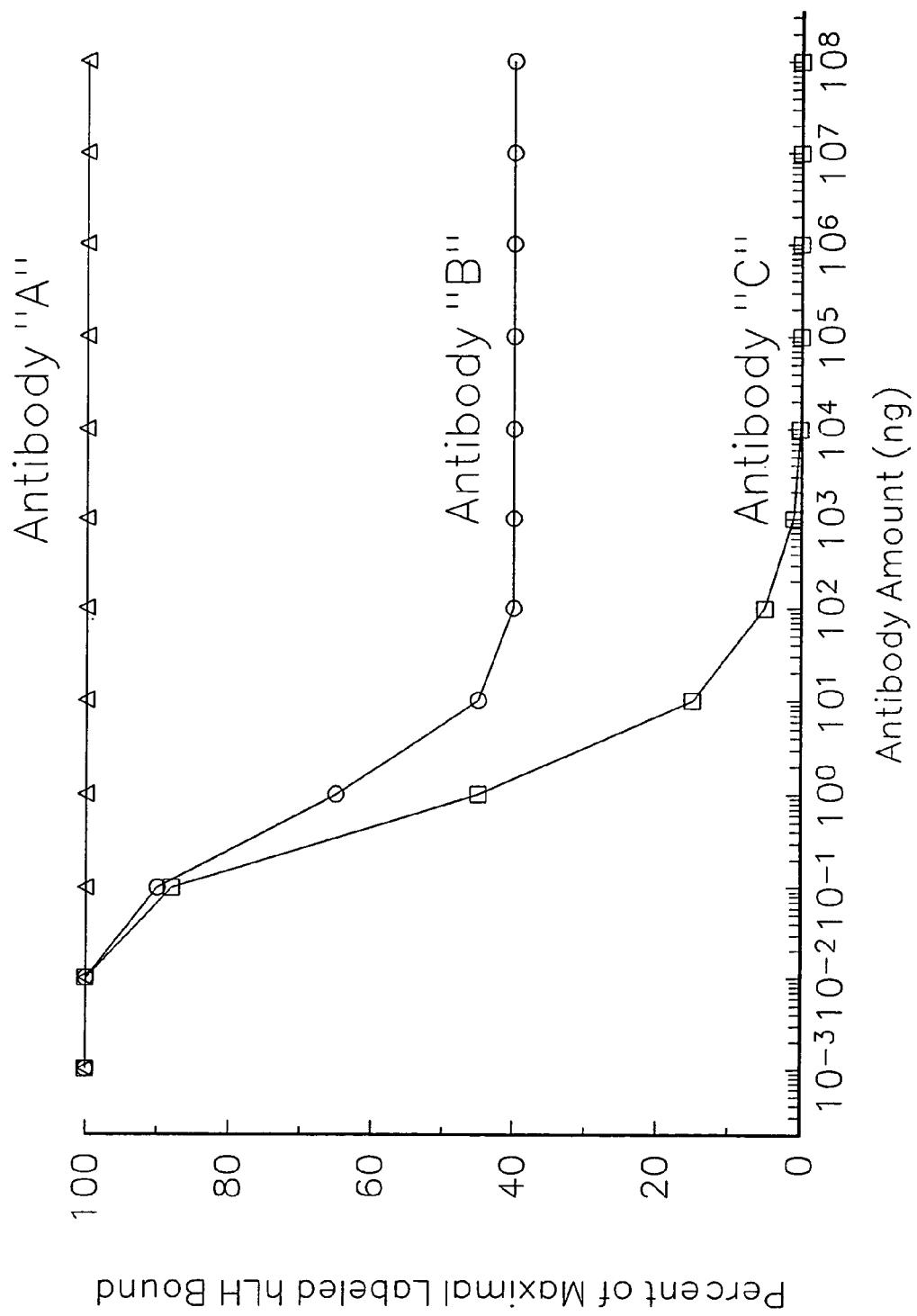
FIG. 1 is a graph illustrating the influence of antibodies and antisera on the binding of radiolabeled hLH to LH receptors.

The present invention relates to methods for enhancing fertility by reducing the activities and/or levels of circulating glycoprotein hormones having lutropin (LH) activity. The molecules of the invention are antibodies or other binding agents that reduce the biological activities of LH. The present invention also relates to novel methods for devising and/or selecting antibodies to specific portions of proteins including LH and human chorionic gonadotropin (hCG) to permit their biological activities to be reduced to desired degrees. The present invention also relates to the preparation of single subunit gonadotropins and gonadotropin antagonists for use in stimulating and inhibiting fertility and for controlling ovarian hyperstimulation.

In one embodiment, the present invention pertains to a method for stimulating fertility in mammals by reducing the activity of glycoprotein hormones having luteinizing hormone activity in circulation and thereby stimulating the production of follicle stimulating hormone which comprises administering to the mammal a therapeutically effective amount of a binding agent that binds luteinizing hormone.

In another embodiment, the present invention pertains to a vaccination method for stimulating fertility in mammals by reducing but not eliminating the activity of glycoprotein hormones having luteinizing hormone activity in circulation and thereby stimulating the production of follicle stimulating hormone which comprises the steps of:
  (a) providing binding agents that bind luteinizing hormone as positive templates;
  (b) providing a library of luteinizing hormone β-subunit mutants obtained by random mutagenesis of the luteinizing hormone β-subunit;
  (c) screening the luteinizing hormone β-subunit mutants from step (b) with the positive template binding agents from step (a);
  (d) discarding the luteinizing hormone β-subunit mutants that do not bind to the positive template binding agents in step (c);
  (e) determining the DNA sequence encoding the luteinizing hormone β-subunit mutants in step (d);
  (f) selecting the DNA sequence encoding the luteinizing β-subunit mutant that differs from luteinizing hormone but binds to luteinizing hormone binding agents with high affinity in step (e);
  (g) expressing the protein of the selected luteinizing hormone β-subunit mutant from the DNA sequence in step (f) in a prokaryotic or eukaryotic host; and
  (h) administering a therapeutically effective amount of the protein from step (g) to the mammal as an antigen to illicit an immune response thereby generating an antibody to luteinizing hormone to reduce but not eliminate luteinizing hormone activity and stimulate the production of follicle stimulating hormone to stimulate fertility in the mammal.

In yet another embodiment, the present invention pertains to a method for designing a vaccine for inducing infertility in female mammals by reducing the activity of glycoprotein hormones having chorionic gonadotropin hormone activity in circulation which comprises the steps of:

(a) providing binding agents that bind chorionic gonadotropin hormone as positive templates;

(b) providing a library of chorionic gonadotropin hormone β-subunit mutants obtained by random mutagenesis of the chorionic gonadotropin hormone β-subunit;

(c) screening the chorionic gonadotropin hormone β-subunit mutants from step (b) with the positive template binding agents from step (a);

(d) discarding the chorionic gonadotropin hormone β-subunit mutants that do not bind to the positive template binding agents in step (c);

(e) determining the DNA sequence encoding the chorionic gonadotropin hormone β-subunit mutants in step (d);

(f) selecting the DNA sequence encoding the chorionic gonadotropin β-subunit mutant that differs from chorionic gonadotropin hormone but binds to chorionic gonadotropin hormone binding agents with high affinity in step (e);

(h) expressing the protein of the selected chorionic gonadotropin hormone β-subunit mutant from the DNA sequence in step (g) in a prokaryotic or eukaryotic host; and (i) administering a therapeutically effective amount of the protein from step (h) to the mammal as an antigen to illicit an immune response thereby generating an antibody to chorionic gonadotropin hormone to reduce chorionic gonadotropin hormone activity to induce infertility in the female mammal.

In still yet another embodiment, the present invention pertains to a method for designing a vaccine for suppressing fertility in male humans by reducing the activity of glycoprotein hormones having follicle stimulating hormone activity in circulation which comprises the steps of:

(a) providing binding agents that bind follicle stimulating hormone as positive templates;

(b) providing a library of follicle stimulating hormone β-subunit mutants obtained by random mutagenesis of the follicle stimulating hormone β-subunit;

(c) screening the follicle stimulating hormone β-subunit mutants from step (b) with the positive template binding agents from step (a);

(d) discarding the follicle stimulating hormone β-subunit mutants that do not bind to the positive template binding agents in step (d);

(e) determining the DNA sequence encoding the follicle stimulating hormone β-subunit mutants in step (d);

(f) selecting the DNA sequence encoding the follicle stimulating β-subunit mutant that differs from follicle stimulating hormone but binds to follicle stimulating hormone binding agents with high affinity in step (e);

(g) expressing the protein of the selected follicle stimulating hormone β-subunit mutant from the DNA sequence in step (f) in a prokaryotic or eukaryotic host; and (h) administering a therapeutically effective amount of the protein from step (h) to the male human as an antigen to illicit an immune response thereby generating an antibody to follicle stimulating hormone to reduce follicle stimulating hormone activity and suppress fertility in the male human.

In still yet another embodiment, the present invention pertains to a method for designing a vaccine for suppressing fertility in nonhuman mammals by reducing the activity of glycoprotein hormones having luteinizing hormone activity in circulation which comprises the steps of:

(a) providing binding agents that bind luteinizing hormone as positive templates;

(b) providing a library of luteinizing hormone β-subunit mutants obtained by random mutagenesis of the luteinizing hormone β-subunit;

(c) screening the luteinizing hormone β-subunit mutants from step (b) with the positive template binding agents from step (a);

(d) discarding the luteinizing hormone β-subunit mutants that do not bind to the positive template binding agents in step (c);

(e) determining the DNA sequence encoding the luteinizing hormone β-subunit mutants in step (d);
(f) selecting the DNA sequence encoding the luteinizing β-subunit mutant that differs from luteinizing hormone but binds to luteinizing hormone binding agents with high affinity in step (e);
(g) expressing the protein of the selected luteinizing hormone β-subunit mutant from the DNA sequence in step (f) in a prokaryotic or eukaryotic host; and
(h) administering a therapeutically effective amount of the protein from step (g) to the mammal as an antigen to illicit an immune response thereby generating an antibody to luteinizing hormone to reduce luteinizing hormone activity and suppress fertility in the nonhuman mammal.

In a preferred embodiment, the methods for designing vaccines further comprise the steps of:

(i) in step (a), further providing binding agents that bind as negative templates;
(j) prior to step (c), screening the hormone β-subunit mutants from step (b) with the negative template binding agents from steps (i); and
(k) in step (c), screening the hormone β-subunit mutants that do not bind to the negative template binding agents from step (j) with the positive template binding agents from step (a).

DETAILED DESCRIPTION OF THE INVENTION

The present invention relates to methods for enhancing fertility by reducing the activities and/or levels of circulating glycoprotein hormones having lutropin (LH) activity. The molecules of the invention are antibodies or other binding agents that reduce the biological activities of LH. The binding agents can be administered or produced in response to immunization. Since molecules with lutropin activity are essential for fertility, blocking their activities would be expected to decrease rather than increase fertility. However, lutropins are usually found to enhance the production of steroids that can reduce the secretion of follitropins (FSH), hormones that have important roles in fertility. Consequently, reduction in the activities of lutropins leads to an increase in the levels of follitropins and/or the ratios of follitropin/lutropin. When LH activity is reduced but not abolished, the increase in FSH activity and/or the ratio of FSH/LH leads to enhanced production of gametes and elevated fertility in humans and animals. The present invention also relates to novel methods for devising and/or selecting antibodies to specific portions of proteins including LH and human chorionic gonadotropin (hCG) to permit their biological activities to be reduced to desired degrees. Examples are presented herein illustrating how to devise antibodies and immunogens against specific portions of selected gonadotropins, including those antibodies and immunogens that are very similar in structure. Some of these antibodies and immunogens will have uses for suppressing fertility and other antibodies and immunogens will have uses for enhancing fertility.

The present invention also relates to the preparation of molecules which can bind to LH and FSH receptors and have either fertility enhancing or fertility inhibiting actions depending on the time of administration. Some of these are molecules that will bind to LH receptors and block the action of LH. When these are administered in the follicular phase, they will suppress LH activity thereby suppressing androgen and estrogen secretion. Consequently, FSH levels will rise and fertility will be enhanced. When they are given after ovulation during the luteal phase of the menstrual cycle, they will suppress the activity of hCG and cause pregnancy to terminate. Other molecules bind to FSH receptors and have FSH activity. These are long acting analogs of FSH and when given in small amounts, they will stimulate follicular maturation. Because they will stimulate estrogen synthesis, the estrogen levels will rise and the secretion of pituitary FSH levels will fall. Provided these are administered in limiting amounts, they will not induce ovarian hyperstimulation. These will also have direct effects on stimulating fertility in males. In addition, the present invention relates to the preparation of molecules that have the ability to inhibit the actions of FSH and both FSH and LH. These molecules will be useful for treating women who have hyperactive ovarian tissue, often as the result of gonadotropin therapy. Hyperstimulation of the ovary is potentially fatal and these analogs bind to FSH receptors or to both FSH and LH receptors to suppress further ovarian development.

In accord with the present invention, methods are provided to improve fertility in humans and animals by the novel method of inhibiting the activity of lutropin using passive or active immunization. Previous studies have shown that blocking the actions of LH will lead to inhibition of fertility. Here it is shown that appropriate LH antibodies can be used to restore or stimulate fertility. This approach should reduce the risk of hyperstimulation and permit a more normal regulation of fertility with less monitoring. Several methods are provided for producing and testing the antibodies or antisera needed to promote fertility.

Other methods are available to alter the FSH/LH ratio including methods of administering FSH or giving antiestrogens. However, the procedure outlined here based on the use of anti-LH has important advantages over these other methods. The degree of maximal inhibition can be carefully determined for each antibody by in vitro testing. Thus, regardless of the amount of antibody administered, one could prevent inhibiting the activity of LH below a predetermined level by appropriate choice of antibody. For example B105 would reduce the effective hLH levels by a factor of approximately 4 whereas B110 will reduce the effective hLH levels by a factor of approximately 2. Reducing LH levels will permit FSH levels to rise. As FSH levels rise, they will cause follicular development and the production of estrogens. When these levels have reached the physiological concentrations characteristic of appropriate follicle development, they will negatively inhibit the secretion of more FSH. Thus, the treatment described here retains the valuable aspects of self-regulation that are missing in existing methods that depend on administration of FSH or anti-estrogens to stimulate fertility. Furthermore, unlike ovulation induction with GnRH (gonadotropin releasing hormone) or GnRH analogs, the method based on anti-LH does not require the pulsatile infusion of a hormone or hormone analog. This treatment offers the potential advantage of a single or at most a few treatments over several days. This will be particularly important in regulating ovulation in humans or animals. In humans, this method should be most appropriate for treatment of polycystic ovarian disease which is often characterized by inappropriately high levels of LH. As LH levels are reduced, FSH levels will rise and follicle development will occur. However, as follicle development occurs, the rising levels of estrogens will block the secretion of additional FSH. Thus, the tendency to promote the development of too many follicles with its dangerous potential consequences will be minimized.

Methods are also provided here for producing a specific immunogen which is based on use of template and exclusion antibodies. Use of these antibodies will enable one to devise a specific immune response to particular domains of a protein. This method will have uses in inducing or inhibiting fertility as illustrated here. Since antibodies against hCG can inhibit tumor growth, this method should also be useful to devise vaccines needed to inhibit development or progression of hCG-secreting tumors. The method should also have use in any system in which a specific immunogen is needed.

There is nothing unique about the structure of antibodies which makes them useful for inducing fertility other than the fact that they bind hLH or other LH. Thus, one would expect that portions of antibodies which retain the ability to bind LH would also have similar activity. These would include Fab fragments, (Fab')$_2$ fragments, single chain antibodies, or any molecule that bound to hLH or LH which reduced its biological activity. The Fab fragment is a portion of an antibody that contains the antigen binding site and is generated by papain digestion. The F(ab')$_2$ fragment is a portion of an antibody that contains two antigen binding sites and is generated by pepsin digestion.

Preferably, the methods for enhancing fertility are carried out during the follicular phase of the mammal, and more preferably during the follicular phase of the menstrual cycle.

The glycoprotein hormone to be regulated in the present invention is a reactant in a reaction between binding counterparts. The binding counterparts are proteins which have a specific binding affinity for each other. One binding counterpart is a bindable agent which is selected from the group consisting of an antigen and a hapten. The preferred bindable agent is an antigen. The other binding counterpart is a binding agent which is selected from the group consisting of an antibody and a specific binding protein. The preferred binding agent is an antibody.

Antigens are substances which are capable under appropriate conditions of inducing the formation of antibodies and of reacting specifically in some detectable manner with the antibodies so induced. Antigens may be soluble substances, such as toxins and foreign proteins, or particulate substances, such as bacteria or tissue cells. In general, antigens are high molecular weight substances such as simple and conjugated proteins and carbohydrates.

Antibodies are immunoglobulin molecules which have a specific amino acid sequence which permit it to interact only with the antigen which induced its synthesis in lymphoid tissue or with an antigen closely related to that antigen. Immunoglobulins are proteins made up of two light chains and two heavy chains.

The binding agent may also be a specific binding protein such as an unattached receptor protein or a transport protein. Receptor proteins include proteins which remain attached to cells such as antibodies and unattached proteins which are released to blood serum and retain their specific binding affinity. Transport proteins are proteins that move substances in and out of cells and across epithelial layers in biological systems.

The binding agents may be substances from natural sources or may be substances prepared by synthetic or recombinant means. In a preferred embodiment, the bindable agent is an antibody selected from the group consisting of recombinant proteins and synthetic peptides.

The compounds of the present invention can be administered to mammals, e.g., animals or humans, in amounts effective to provide the desired activity. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can vary from as low as about 0.1 $\mu$g per kg of body weight, which the practitioner may titrate to the desired effect. A preferred minimum dose for titration is 1 $\mu$g/kg body weight.

The present invention is further illustrated by the following examples which are not intended to limit the effective scope of the claims. All parts and percentages in the examples and throughout the specification and claims are by weight of the final composition unless otherwise specified.

EXAMPLES

Binding Agents that Reduce the Biological
Activities of Luteinizing Hormone and Human
Chorionic Gonadotropin to Permit their Biological
Activities to be Reduced to Desired Degrees Example 1

Use of Anti-LH Antibodies to Induce Fertility

Because some anti-hormone antibodies inhibit the biological activity of the hormones either by preventing the hormone from binding to receptors or by increasing its metabolism, they will be useful for reducing the level of active hormone in circulation. Antibodies to LH are capable of increasing the ratio of biologically active FSH to LH in circulation. In part, this is because they reduce the activity of LH. In addition, since LH is a hormone that stimulates the synthesis of steroid substrates that can be converted to estrogens (4), the decline in LH activity will be accompanied by a decline in estrogens. The decline in estrogen levels will reduce the inhibition of FSH secretion and levels of FSH will rise. As a consequence, in the female, follicular development will be enhanced. In the male, spermatogenesis will be augmented. Not all antibodies have the ability to reduce LH levels in a nonneutralizing fashion. Antibodies that neutralize the actions of LH completely will curtail fertility unless administered in a limiting fashion (i.e., the total amount of antibody given is less than the total amount of circulating LH). Nonneutralizing antibodies are preferred for enhancing fertility since they can be given in excess of the total amount of LH. Thus, even although most LH may be bound to the antibodies, the LH activity is reduced but not neutralized. Because there is more than sufficient LH for follicle development, the partial reduction in LH activity does not prevent follicle development. In addition, the increased estrogens that are made as the follicle increases its development will mimic the normal feedback control of FSH secretion to prevent ovarian hyperstimulation. Administration of 10 μg-10 mg of high affinity antibody (i.e., $K_a > 5 \times 10^7 M^{-1}$) will be sufficient to induce fertility in women having polycystic ovarian disease. Identification and characterization of appropriate antibodies is illustrated in example 2.

Example 2

Identification and Selection of the Best LH Antibodies

Not all antibodies that inhibit LH activity will be equally useful for treatment of infertility. For example, high excess concentrations of antibodies like B101 that bind to hCG and LH (albeit with lower affinity) can prevent the hormones from binding to LH receptors (22). When present in excess, antibodies that prevent binding of LH or hCG to its receptors "neutralize" the biological activity of the hormone. While neutralization of LH would be followed by a decline in androgen and estrogen levels and a rise in FSH levels, since LH is needed for fertility, the reduction of LH activity below the minimal level needed for fertility would prevent fertility as long as an excess of the antibody was present. Indeed, neutralizing antibodies or antigens that elicit the production of neutralizing antibodies have been shown to inhibit fertility in animals (10). It would be possible to administer limited amounts of neutralizing antibodies to reduce LH concentrations to a predetermined level or to reverse the inhibitory effect of a neutralizing antibody by administering an anti-idiotypic antibody. However, due to the variations between individuals it would be difficult to determine how much antibody would be needed to obtain the desired effect unless nearly complete inhibition of LH activity were desired or unless measurements of FSH and/or gonadal function (e.g., determining plasma steroid levels) were performed. While these are feasible, the need to make these measurements reduces the attractiveness for using antibodies that completely neutralize LH activity to augment fertility. Neutralizing antibodies could also be given to prevent the action of LH temporarily until FSH levels had risen. Then the excess neutralizing antibody could be removed by administration of an anti-idiotypic antibody to neutralize anti-LH antibodies to restore fertility or by overcoming the effect of the antibody using LH or CG or by using an amount of antibody that would be sufficiently degraded to permit the action of the LH midcycle surge. However, this approach is more complex than use of nonneutralizing antibodies, illustrated below.

The preferred antibodies inhibit the activity of LH but fail to completely block its action even when given at concentrations sufficient to bind all the LH present in circulation. These antibodies are usually capable of binding to the free hormone as well as to hormone-receptor complexes. They inhibit hormone action by lowering the affinity of the hormone for its receptor, reducing the activity of bound hormone, and/or increasing hormone clearance. Examples of such antibodies include B105 and B110. These antibodies reduce the biological activities of the hormones to different extents (17) and can be purchased from Columbia University, New York, N.Y or UMDNJ-Robert Wood Johnson Medical School, Piscataway, N.J. Other commercially available antibodies include 518B7 (available from Dr. Janet Roser, University of California at Davis, Davis, Calif.) and ZMCG7 (available from Pierce Chemical Co., 3747 North Meridian Road, Rockford, Ill.). Because complexes of these antibodies with hCG can bind to receptors, the degree of inhibition is limited even in the presence of a massive antibody excess. The amount of inhibition can be determined from simple in vitro assays prior to their use in vivo. For example, a massive excess of B110 was shown to reduce the activity of hCG by only about half whereas a massive excess of B105 reduced the activity of hCG by about three-quarters. Each of these antibodies binds to hLH and would be expected to have the same influence on hLH activity.

The identification of appropriate antibodies from a panel of monoclonal antibodies made against hLH can be made as follows. These antibodies can be obtained by standard procedures (22,27–32) by immunizing mice with hLH, hCG, or LH from other species, LH or hCG fragments, partially or fully deglycosylated LH or hCG, or LH or hCG analogs capable of eliciting an immune response to the desired species of LH. These antibodies could also be obtained by selection of manmade antibodies (33–36). This same strategy could be used to identify antibodies to LH from virtually any other species. It could also be used to identify antisera which have similar properties. These antisera could be made in response to LH or hCG analogs or they could be obtained by immunoadsorption or removal of undesirable antibody components.

Antibodies having the desired inhibitory characteristics can be identified by measuring their abilities to inhibit the binding of LH to LH receptors. This type of assay can be performed by one skilled in the art of measuring receptor binding and the following example refers to how one would select for antibodies to hLH. Clearly, this would also be applicable to any species of LH for which antibodies were available. Since hLH binds well to rodent LH receptors, one need not use human LH receptors in the assay, although human LH receptors would also work. A simple first step is to monitor the influence of the antibody on the binding of radiolabeled hLH to rat ovarian luteal LH receptors. The radiolabeled hLH can be prepared by incubating 10 μg hLH with 500 μCi of $Na^{125}I$ for 30 seconds at 4° C. in a small glass tube that has been coated with 1.5 μg Iodo-Gen (Pierce Chemical Co.). $^{125}I$-hLH and unreacted $^{125}I$ are separated by gel filtration. The receptors can be prepared by administering 50 IU of pregnant mares serum gonadotropin also known as PMSG or equine CG (obtained from Sigma Chemical Co., St. Louis Mo.) to female Sprague-Dawley rats that are 23–26 days old. The PMSG stimulates follicle development. Approximately 56–65 hours later the animals are given 25 IU of hCG (also obtained from Sigma Chemical Co.) to cause the formation of corpora lutea. The highly luteinized ovaries are removed one week later and homogenized in a buffer containing 40 mM Tris (pH 7.4) and 5 mM $MgCl_2$. A crude nuclear and membrane fraction of the homogenate is collected by centrifuging the homogenate at 1000×g for 20 minutes at 4° C. This is washed once by resuspending it in the Tris-$MgCl_2$ buffer and resedimenting it at 1000×g for 20 minutes at 4° C. The final pellet (termed the "ovarian homogenate pellet") is resuspended in the Tris-$MgCl_2$ buffer using a volume of 2 ml per each ovary present at the start of homogenization. An amount of ovarian homogenate pellet approximately equal to ¹⁄₂₀ of an ovary (i.e., roughly 5 mg of material in 100 μl of buffer) is added to tubes that contain approximately 1–2 ng radioiodinated hLH (i.e., approximately 100,000 cpm) and differing amounts of antibody (i.e., ranging from 1 pg to 10 μg or more). After the tubes have incubated sufficient time to permit the radiolabeled LH to bind to the receptors (i.e., 30–60 min at 37° C. or overnight at room temperature), the receptor bound and free radiolabels are separated by diluting the reaction mixture to 2 ml with 0.9% NaCl solution, centrifuging the mixture, and aspirating the supernate. The amount of radiolabeled hLH bound to rat ovarian LH receptors is determined by analyzing the pellet in a gamma counter. One would expect to observe the types of inhibition shown in FIG. 1. Some antibodies will completely inhibit the binding of radiolabeled hLH to the same extent as a massive excess of unlabeled hLH or hCG whereas others will not inhibit binding or may even potentiate binding when present in vast molar excess relative to radiolabeled hLH. Both these types of antibodies are less desirable than those antibodies which suppress hLH binding to an intermediate level (c.f., FIG. 1). Thus, the most useful antibodies will inhibit the binding of the radiolabeled LH but not to the same extent as a massive excess of unlabeled LH. Antibodies that inhibit the binding of radiolabeled LH to the same extent as a massive excess of unlabeled LH will also be useful but greater care will be needed to be certain that the antibody will not suppress LH activity too much when used in vivo. If too much LH activity is neutralized in the LH surge, infertility will result.

Figure 2:
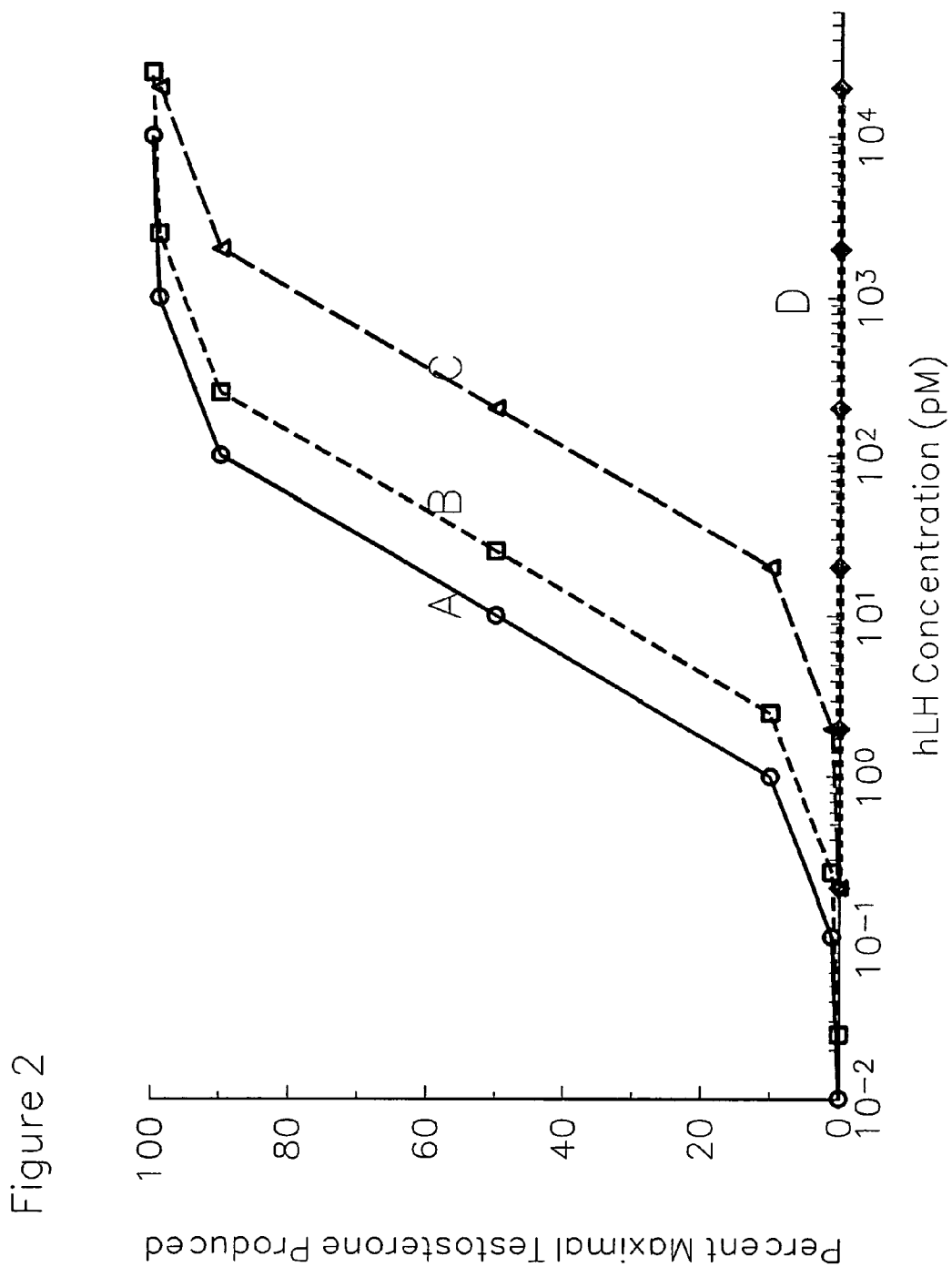
FIG. 2 is a graph illustrating the influence of antibodies and antisera on the ability of hLH to induce steroidogenesis in vitro.

Another useful procedure to identify antibodies having the desired ability to reduce LH activity is to perform an in vitro test to determine if the antibodies inhibit the effect of hLH on steroid biosynthesis. In this assay one can utilize testes from male rodents. A typical example using hLH is illustrated in FIG. 2. A crude rat Leydig cell suspension is prepared using collagenase as described (37) and the cells are incubated with varying amounts of LH and the antibodies to be tested. After approximately 2–4 hours at 37° C., the testosterone content in the tubes is measured by radioimmunoassay. When increasing concentrations of hLH are incubated with the Leydig cells, they cause enhanced production of testosterone and will give rise to a typical dose response curve in which hLH concentrations of 1–10 pM will be sufficient to elevate steroid production by approximately 50% of the maximal level (see FIG. 2, curve A). The most useful antibodies are identified by their abilities to inhibit LH induced steroidogenesis. When different monoclonal antibodies are added to LH before the hormone is added to the cells, some will be found to reduce the ability of LH to stimulate testosterone formation. The most useful inhibitory antibodies will shift the dose response curve to less sensitive values (see FIG. 2, curves B and C). While the degree of the shift will initially be dependent on the concentration of antibody, a massive excess of antibody (i.e., more than 100-fold greater than the maximal amount of hLH used) will not prevent LH-induced testosterone formation. The least useful antibodies will prevent the stimulation of testosterone formation when the antibody is present in 100-fold molar excess (see FIG. 2, curve D). This type of assay will detect antibodies that inhibit LH activity by reducing its binding to LH receptors and it will also detect antibodies that inhibit the activity of bound LH. Examples of useful antibodies include B105, B110, 518B7, and ZMCG7, noted above. These will need to be modified as described below before they can be used repeatedly in women.

Figure 3:
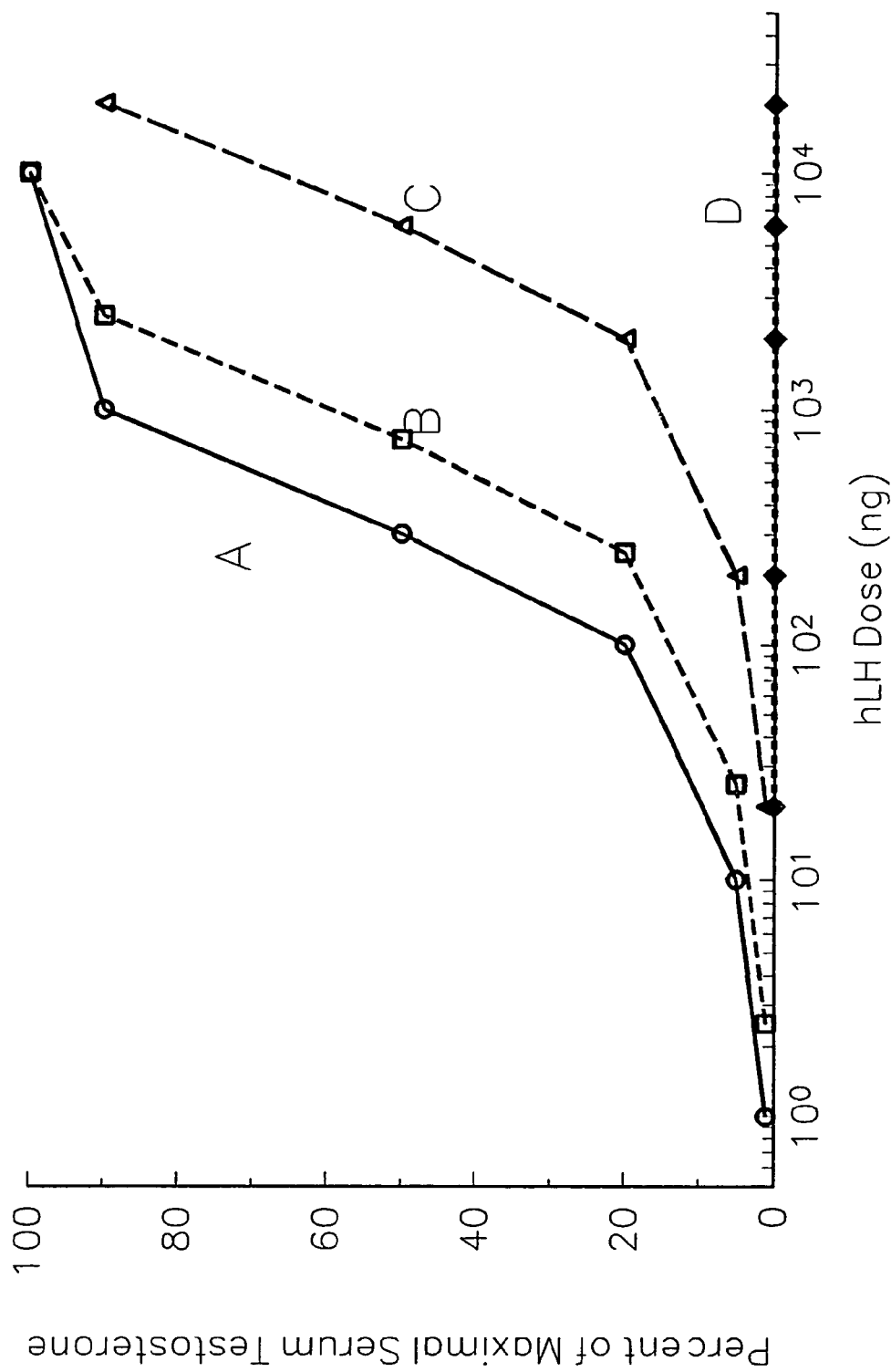
FIG. 3 is a graph illustrating the influence of antibodies and antisera on the ability of hLH to induce steroidogenesis in vivo.

Once antibodies or antisera have been selected and found to satisfy the criteria described above and illustrated in FIGS. 1 and 2, they should be tested for their abilities to inhibit the actions of LH in vivo. Male rats are given a large excess of antibody (i.e., 100 μg or more). Twenty minutes later some of the rats are treated with vehicle alone (control) and others are given hLH or LH similar or equal in structure to that from the animal for which the antibody is to be used. One hour later, the plasma testosterone levels are measured by radioimmunoassay. A typical example is illustrated in FIG. 3. The most useful antibodies or antisera will reduce the potency of hLH but will not prevent its activity even when present in excess of the total amount of LH given. This assay will detect antibodies that reduce hormone activity by inhibiting LH binding to receptors, inhibiting the activity of bound LH, and/or increasing LH clearance. Regardless of the cause of inhibition in vivo, the most useful antibodies or antisera will not prevent the activity of high levels of LH even when they are present in excess of circulating LH. This can be monitored by measuring the ability of the serum to bind radioiodinated hLH after administration of the antibody. A serum sample (0.01–1 μl) is diluted to 25 μl with a solution containing 0.9% NaCl, 1 mg/ml bovine serum albumin, and 0.02 M sodium phosphate buffer (pH 7.2). To this is added 25 μl of radioiodinated LH (approximately 50 nCi containing approximately 1 ng). The resulting solution is incubated 30 minutes at 37° C. A goat antimouse immunoglobulin G (IgG) solution (available from Cappel, Organon Teknia Corp, West Chester, Pa.) containing 2 μg IgG in 50 μl of the NaCl-albumin solution described above is added and the resulting solution incubated 90 minutes at 37° C. or overnight at 4° C. To this solution is added 100 μl of 1% IgGsorb (obtained from The Enzyme Center, Inc., 36 Franklin St., Malden, Mass.) reconstituted in water. This suspension is mixed for 30 minutes at 22° C. and then diluted by addition of 3 ml of the NaCl-albumin solution that is ice cold. The mixture is centrifuged for 10 minutes at 2000×g at 4° C. The supernate is aspirated and radioactivity in the pellet is measured in a gamma counter. As a negative control, one uses serum from an animal that has not been actively or passively immunized. As a positive control, one uses 0.1–1 ng of the antibody that was originally injected into the animal. The radioactivity measured in the pellet from the negative control is subtracted from that in the positive control and from that in pellets of the serum samples that are being tested. When the resulting values for the positive control and the serum samples are compared, serum that contains antibody in excess of LH will be able to immunoprecipitate at least 1%–10% of the radioiodinated LH as the positive control.

Administration of antibodies to hLH in humans will reduce the effective concentrations of circulating LH. The maximum amount of reduction depends on the location of the binding site of the antibody on LH. Reduction in LH activity lowers the secretion of ovarian and testes hormones and thereby reduces the feedback inhibition of FSH. Consequently, FSH levels rise and fertility is enhanced. Antibodies to hLH that crossreact with LH from other species or antibodies that have been selected for their abilities to bind to LH from other species and reduce but not abolish hormone activity will have similar effects in the other species. The most appropriate antibodies for use in humans will be those that have framework and constant regions that are similar to human immunoglobulins and that are themselves not antigenic or only weakly antigenic when injected into humans. Suitable antibodies can be prepared by "humanizing" mouse monoclonal antibodies (i.e., replacing the mouse framework and constant regions with similar sequences found in human immunoglobulins. Procedures to accomplish this are well-known in the art (38–40). Other methods of making suitable antibodies include immunization of primates such as the Cynomolgus monkey (41) followed by isolating and cloning of single lymphocytes (42). The immunoglobulins in these primates have similar framework regions as human immunoglobulins. Monoclonal antibodies prepared from these animals should serve as a good starting point for antibodies that can be used in humans.

Example 3

Alternative Methods for Obtaining and Selecting Desired Antibodies

Many antibodies that are capable of partial inhibition of hLH activity have a propensity to bind to hLH or other LH molecules that have been adsorbed to plastic or other surfaces. Therefore, screening for desired antibodies is often facilitated by monitoring the abilities of the antibodies to bind to hLH or other LH that is adsorbed to plastic microtiter plates or to LH that is bound to LH receptor complexes. Screening for antibodies that bind to hLH that is adsorbed to a plastic surface can be accomplished as follows. The wells of a plastic microtiter plate are coated with 50 µl of a solution containing 0 or 1 µg hLH in 0.9% NaCl-0.02 M sodium phosphate buffer (pH 7.2). This enables the hLH to be adsorbed to the surface of the microtiter plate. After 1 hour at 37° C., the solutions are removed and replaced with 200 µl of 0.9% NaCl-0.02 M sodium phosphate buffer (pH 7.2) containing 200 µg bovine serum albumin for longer than 1 hour at 37° C. This fills most of the remaining adsorption sites. The albumin solution is removed and replaced with 50 µl of 0.9% NaCl-0.02 M sodium phosphate buffer (pH 7.2) containing 50,000–100,000 dpm of the test monoclonal antibody labeled with $^{125}$I. Labeling of the monoclonal antibody is performed using Iodo-Gen or other oxidizing agent (22,43) as described above for LH using 10 µg of antibody and 500 µCi of NaI$^{25}$I except that the reaction time is extended to 1–5 minutes. After 1 hour at 37° C., the fluid is removed and the radioactivity that is attached to the surface of the microtiter plate is measured in a gamma counter. Antibodies that have a high probability of being useful for inhibiting hLH activity will be found to be bound to the wells coated with hLH in amounts greater than those to the wells not coated with hLH. This assay will also detect other types of antibodies as well and a further screen of the positive antibodies should be performed as outlined below or as in example 2.

While binding to LH-receptor complexes does not guarantee that an antibody will be useful for partially neutralizing LH activity, many of the preferred antibodies bind to LH-receptor complexes. Thus, it is possible to initially screen for desirable antibodies by measuring their abilities to bind to LH-receptor complexes. This assay is essentially the same as the Bio-IRMA that has been described previously (44) and can be performed in a sequential or simultaneous fashion. In the simultaneous Bio-IRMA, 0.025 µCi —0.1 µCi of the radioiodinated test antibody (i.e., prepared as described above) is added to a rat ovarian homogenate (i.e., prepared as described above), and increasing amounts of LH including 0, 0.01, 0.1, 1.0, 10, 100, and 1000 ng. After 1 hour at 37° C., the membraneous part of the homogenate is sedimented into a pellet by centrifugation at 1000×g for 10–20 minutes, the supernate is aspirated, and the radioactivity in pellet determined in a gamma counter. Antibodies that bind to LH receptor complexes will be detected by their increased ability to bind to membranes incubated with at least one of the LH concentrations over the assay blank (i.e., no LH added). In the sequential Bio-IRMA, the membranes are incubated with the LH first for 1 hour at 37° C., washed by centrifugation and aspiration as described above and then incubated with 50,000–100,000 dpm of radioiodinated antibody. After an additional 1 hour incubation at 37° C., the bound and free antibody fractions are separated by centrifugation and aspiration as described above and the pellet is counted in a gamma counter. Most useful antibodies will bind to the LH-receptor complexes. However, this procedure is only a useful screening method and a more conclusive test of an antibody involves use of an in vitro biological assay such as that based on testosterone formation that is described in Example 2.

The propensity of the most useful antibodies to bind to surfaces that contain LH or to complexes of LH and LH receptors can also facilitate isolation of lymphocytes following immunization of monkeys or mice using a panning procedure. In this procedure, lymphocytes are added to plastic surfaces that have been coated with human serum albumin or other protein that prevents nonspecific binding by exposing them to solutions containing 1 mg/ml of human serum albumin in 0.9% NaCl-0.02M sodium phosphate buffer (pH 7.2) for longer than 1 hour at 37° C. The lymphocytes that do not bind to these surfaces are then added to surfaces that are coated by exposing them to hLH and then to human serum albumin as above. The amount of hLH used is not critical so long as sufficient material has become adsorbed to the plastic. This can be achieved using 20–50 µg of hLH/ml. However, lesser and greater amounts will also work. The lymphocytes that attach to surfaces coated with LH are selected and either fused with myeloma cells to prepare hybridomas (30), transformed with Epstein-Barr or other virus, subjected to cloning in lambda phage (36), or single cells are selected for polymerase chain reaction cloning (42). The antibodies that are produced are subjected to screening as outlined in example 2. These strategies enhance the percentage of antibodies that will be desirable.

Many antibodies that are capable of partial inhibition of LH can also be selected through a process that depends on their abilities to bind to LH that is bound to LH receptors. Following immunization of mice or monkeys with hLH, the spleen cells and other lymphocytes are isolated and layered on eukaryotic cell monolayers that express LH receptors. These cell monolayers can be prepared by transfecting cells with expression vectors capable of expressing rat (45), human (46), porcine (47), or other LH receptor cDNA by methods which are standard in the art (48,49). Lymphocytes that adhere to the monolayers are discarded. Lymphocytes that do not adhere to the monolayers are added to similar monolayers of cells expressing LH receptors containing hLH or other LH. These can be prepared by adding 100 ng of hLH or other LH to the monolayers overnight at 4° C. and washing off the hormone that did not become bound. Lymphocytes that adhere to these cells are selected and either fused with myeloma cells to prepare hybridomas (30), transformed with Epstein-Barr or other virus, or subjected to polymerase chain reaction cloning (42). The antibodies that are produced are subjected to screening as outlined in example 2. These strategies will also enhance the percentage of antibodies that will be desirable. Although this receptor-based strategy is more tedious than a strategy based on screening of lymphocytes on plastic surfaces coated with LH, it will yield a higher percentage of useful antibodies.

Example 4

Use of Antibody to Treat Polycystic Ovarian Syndrome

Polycystic ovarian syndrome (PCO) is characterized by incomplete follicle development and an inability of a woman to ovulate normally. The ovary contains many small immature follicles, few if any of which progress to the point of ovulation in the absence of clinical intervention. These woman often have elevated androgens and a high ratio of LH/FSH relative to normally cycling fertile women. There are two major procedures for induction of ovulation in women with PCO. These include the administration of FSH to boost follicle development or anti-estrogens to facilitate the secretion of FSH from the anterior pituitary gland. While both treatments are capable of inducing ovulation, they have a risk of inducing multiple ovulations since they bypass the normal negative estrogen feedback loop which regulates FSH secretion. As a result, women treated with these agents are usually monitored carefully to prevent hyperstimulation, a potentially lethal side-effect of treatment.

Administration of 10 µg–10 mg of a nonneutralizing antibody to LH that causes a transient and self-limiting rise in FSH secretion will induce ovulation with less risk of hyperstimulation than treatment with gonadotropin. The effect is transient because the antibody will be metabolized or otherwise cleared from the circulation and its effectiveness will be lost within 1–2 weeks after administration. The treatment is self-limiting because the negative feedback effect of estradiol on FSH secretion will not be eliminated. Thus, as FSH levels rise and stimulate follicle development, estradiol secretion will rise and inhibit further increases in FSH secretion.

Example 5

One or Two Dose Treatment Induction of Ovulation

There are no good methods that can be used to induce ovulation in women with PCO that involve only a single or double treatment. Most treatments for this syndrome require multiple treatments with FSH, FSH plus LH or hCG, hMG, anti-estrogens, GnRH, or various combinations of these agents. Some approaches have also employed GnRH antagonists to reduce the circulating levels of both LH and FSH so that ovulation could be induced by treatment with exogenous hormones. A single administration of a high concentration of the preferred antibody of the type described here can induce ovulation. This is because the antibody can be given safely in massive excess and, since antibodies have long plasma half-lives, the antibody will continue to be effective in increasing FSH levels for several days. Because of the natural feedback effect of estradiol on FSH secretion, FSH secretion will be controlled by the estrogens made by the follicle as the follicle develops. By the time that the dominant follicle has been selected and estradiol levels have increased, much of the antibody will have been cleared from circulation. The antibody will not interfere with the actions of LH surge needed for ovulation for one or more of several reasons. First, the amount LH released is in excess of the amount needed for ovulation. Second, the antibody will only reduce the activity of LH, not neutralize it. And third, by the time of the LH surge much of the antibody will have been cleared from circulation. Thus, treatment with the antibody will be followed by follicle development and ovulation.

Example 6

Antigens that Induce Appropriate Inhibitory Antisera

Administration of appropriate antibodies illustrated in Example 1 can be used to augment fertility. However, since this is a "passive" immunization, it will require repeated administration of antibody to keep the levels of antibody high for more than several days or weeks. Short term elevation (e.g., days) is sufficient for inducing ovulation in women or increasing the number of ovulations in animals in one or a few cycles. When it is desired to partially suppress the activity of LH and thereby augment fertility for longer periods or several cycles, it is useful to induce an immune response that causes the active formation of antibodies against LH. To obtain the most useful antibodies, it is necessary to design an immunogen capable of inducing a response to a portion of the LH molecule similar to that recognized by B105, B110, or other antibodies that form complexes with LH that retain some LH activity. The most appropriate immunogens are derived from the LH β-subunit since this subunit is unique to LH. The α-subunit is common to LH, TSH, and FSH. Its conformation appears to differ slightly in the hormones (21) and, therefore, useful antibodies against the α-subunit can also be made. However, antibodies to the alpha-subunit have the potential of inhibiting the actions of all three hormones. If the immune response is directed against hFSH, it may not enhance fertility and may cause infertility. When it is desirable to actively immunize women against hLH to enhance fertility, care must be taken to prevent the induction of antibodies to hCG. Antibodies to hCG have the potential to reduce fertility (see below). This is usually not a problem with passive immunization described above since the administered antibodies to LH are usually cleared from circulation prior to the time that hCG is needed for fertility.

Antigens capable of inducing the formation of antibodies against a portion of LH that does not neutralize its activity (i.e., the desired immune response) contain a sequence derived from a portion of the LH β-subunit. Often this is a region of the beta-subunit that remains exposed after LH binds to LH receptors. To be most antigenic the immunogens should also contain sequences that are foreign to the person or animal to be immunized. If the entire LH β-subunit is used for immunization, one can get the production of antibodies that completely inhibit LH activity. High titers of neutralizing antibodies may result in infertility or have other negative consequences such as inducing premature menopause or loss of testis size or function. The best choice of LH beta-subunit residues that should be included in the immunogen are those that remain exposed when the hormone binds to LH receptors. These include the portion of the hormone near residues 74–77, a region of the hormone that is recognized by antibodies that bind to hLH or hCG β-subunits and hLH- or hCG-receptor complexes (26,50). Regions of the β-subunit that should not be used for immunization include sequences near residues 89–92 and 47–51. These are the locations of the binding sites for antibodies that neutralize activity.

The design of a minimal synthetic antigen includes residues of hLH subunit exposed when LH is bound to LH receptors. Some of these include Pro73-Arg74-Gly75-Val76-Asp77-Pro78-Val79-Val80-Ser81 (SEQ ID NO:24), synthetic peptides containing these sequences can be coupled to large carrier molecules and used for immunization using methods well-known in the art (14–16,51–53). The nonneutralizing antibodies produced will combine with hLH and inhibit its biological activity.

Often the ability of small peptide antigens to elicit a high titer immune response is low. The following illustrates how to create an antigen which will be more effective in eliciting antibodies to regions of hLH that remain exposed when the hormone binds to LH receptors. A similar approach could be used to design immunogens for any protein including other vertebrate LH. The best immunogens are well-known to be those that differ substantially from proteins found in an animal yet retain the tertiary configuration of the epitope or epitopes for which an immune response is desired. An appropriate immunogen can be made by modifying the hLH β-subunit such that i) it retains the ability to bind to B105 and/or other antibodies that partially inhibit the actions of hLH, ii) it loses the ability to bind to antibodies that neutralize LH activity, and iii) it is antigenic. Appropriate immunogens can also be designed starting with a protein other than the LH beta-subunit and modifying it to acquire the ability to bind to B105 and/or other antibodies that partially inhibit the actions of hLH. Antibodies that partially inhibit the actions of hLH are termed "template" antibodies and they are used to monitor and/or positively select for retention of desired epitopes. Good examples of template antibodies are those that are found to be effective in increasing fertility as outlined in example 2. Other antibodies which are termed "exclusion" antibodies are used to select against antigen analogs containing undesirable epitopes. Examples of "exclusion" antibodies are those which completely neutralize the biological activity of hLH and/or which prevent it from binding to its receptor.

There are two overall different strategies which will be termed "A" and "B" for building the antigens using a positive/negative selection strategy based on template and exclusion antibodies. In approach "A", one starts with the LH β-subunit and uses random mutagenesis to make substitutions in regions of the molecule outside the epitope recognized by the "template" antibody. The new molecules that are produced are expressed (see below) and their abilities to bind the template antibody are monitored. Those that continue to bind to the template antibody and have mutations in the other regions of the molecule are utilized in a second round of mutagenesis on a different portion of the molecule. This process is continued until all regions of the protein except the one involved in the antibody binding site (e.g., B105) have been modified. The final analogs will bind to template antibodies but not to exclusion antibodies. In a variant of this procedure, one begins with a hormone chimera that binds to the template antibody. Such chimeras can be prepared starting with a different species of LH known not to bind template antibodies or to induce a neutralizing immune response to hLH. Examples of this type of immunogen are chimeras of the β-subunits of human LH and bovine LH. These include bovine LH β-subunit that has been modified by substituting proline 74 with arginine, the residue found in the human LH β-subunit at this position. Residues of hLH are substituted for homologous regions of the different species of LH to create the binding site for the template antibodies. The homologous regions are identified by aligning the sequences of hLH and the other LH by the positions of their highly conserved cysteine residues as shown by Pierce and Parsons (1).

In approach "B" one uses a framework molecule that is not related or only weakly similar to the structure of glycoprotein hormone β-subunits. This can include any protein containing loop structures such as those found in the immunoglobulin folds or between the helices in four helix bundle proteins. The sequence of hLH between residues 65–85 is substituted for one of the loops by standard mutagenesis procedures. When this protein is made in a suitable E. coli expression vector (e.g., one of the T7 vectors obtainable from Novagen), it can be tested for its ability to bind to monoclonal antibodies that bind to hLH-receptor complexes. Since only a portion of the residues which form the epitope will be present in the expressed protein, its affinity will be lower than that of hLH for the antibody.

To improve the selectivity and affinity of the proteins made in approaches "A" or "B," one can use either a bacterial or bacteriophage expression system (34,36,55–58). In either case one prepares libraries of mutant analogs and selects the mutant having the highest affinity for B105, B110, or other similar template antibody that is found to be useful in example 2. In addition, one can also use negative selection using neutralizing antibodies or antisera found not be useful in example 2. This will minimize the ability of the antigen to elicit undesirable antibodies when used in a vaccine.

Figure 4:
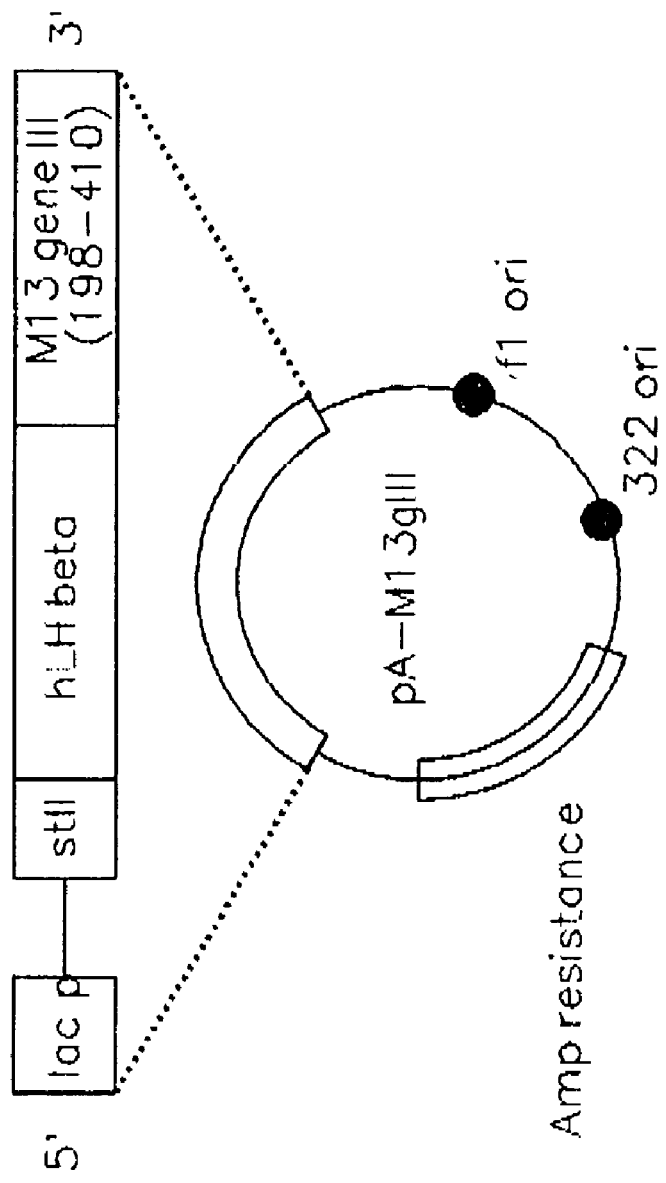
FIG. 4 shows vectors that can be used in template/exclusion selection strategies.

The following description applies to a selection method based on phage display but could be readily adapted by one skilled in the art of making and screening libraries to nearly any expression system. One system which is amenable to selection is that based on protein blotting (59). Several different phage display systems can also be used. One involves using a vector (i.e., pX-M13gIII) similar to phGH-M13gIII (34). When approach "A" discussed earlier is used, this new vector termed pA-M13gIII contains either hLH β-subunit or an hLH-LH β-subunit chimera in place of the growth hormone coding sequences of phGH-M13gIII (FIG. 4). When approach "B" discussed earlier is used, the growth hormone coding sequences of phGH-M13gIII are replaced with a gene encoding a molecule unrelated to hLH β-subunit except for the inclusion of the hLH beta subunit coding sequences near residue 74 to give a new vector termed pB-M13gIII. The coding sequence of the region of the vector encoding the "B" sequences also contains restriction sites that permit cassette or other types of mutagenesis to permit introduction of random sequences. When random sequences are introduced into the coding regions of pA-M13gIII or pB-M13gIII vectors and the vectors used to transform E. coli, a library of mutants will be created. These mutant proteins can be expressed on the surface of M13 phagemid particles as gene III fusion proteins by adding the helper phage M13KO7 to the E. coli. These phagemid particles will bind to the antibody in proportion to the affinities of the modified proteins "A" or "B" for the antibody. One convenient method to select for phagemid particles that bind to template antibodies is to use a solid phase assay protocol. In this assay, the template antibody is used to coat a surface as described (22) and then a solution containing the phagemid particles is added. Phagemid particles that do not bind to the surface can be discarded. Those particles that do bind to the antibody on the surface can be removed from the antibody by the addition of low pH buffers (i.e., pH3) and used to retransform E. coli. When a negative selection is desired, one can substitute the exclusion antibodies for the template antibodies on the surface. In this case the particles that attach to the surface are discarded. This process is repeated several times and then the coding regions of several genes for the "A" and "B" proteins are subjected to DNA sequencing. In this way one can identify sequences that are critical for template antibody binding. In addition, if exclusion antibodies are used, one can select against undesirable epitopes. Also, one can identify substitutions in other portions of the molecule that have little or no effect on the conformation of the desired antibody binding region. When molecules encoded by these sequences are used to immunize animals or humans, they will elicit the formation of antibodies that crossreact with hLH. Since these antibodies will recognize a portion of the molecule known to be exposed after hLH binds to its receptors, they will be able to inhibit the actions of hLH but not completely prevent its biological activity.

In some cases template antibodies and exclusion antibodies may not be available. In these cases one can create template antisera and exclusion antisera which can be substituted for the antibodies using the following strategy. Rat ovarian corpora lutea are prepared by treatment of female rats with PMSG and hCG as described earlier. These corpora lutea are incubated with hLH to permit the hormone to bind to the LH receptors in the membranes. Then the membranes are washed to remove the free hLH and the membranes are incubated with the antisera. Antibodies which become bound to the hLH which is bound to the membrane LH receptors are then separated from the remainder of the antisera by washing the membranes. These antibodies are released by treatment of the membranes at a pH below 5. This treatment releases both the antibodies and the hLH from the receptors. The antibodies are separated from hLH by gel filtration or other method and then can be used as templates. Antibodies remaining in the serum depleted of template antibodies can serve as exclusion antibodies.

Example 7

Development of an Immunogen to Elicit Neutralizing Antibodies to hCG

The preferred immunogens for preventing fertility will elicit the production of antibodies against hCG but not hLH. These can be made using the template/exclusion procedure described in example 6 employing different antibodies. Template antibodies that can be used include B107 and B109 available from Columbia University. These antibodies bind hCG with high affinity and have very low affinity for the free hCG β-subunit or for hLH. Because they are specific for the heterodimer form of hCG (i.e., the biologically active form of the molecule), because they do not bind to most other inactive forms of hCG in the circulation, and because they are neutralizing, immunogens that can be recognized by these antibodies with high affinity (i.e., $Ka>5\times10^{7}M^{1}$) will elicit the formation of neutralizing antibodies to hCG. Portions of the β-subunit that should be preferentially retained in this immunogen include residues 43–53 and 91–92. In addition, other useful template antibodies are HCZ107 and HCO514 available from Hybritech, San Diego, Calif. These antibodies bind to both hCG and its free β-subunit with high affinity and neutralize the activity of the hormone. Both have low affinity for hLH. Residues critical for the interaction of HCZ107 with hCG include those near 114 and residues critical for the interaction of HCO514 with hCG include those near 77.

Example 8

Enhancement of Immunological Activity

During active immunization against LH or chorionic gonadotropin one is creating a site-directed autoimmune response. Thus, it is essential to use proteins that are highly antigenic. This can be facilitated by using the template/exclusion approach described in example 6 to make the immunogen as foreign as possible. In addition, it is desirable to make the molecule multivalent to increase the chances that it will interact with the immune system. One good method to make the molecule multivalent is to add residues to either the C-terminus or the N-terminus that will cause the formation of an α-helix that can form a coiled-coil with other molecules. The rules for designing peptide sequences that form coiled coils are well-known in the art (60,61). In addition, it is also possible to use naturally occuring sequences from proteins known to form coiled-coils such as those found in the hemagglutinin protein of influenza virus, laminin, GCN4, or any of several other proteins. It is also possible to add residues to the C-terminus or the N-terminus that will result in the formation of a triple helix similar to that found in collagen. These triple helices will enable three or more molecules of antigen to combine. Other strategies for increasing the antigenicity of the immunogen can also be employed including coupling the immunogens end-to-end to make a polyprotein. As outlined (FIG. 5) it is possible to design a protein having any number of repeating units using this strategy.

The preferred antibodies that give a non-neutralizing inhibition of LH activity usually interact with the free β-subunit and the heterodimer well. Thus, in preparing immunogens to elicit the formation of these antibodies it is usually convenient to start with the free β-subunit. In contrast, many preferred antibodies that give a neutralizing inhibition of hCG activity bind the α, β-heterodimer better than the free hCG β-subunit. To elicit the formation of these antibodies, it is often useful to start with an immunogen that is a fusion protein prepared by coupling the C-terminus of the peptide comprised of the hCG β-subunit residues 1–114 to the N-terminus of a flexible protein linker composed of six repeating units of glycine and serine. The C-terminus of this fusion protein is then coupled to the N-terminus of the bovine α-subunit residues 1–96. This provides a single polypeptide that has the overall conformation of the β-subunit residues found in hCG and which can be used for immunization directly or which can be used as the starting compound in example 6. Administration of the antigen can be performed in any fashion that is well-known in the art. This includes injection, injection in adjuvants, and coupling the antigen to a virus.

Example 9

Reversal of the Effect of hCG

Vaccination of women with hCG to induce infertility has several desirable properties including 1) the antibodies will function only if fertilization has occurred, 2) the treatment will be long-term (i.e., occur for many menstrual cycles), and 3) the women will not need to take pills or have implants. In addition, the vaccination will be reversible using progestins that are known to prevent rejection of the fetus by the uterus. These include many progestational compounds such as dydrogesterone (62). This compound is commercially available from Solvay Pharmaceuticals, 901 Sawyer Road, Marietta, Ga., and has the desired property of not crossreacting with progesterone in immunoassays. Thus, treatment with dydrogesterone does not prevent accurate measurement of progesterone levels. Women who are actively immunized against hCG will continue to have normal menstrual cycles and should ovulate at the expected time during the midpoints of their menstrual cycle. In the procedure for inducing fertility, it is desirable to know when ovulation has occurred. However, it can also be assumed that it has occurred by day 18 of the menstrual cycle. At ovulation, progesterone is produced by the corpus luteum under the influence of LH. The progesterone causes the increase in the basal body temperature that is associated with ovulation and is a known method of monitoring ovulation. Another method for monitoring the LH surge is to measure LH in urine using one of the over the counter ovulation detection kits. After day 20 the woman desiring to become pregnant begins taking dydrogesterone (3–6 mg three times a day) and 0.625–1.25 mg Premarin (Ayerst Limited, New York, N.Y.). This is sufficient to mimic the secretion of luteal progesterone that would be caused by hCG if it were not neutralized as the result of vaccination. Dydrogesterone treatment is continued to prevent menses for 6 weeks. At that time dydrogesterone therapy is terminated. If serum progesterone levels are low, pregnancy has not occurred, menses will ensue, and another attempt at pregnancy can be made. If serum progesterone levels are high, progesterone levels will be high due to pregnancy and placental production of progesterone. Termination of dydrogesterone will not halt the pregnancy. The serum level of progesterone can also be monitored using standard radioimmunoassay techniques.

Example 10

Suppression of Male Fertility by Vaccination with FSH

Immunoneutralization of FSH has been shown to block fertility in monkeys and would be expected to block fertility in men (8). It has been extremely difficult to develop a highly-specific hFSH vaccine capable of eliciting high titer neutralizing antibodies to FSH for use in any species due to the highly conserved nature of the FSH β-subunit. Methods that have been described for development of antibodies to hCG can also be applied for development of antibodies to hFSH. Thus, one starts with molecules in which hFSH β-subunit residues 1–111 are substituted for hCG β-subunit residues 1–114 or 1–117. As a template antibody one can use FSG761 (Hybritech). Since neutralizing antibodies are desired, a preferred starting molecule will also contain the bovine β-subunit polypeptide coupled to the hFSH β-subunit polypeptide through a glycine-serine linker. The use of this vaccine in men will prevent fertility.

Example 11

Details of the Test Approach of the Present Invention for hCG

1. One obtains neutralizing antibodies either by making monoclonals or by purchasing them. One can also obtain neutralizing antisera by immunizing rabbits or other animals against hCG. It will also be useful to obtain antibodies or antisera against hLH.

2. These antibodies or antisera are used as positive and negative templates to screen libraries of hCG β-subunit mutants. These libraries can be made by random mutagenesis of the hCG β-subunit in particular regions of the molecule. Note that it is preferable to use an hCG β-subunit that is missing the C-terminus or that has a different sequence for this part of the molecule to avoid selecting for immunogens that are non-neutralizing. One convenient procedure involves the use of phage display techniques also listed below. However phage display is not essential for the technique to work.

3. The mutants are permitted to bind to the negative selection antibodies first. In the present example, namely development of an hCG vaccine, this would involve binding to the antibodies to LH or the antisera to LH to remove mutants that are structurally identical to LH.

4. The mutants that did not bind to the negative selection antibodies are then permitted to bind to the positive selection antibodies, namely those that were made by hCG immunization. During the positive selection process, free hCG subunit is also added to eliminate antibodies that bind the free subunit and to limit the selection process for those antibodies that are dimer specific. The mutants that do not bind to the positive selection antibodies are discarded. In the case of phage expressed proteins, the phage are eluted from the positive selection antibodies and used to infect E. coli.

5. This process is repeated for several rounds to eliminate potential immunogens that are capable of binding to the hLH antibodies and to further exclude those that have low affinity for hCG antibodies. The DNA sequences encoding the immunogens are sequenced. Immunogens that differ the most from hCG yet retain the ability to bind to hCG specific antibodies or antisera with high affinity are used further.

6. If needed, a second round of mutagenesis is performed to increase the number of differences between the potential immunogen and hCG. The goal is to devise an immunogen that differs from hLH and as much as possible from hCG yet retains the key-aspects of hCG structure that enable it to elicit high titer neutralizing antibodies. These include the regions of the β-subunit other than the C-terminus that differ most from hLH β-subunit.

7. Once the major unique antigenic determinants have been selected, the immunogen is made multivalent. There are several methods for accomplishing this. One is to fuse the determinant to a protein that itself is multivalent or that forms multimers (e.g., immunoglobulins). Another is to fuse residues to the protein that form coiled-coils and that will promote association. Where possible these are from natural proteins that are known to elicit an immune response (e.g., flu).

8.A. It is essential to get titers high against the intact hCG molecule if it is desired to prevent fertility. This may require combining hCG with a molecule that is similar to an β-subunit. The α-subunit of other mammalian glycoproteins is suitable as a starting material.

8.B. A molecule that is also a suitable starting point is one that has the desirable properties of being a single polypeptide and that retains the structure of the heterodimer. In this case, it is desirable to also make mutations in the portion of the molecule derived from the α-subunit.

8.C. The immunogens can be produced using any convenient method such as expression in E. coli, yeast, or mammalian cells. It is not required that the immunogens be glycosylated. The immunogens can also be DNA or RNA. They can also be integrated into the coats of viruses.

8.D. It is also not required to start with the hCG β-subunit. One can start with any protein. The key is to use the template strategy to select the proteins that one wants. For example, one can start with a four helix bundle and incorporate the amino acid sequences from portions of the hCG β-subunit that are near residues 38–57 and 91–92. One can also start with an immunoglobulin, including one that is an antiidiotypic monoclonal antibody to an hCG-specific antibody.

FIG. 1 is a graph illustrating the influence of antibodies and antisera on the binding of radiolabeled hLH to LH receptors. FIG. 1 illustrates the influence of three different types of antibodies or antisera on the binding of hLH to LH receptors. Antibody "A" has little or no effect on the binding of the hormone to receptors. Its main potential inhibitory influence in vivo would be on the metabolism of the hormone. Antibody "B" has the ability to partially block the binding of hLH to LH receptors. Thus, although the antibody would be inhibitory in vivo, even a very large excess of this antibody relative to LH would be unable to reduce its activity below 40% as shown here. Note that different antibodies can be produced that have different abilities to block the activities of LH (e.g., B105 and B110), Antibody "B" is an example of the general type of antibody that is most useful in vivo. Antibody "C" is a neutralizing antibody since at high concentrations it can prevent the activity of hLH. Due to its potential to prevent LH activity, an excess of this antibody would inhibit fertility.

FIG. 2 is a graph illustrating the influence of antibodies and antisera on the ability of hLH to induce steroidogenesis in vitro. FIG. 2 illustrates the effects of three antibodies on the ability of LH to induce testosterone synthesis (i.e., steroidogenesis) from rat testes Leydig cell suspensions. Curve "A" illustrates the ability of hLH to induce steroidogenesis in the absence of antibodies. Curve "B" illustrates the ability of hLH to induce steroidogenesis in the presence of a massive excess of antibody that can reduce hLH activity by approximately 3-fold. Curve "C" illustrates the ability of hLH to induce steroidogenesis in the presence of a massive excess of antibody that can reduce hLH activity by approximately 20-fold. Curve "D" illustrates the ability of hLH to induce steroidogenesis in the presence of a massive excess of antibody that can neutralize hLH activity. The decision to use antibody "B" and/or "C" in vivo will depend on the ratio of LH/FSH and the extent that one desires to suppress LH activity. When hLH levels are high and need to be reduced the most, antibody "C" would be preferred. When hLH/hFSH ratios are only slightly elevated, antibody "B" would be preferred. Use of antibody "D" at very high doses would result in infertility. It is anticipated that many useful antibodies will be found having the ability to reduce the activity of hLH or other LH on ovarian cells as well as testes cells.

FIG. 3 is a graph illustrating the influence of antibodies and antisera on the ability of hLH to induce steroidogenesis in vivo. FIG. 3 illustrates the effects of three different antibodies on testosterone formation in males when massive amounts of the antibodies are administered i.v. prior to different amounts of hLH also given i.v. In all the examples illustrated, the quantity of antibody administered greatly exceeds that of hLH on a molar basis. Similar effects would be expected for the antibodies on steroidogenesis in females. Curve "A" shows the effect of hLH on steroidogenesis in the absence of antibody. Curve "B" illustrates the effect of a massive amount of antibody which can inhibit the activity of hLH by 40% at most. Curve "C" illustrates the influence of a massive amount of antibody which can inhibit the activity of hLH by 95% at most. Curve "D" illustrates the effects of a massive amount of a neutralizing antibody.

FIG. 4 shows vectors that can be used in template/exclusion selection strategies. These vectors are similar in design as that described by Bass et al. (34) and are made by replacing the coding sequences for human growth hormone with those of the α-subunits of hLH or an hLH chimera using polymerase chain reaction mutagenesis procedures that are standard in the art such as the SOEing procedure described by Ho, et al. (63). Similar vectors for the generation of immunogens to hCG and hFSH could be made by replacing the growth hormone sequence with the coding sequences of the hCG β-subunit residues 1–114, hFSH β-subunit residues 1–111, the coding sequences of the hCG β-subunit residues 1–114 coupled 5' of the coding sequences for amino acids glycine-serine-glycine-serine-glycine-serine-glycine-serine-glycine-serine-glycine-serine-coupled 5' of the coding sequences for the bovine α-subunit, or the coding sequences of the hFSH β-subunit residues 1–111 coupled 5' of the coding sequences for amino acids glycine-serine-glycine-serine-glycine-serine-glycine-serine-glycine-serine-glycine-serine-coupled 5' of the coding sequences for the bovine α-subunit. In this Figure the "lac p" represents the lac promoter, stII represents the leader secquence, "hLH beta" represents the human LH beta subunit coding sequence from codon 1 to codon 114, "M13 gene III" represents the coding sequence of the M13 gene protein codons 198–410 in the same reading frame as the stII and human LH beta codons. "Amp resistance: is the gene from the pBR322 that encodes the β-lactamase enzyme, "322 ori" is the origin of replication from pBR322, and "fl ori" is the origin of replication from M13. Mutations would be made in the "hLH beta" portion of this vector. In addition, the "hLH beta" codons could be replaced with the codons for the other proteins described in the text.

Figure 5:
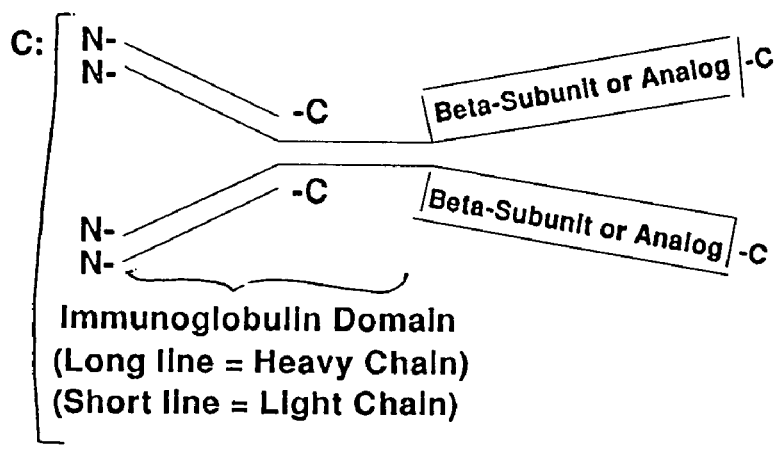
FIG. 5 shows the types of immunogens that have increased antigenicity for use in active immunization against LH, hCG, or FSH.
Figure 5:
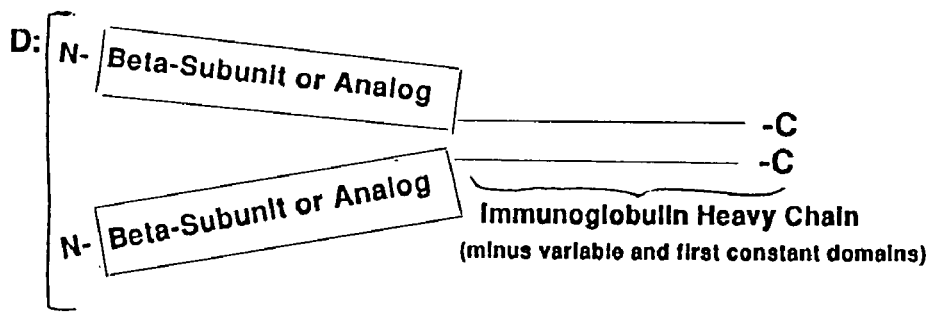

FIG. 5 shows the types of immunogens that have increased antigenicity for use in active immunization against LH, hCG, or FSH. Some of these have the heptad repeat known to form a coiled-coil (panel A). Others have a repeat known to form a triple helix (panel B). These give enhanced antigenicity because they are polymeric. Other methods of making polymeric immunogens include preparing fusion proteins with either the C-terminus (panel C) or the N-terminus of immunoglobulins (panel D). A single chain immunogen comprised of a fusion protein of the bovine α-subunit and the β-subunits of hCG and hFSH would have enhanced antigenicity in humans.

Illustration A: The codons for two or more heptad repeats are inserted in frame between codon 114 and the termination codon of the LH or analog subunit. Design of the heptad repeat is similar to that described in reference 60. Each repeat contains 7 amino acids labeled in order "A, B, C, D, E, F, G" that have the following properties. Amino acids a and d are hydrophobic and are leucine, isoleucine, or valine. Amino acids E and G are charged amino acids. Amino acid E should have the opposite charge as amino acid G to form homodimers. Thus if E is a glutamate, then G should be a lyslne. Amino acids "B,C,F" can be nearly any type that favors helix formation. Thus, they should contain few if any prolines or glycines.

Illustration B: The codons for 6 or more triplet amino acid repeats are inserted in frame between codon 114 and the termination codon of the β-unit. These triplets encode amino acids glycine, X, Y wherer X and Y are any amino acid known to be part of the collagen sequence that forms a triple helix.

Illustration C: The codons for the IgG heavy chain are inserted immediately 5' of codon 1 of the β-subunit. When these genes are co-expressed with lamda or kappa IgG light chain, they will cause the production of an IgG containing two β-subunits at its C-terminus.

Illustration D: The codons for the IgG heavy chain region lacking the variable and first constant region are inserted in frame between codon 114 and the termination codon of the β-subunit.

Illustration E: Codons for a glycine-serine repeat sequence (i.e., GS repeat) such as the sequence serine-glycine-serine-glycine-serine-glycine-serine-glycine-serine-glycine-glycine are inserted in frame between codon 114 and the termination codon of a β-subunit analog. The last codon of this analog becomes 126. Next, codons 1–96 for the bovine or other α-subunit or codons 1–92 of the human α-subunit are inserted in frame between codons 126 and the termination codon of the β-subunit construct containing the poly-glycine-serine tail. This forms a single subunit gonadotropin that conveys the structure of the glycoprotein hormone heterodimer.

Illustration F: Codons for the human, bovine, other vertebrate α-subunit, or analog sequence are added between the last codon and the termination codon of a gene coding for a heptad repeat containing only positively charged amino acids at positions E and G in the heptade repeat (i.e., Heptad repeat #1) using methods known to any expert skilled in standard recombinant DNA techniques for preparing and expressing genes. When this gene is expressed in bacterial, or yeast, or other eukaryotic cells or organisms it will produce a protein having the positively charged heptad repeat at its amino terminus and an α-subunit or α-subunit analog at its carboxy terminus. Codons for a heptad repeat encoding negatively charged amino acids at positions E and G (i.e., Heptad repeat #2) are added between the last codon and the termination codon for a β-subunit analog. When this gene is expressed in bacteria or yeast or other eukaryotic cells or organisms, it will produce a protein having a β-subunit or analog at its amino terminus and the negatively charged heptad repeat at its carboxy terminus.

Illustration G: This shows the heterodimer that is formed when the proteins having the form described in illustration F are mixed. The sequences of heptad repeat #1 and heptad repeat #2 are chosen to foster the formation of heterodimers and reduce the formation of homodimers.

Illustration H: Multimers are formed when the compounds in illustrations F and G are mixed due to the combination of the α- and β-subunits and the heptad repeats. In illustrations A–H, the "N-" and "—C" refer to the amino terminus and the carboxy terminus of the proteins. The "i" refers to a single unit that can be repeated several times. Note also that while the heptad repeats illustrated here are identical, use of identical repeats is not essential. There are large numbers of proteins that contain non-identical heptad repeats that are able to form homodimers or heterodimers (60).

Single Chain Gonadotropins with Lutropin and/or Folliotropin Activity

Example 12

Preparation and use of Analog #1 (c.f., Table 1), a Single Chain Gonadotropin with Lutropin Activity. (See FIG. 6)

The coding sequences for analog #1 listed in Table 1 can be synthesized using the block ligation approach described (54) or they can be prepared starting with the coding sequences for the hCG β-subunit and the human α-subunit. These can be cloned from a human placental cDNA library. The sequences encoding the signal peptide from the human α-subunit are deleted and the coding sequences for the proteins are spliced together using the SOEing technique (63) as follows: Primer #1 (100 ng) having the sequence 5'-ATGAAATCGACGGAATCAGACTCGAGC-CAAGGATGGAGATGTTCCAGGG GCTGCT-3' (SEQ ID NO:1) primer #2 (100 ng) having the sequence 3' (SEQ ID NO:2) GGGAGCCTGTGGGGCTAGGAGGGGGTTC-CTAGGCCATCGCCTAGACCAT CG-5' (SEQ ID NO:2) are mixed with the hCG β-subunit cDNA (1 μg) which serves as a template and PCR is performed for 25 temperature cycles of 94° C. (30 seconds), 50° C. (60 seconds), 72° C. (60 seconds) using Pfu DNA polymerase purchased from Strate-gene, LaJolla, Calif. and dioxynucleotide triphosphates and PCR buffer as described (63). Primer #3 (100 ng) having the sequence 5'-GGATCCGGTAGCGGATCTGG-TAGCGCTCCTGATGTGCAGGATGCCCA-3' (SEQ ID NO:3) and primer #4 (100 ng) having the sequence 3'-ACGTCATGAACAATAATAGTGTTTA-GAATTCCATGGCCTAGGTAGAGTTC GATTAGGCCT-5' (SEQ ID NO:4) are mixed with human α-subunit cDNA (1 μg) which serves as a template and PCR is performed for 25 temperature cycles of 94° C. (30 seconds), 50° C. (60 seconds), 72° C. (60 seconds) using Pfu DNA polymerase and dioxynucleotide triphosphates and PCR buffer as described (63). These two PCR reactions give products that serve as intermediate templates in a third (final) PCR reaction that gives the desired constructs in a form suitable for cloning. The final PCR reaction is performed by mixing 1 μl of the products from the first two PCR reactions along with primer #5 having the sequence 5'-ATGAAATCGACG-GAATCAGACTCGAGCCAAGG-3' (SEQ ID NO:5) and primer #6 having the sequence 3'-ATTCCATGGCCTAGG-TAGAGTTCGATTAGGCCT-5' for 25 temperature cycles of 94° C. (30 seconds), 50° C. (60 seconds), 72° C. (60 seconds) using Pfu DNA polymerase, additional dioxynucleotide triphosphates, and PCR buffer. The final PCR product is digested with restriction enzymes XhoI and BglII and ligated into pSVL (an expression vector obtained from Pharmacia, Piscataway, N.J.) that has been digested with XhoI and BamHI to create a vector that will direct the synthesis of Analog 1. The XhoI site of the PCR product will ligate to the XhoI site of pSVL and the BglII site of the PCR product will ligate to the BamHI site of pSVL. The XhoI site will be regenerated and the BglII and BamHI sites will be eliminated. The sequences of the coding regions (i.e., between the XbaI and KpnI sites, c.f., FIG. 6) of several constructs are determined until one is found that encodes a protein having the desired amino acid sequence illustrated in FIG. 6. This is done to eliminate the possible errors that arise as the result of PCR and other DNA manipulation and is a standard precaution to be certain that the desired sequence is obtained. The expressed protein is expected to lack amino acid residues MEMFQGLLLLLLLSMGGTWA (SEQ ID NO:20) that are the part of the signal sequence found in hCG β-subunit and which are removed by the cell during protein synthesis. This vector is expressed in COS-7 cells as described (64) and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), HCZ107 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog would also be expected to be a good starting point for use in a contraceptive vaccine using the template approach outlined in Example 11. This analog is shown in Table 1 as Analog #1 and contains a linker sequence of GSGSGSGS. This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the ApaI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 13

Preparation and use of Analog #2, a Single Chain Gonadotropin with Lutropin Activity. (See FIG. 7)

The coding sequences for Analog #2 listed in Table 1 can be synthesized using the block ligation approach described (54) or they can be prepared by PCR using primers #1 and #7 and the expression construct described in Example 12 and in FIG. 6 as a template. The sequence of primer is 3'-TGGTGGGGAACTGGACACTACTGGGCGC-CCCTAGGCCATCG-5' (SEQ ID NO:7). The final PCR product is digested with restriction enzymes XhoI and BamHI and ligated with the large fragment of DNA obtained by digesting the expression construct described in Example 12 with XhoI and BamHI. The sequences of the coding regions between the XhoI and BamHI sites of several constructs are determined until one is found that encodes a protein having the amino acid sequence described in FIG. 7 is obtained. This will insure that cloning artifacts are not present in the region that has been altered. The expressed protein is expected to lack amino acid residues MEM-FQGLLLLLLLSMGGTWA (SEQ ID NO:20) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog would also be expected to be a good starting point for use in a contraceptive vaccine using the template approach outlined in Example 11. This analog is shown in Table 1 as Analog #2 and contains a linker sequence of GSGSGSGS (SEQ ID NO:21) linker can be modified by digesting the expression vector with SstII and Eco47III endonuclease restriction enzymes, discarding the short piece, ligating a cassette of synthetic double stranded DNA with the desired amino acid codons containing any number of glycine or serine codons or other amino acid codons into the SstII/Eco47III site by standard methods, sequencing the region between the SstII/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 14

Preparation and use of Analog #3, a Single Chain Gonadotropin with Lutropin Activity. (See FIG. 8)

The coding sequences for analog #3 listed in Table 1 can be synthesized using the block ligation approach described (54) or they can be prepared in the fashion as described for Analog #2 in Example 13 except that primers #1 and #7 are replaced with primers #8 and #9 and that the hLH β-subunit cDNA is used as a template in place of the hCG β-subunit cDNA. The hLH β-subunit cDNA can be obtained by screening a human pituitary library. The sequence of primer #8 is 5'-ATGAAATCGACGGAATCGACTCGAGC-CAAGGAATGGAGATGCTCCAGG GGCTGCT-3' (SEQ ID NO:8) and the sequence of primer #9 is 3'-GTGGG-GAACTGGACACTGGTGGGGGTTCCTAG-GCCATCGCCTAGACCATC G-5'. The final PCR product is digested with restriction enzymes XhoI and BamHI and subcloned into the XhoI/BamHI sites of the expression vector created as described in Example 12. The sequences of the coding regions between the XhoI and BamHI sites of several constructs are determined until one is found that encodes a protein having the amino acid sequence shown in FIG. 8. The expressed protein is expected to lack amino acid residues MEMLQGLLLLLLLSMGGAWA (SEQ ID NO:22) that are the part of the signal sequence found in hLH β-subunit and which are removed by the cell during protein synthesis. This vector is expressed in COS-7 cells and the protein released into the medium is tested for its ability to inhibit the binding of radioiodinated hCG to monoclonal antibodies or to an antisera prepared against hCG. The protein made by the COS-7 cells will compete with radioiodinated hCG for binding to one or more of the following antibodies: B101 (obtained from Columbia University), B105 (obtained from Columbia University), A201 (obtained from Columbia University), HCU061 (obtained from Hybritech), ZMCG7 (obtained from Pierce) or 518B7 (obtained from Dr. Janet Roser, University of California at Davis). The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog would also be expected to be a good starting point for use in designing vaccines to enhance or inhibit fertility using the template procedure outlined earlier. This analog is shown in Table 1 as Analog #3 and contains a linker sequence of GSGSGSGS (SEQ ID NO:21). This linker can be modified by digesting the expression vector with BamHI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the BamHI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 15

Preparation and use of Analog #4, a Single Chain Gonadotropin with Follitropin Activity.
(See FIG. 9)

The coding sequences for analog #4 listed in Table 1 can be synthesized using the block ligation approach described (54) or they can be prepared in the fashion as described for Analog #2 in Example 13 except that primers #1 and #7 are replaced with primers #10 and #11 and that the hFSH β-subunit cDNA is used as a template in place of the hCG β-subunit cDNA. The hFSH β-subunit cDNA can be obtained from a human pituitary gland library. The sequence of primer #10 is 5'-ATGAAATCGAGATCGACTCGAGC-CAAGGATGAAGACACTCCAGTT TTTCTTCC-3 (SEQ ID NO:10) and the sequence of primer #11 is 3'-GACGAG-GAAACCACTTTACTTTCTTCCTAGGC-CATCGCCTAGACCA-5' (SEQ ID NO:11) The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 9. The expressed protein is expected to lack amino acid residues MKTLQFFFLFCCW-KAIC that are the part of the signal sequence found in hFSH β-subunit and which are removed by the cell during protein synthesis. The vector is expressed in COS-7 cells and the protein made by the cells will compete with radioiodinated hFSH for binding to one or more of the following antibodies: ZMFS1 (obtained from Pierce), A201 (obtained from Columbia University), HCU061 (obtained from Hybritech), FSG761 (obtained from Hybritech), FSR093.3 (obtained from Hybritech), FSH107 (obtained from Hybritech), FSB061 (obtained from Hybritech), FSM210 (obtained from Hybritech), and FSM268 (obtained from Hybritech). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is also a useful starting compound to select for an immunogen that elicits antibodies to FSH and is part of a contraceptive vaccine. This analog is shown in Table 1 as Analog #4 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 16

Preparation and use of Analog #5, a Single Chain Gonadotropin with FSH Activity that is Structurally more Similar to hCG than hFSH. (See FIG. 10)

The coding sequences for analog #5 listed in Table 1 can be synthesized using the block ligation approach described (54) or they can be prepared in the fashion as described for Analog #2 in Example 13 except that primer #7 is replaced with primer #12. The sequence of primer #12 is 3'-CGA-CAGTCGACAGTTACACGTGAGACGCTGTCGCTGT-CGTGACTAACATG ACACGCTCCGGACCCCGGGTC-GATGACGAGGAAACCACTTTACTTTCTTC CTAGGC-CATCG-5' (SEQ ID NO:12). The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 10. The expressed protein is expected to lack amino acid residues MEMLQGLLLLLLLSMGGAWA (SEQ ID NO:22) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with HFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is shown in Table 1 as Analog #5 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 17

Preparation and use of Analog #6, a Single Chain Gonadotropin with FSH and LH Activities that is Structurally more Similar to hCG than hFSH.
(See FIG. 11)

The coding sequences for analog #6 listed in Table 1 can be synthesized using the block ligation approach described (54) or they can be prepared in the fashion as described for Analog #2 in Example 13 except that primer #7 is replaced with primer #13. The sequence of primer #13 is 3'-ACG-GCGGCGTCGTGGTGACTGACGTGA-CACGCTCCGGACCCCGGGTCGA TGACGAG-GAAACCACTTTACTTTCTTCCTAGGCCATCG-5' (SEQ ID NO:13). The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 11. The expressed protein is expected to lack amino acid residues MEMLQGLLLLLLLSMGGAWA (SEQ ID NO:22) that are the part of the signal sequence found in hCG-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog is shown in Table 1 as Analog #6 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 18

Preparation and use of Analog #7, a Single Chain Gonadotropin with FSH and LH Activities that is Structurally more Similar to hCG than hFSH The coding sequences for analog #7 listed in Table 1 can be synthesized using the block ligation approach described (54) or they can be prepared in the fashion as described for Analog #2 in Example 13 except that primer #7 is replaced with primer #14. The sequence of primer #14 is 3'-ACG-GCGGCGTCGTGGTGACTGACGTGA-CACGCTCCGGACCCCGGGTCGA TGACGAG-GAAACCACTTCCTAGGCCATCG-5' (SEQ ID NO:14). The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 12. The expressed protein is expected to lack amino acid residues MEM-LQGLLLLLLLSMGGAWA (SEQ ID NO:22) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog is shown in Table 1 as Analog #17 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 19

Preparation and use of Analog #8, a Single Chain Gonadotropin with FSH and LH Activities that is Structurally more Similar to hCG than hFSH.
(See FIG. 13)

The coding sequences for analog #8 listed in Table 1 can be synthesized using the block ligation approach described (54) or they can be prepared in the fashion as described for Analog #2 in Example 13 except that primer #7 is replaced with primer #15. The sequence of primer #15 is 3'-ACG-GCGGCGTCGTGGTGACTGACGTGA-CACGCTCCGGACCCCGGGTCGA TGACGC-TACTGGGCGCCCCTAGGCCATCG-5' (SEQ ID NO:15). The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 13. The expressed protein is expected to lack amino acid residues MEM-LQGLLLLLLLSMGGAWA (SEQ ID NO:22) that are a part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog is shown in Table 1 as Analog #8 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 20

Preparation and use of Analog #9, a Single Chain Gonadotropin with Follitropin Activity.
(See FIG. 14)

The coding sequences for analog #9 listed in Table 1 can be synthesized using the block ligation approach described (54) or they can be prepared by digesting the construct described in Example 15 used to express Analog 4 with the restriction enzymes ApaI and BamHI. The small piece is replaced with a cassette of synthetic DNA to give the sequence illustrated in FIG. 14. The coding sequence between the ApaI and BamHI sites of several constructs is determined until one is found that encodes a protein having the amino acid sequence illustrated in FIG. 14. The expressed protein is expected to lack amino acid residues MKTLQFFFLFCCWKAICC (SEQ ID NO:23) that are the part of the signal sequence found in hFSH β-subunit and which are removed by the cell during protein synthesis. The vector is expressed in COS-7 cells and the protein made by the cells will compete with radioiodinated HFSH for binding to one or more of the following antibodies: ZMFS1 (obtained from Pierce), A201 (obtained from Columbia University), HCU061 (obtained from Hybritech), FSG761 (obtained from Hybritech), FSR093.3 (obtained from Hybritech), FSH107 (obtained from Hybritech), FSBO61 (obtained from Hybritech), FSM210 (obtained from Hybritech), and FSM268 (obtained from Hybritech). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is also a useful starting compound to select for an immunogen that elicits antibodies to FSH and is part of a contraceptive vaccine. This analog is shown in Table 1 as Analog #9 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 21

Preparation and use of Analog #10, a Single Chain Gonadotropin with Follitropin Activity.
(See FIG. 15)

The coding sequences for Analog #10 listed in Table 1 can be synthesized using the block ligation approach described (54) or they can be prepared by digesting the construct described in Example 15 used to express Analog 4 with the restriction enzymes ApaI and BamHI. The small piece is replaced with a cassette of synthetic DNA to give the sequence illustrated in FIG. 15. The coding sequence between the ApaI and BamHI sites of several constructs is determined until one is found that encodes a protein having the amino acid sequence illustrated in FIG. 15. The expressed protein is expected to lack amino acid residues MKTLQFFFLFCCWKAICC (SEQ ID NO:23) that are the part of the signal sequence found in hFSH β-subunit and which are removed by the cell during protein synthesis. The vector is expressed in COS-7 cells and the protein made by the cells will compete with radioiodinated hFSH for binding to one or more of the following antibodies: ZMFS1 (obtained from Pierce), A201 (obtained from Columbia University), HCU061 (obtained from Hybritech), FSG761 (obtained from Hybritech), FSR093.3 (obtained from Hybritech), FSH107 (obtained from Hybritech), FSBO61 (obtained from Hybritech), FSM210 (obtained from Hybritech), and FSM268 (obtained from Hybritech). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is also a useful starting compound to select for an immunogen that elicits antibodies to FSH and is part of a contraceptive vaccine. This analog is shown in Table 1 as Analog #10 and contains a linker sequence of GSGSGSGS (SEQ ID NO:21). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 22

Preparation of an α-Subunit Analog Lacking Glycosylation Sites. (See FIG. 16)

Analogs 1–10 are expected to contain 4 asparagine-linked oligosaccharides since they contain 4 sets of codons for the sequence Asparagine-X-Threonine/Serine where X is any amino acid except proline. Removal of the asparagine-linked oligosaccharides, particularly those of the α-subunit, has been shown to reduce hormone efficacy. The asparagine-linked glycosylation signals can be removed from the α-subunit portion of the single chain gonadotropins using PCR as described here. PCR primer 16 having the sequence: 5'-TGCTTCTCTAGAGCATATCCCACTCCACTAAGG-TCCAAGAAGACGATGTT GGTCCAAAAGCAAGT-CACCT-3' (SEQ ID NO:16) and PCR primer 17 having the sequence: 3'-CAAAGTTTCACCTCGTTGTGTGCCG-CACGGTGACGTCATGAACAATAATA GTGTTTA-GAATTCCATGGCCATG-5' (SEQ ID NO:17) are used in a PCR reaction with a the vector that is capable of directing the expression of Analog 1 and that was described in Example 12 and FIG. 6. After 25 cycles in the conditions described in Example 12, the PCR product and the expression vector are digested with XbaI and KpnI. The small fragment produced by digestion of the vector is discarded and the digested PCR product is ligated into the vector in its place. This produces an expression vector that encodes Analog 11, an analog that contains only 2 Asn-linked glycosylation signals but that is expected to retain its affinity for antibodies and antisera that bind to hCG. It is also expected to retain its affinity for LH receptors as shown by its ability to compete with hCG for binding to membranes from rat corpora lutea. However, it is expected to have a reduced ability to induce signal transduction, expecially when its ability to elicit cyclic AMP accumulation is tested (37). It is possible to create similar derivatives of Analogs 2–10 in which the oligosaccharides are removed from the portion of the protein derived from the α-subunit by digesting each of the expression vectors with BamHI and KpnI, discarding the smaller piece, and ligating the small BamHI/KpnI fragment obtained by digestion of Analog 11. Thus, Analog 2 would become Analog 12, Analog 3 would become Analog 13, Analog 4 would become Analog 14, Analog 5 would become Analog 15, Analog 6 would become Analog 16, Analog 7 would become Analog 17, Analog 8 would become Analog 18, Analog 9 would become Analog 19, and Analog 10 would become Analog 20. Note that it would also be possible to remove only one of the two glycosylation signals on the portion of the single chain gonadotropins derived from the α-subunit simply by changing the sequences of primers 16 and 17 during their synthesis and following the protocol outlined here. Each of these analogs would exhibit the same antibody and receptor binding as their precursors. They would have reduced efficacy and as a consequence, they would inhibit signal transduction. Analogs 11, 12, and 13 would reduce the activity of LH and would stimulate fertility when given in the early part of the follicular phase of the menstrual cycle. They would reduce the activity of hCG and would prevent fertility when administered near the time of expected menses.

Example 23

Preparation of Analog 1a Lacking Asparagine-Linked Oligosaccharides. (See FIGS. 17 and 18)

The efficacy of gonadotropins is proportional to their content of carbohydrates and while Analogs 11, 12, 13, 14, 15, 16, 17, 18, 19, and 20 have lower efficacy, it is possible to reduce their efficacy further by eliminating all oligosaccharide chains. The asparagine-linked oligosaccharide chains can be eliminated from Analog 11 by PCR SOEing (63) using primers 1 and 18 in one reaction and primers 2 and 19 in a second reaction. The expression vector for Analog 11 serves as a template in both reactions. The sequence of primer #18 is 5'-CGGGGTAGGTTCGGTGG-GACCGACACCTCTTCCTCCCGACGGGG-3' (SEQ ID NO:18) and the sequence of primer #19 is 3'-GTG- GAGAAGGAGGGCTGCCCCGTGTGCATCACCGTC-AACACCACCATC-5' (SEQ ID NO:19). After 25 temperature cycles at 94° C. (30 sec), 55° C. (60 sec), and 72° C. (60 sec), 1 µl of each PCR reaction is mixed with primer #5 and additional primer #2, new buffer, enzyme, and deoxynucleotide triphosphates. The reaction product after 25 additional cycles is cut with XhoI and BamHI and substituted for the original DNA found between the XhoI/BamHI sites of the vector encoding Analog 11. This is accomplished by digesting the vector with XhoI and BamHI, discarding the small fragment and then ligating the large fragment with the XhoI/BamHI digested PCR product. Several clones are subjected to DNA sequencing until the one encoding the analog outlined in FIG. 18 termed Analog 1a is obtained. When this is expressed in COS-7 cells, the protein that is made will be recognized by the same antibodies and antisera as Analog 1. Analog 1a will also bind to lutropin receptors but will have reduced efficacy relative to hCG. Thus, it will be useful for reducing the function of LH or hCG. When administered early in the follicular phase of the menstrual cycle, Analog 1a will reduce androgen synthesis. As a consequence, estradiol synthesis will decline, FSH levels will rise and fertility will be stimulated. Analog 1a will also be useful for inhibiting premature luteinization of the follicle. When administered in the luteal phase at about the time of expected menses, the analog will block the actions of hCG and serve as a menses inducer and an inhibitor of fertility. Analog 1a will also serve as a good starting compound to design vaccines using the template strategy described earlier.

Example 24

Preparation of other Gonadotropins Lacking Asparagine-Linked Oligosaccharides

The coding vectors for Analogs 2a, 5a, 6a, 7a, and 8a are readily prepared from Analog 1a and Analogs 12, 15, 16, 17, and 18. Analog 1a is digested with KpnI and MstII and the small fragment discarded. The large fragment is ligated separately to the small fragment prepared by KpnI-MstII digestion of the coding vectors for Analogs 12, 15, 16, 17, and 18. Analogs 2a, 5a, 6a, 7a, and 8a will bind the same antibodies and receptors as Analogs 2, 5, 6, 7, and 8, respectively. However, their abilities to elicit signal transduction will be reduced. Consequently, they will serve as inhibitors. Analog 2a will be effective primarily in blocking binding of hormones to LH receptors. Depending on the time that it is administered, Analog 2a will elicit fertility (i.e., when given early in the menstrual cycle) or will inhibit fertility (i.e., when given near the time of implantation or expected menses). In this regard Analogs 1a and 2a will have similar activities. Analog 5a will be effective primarily in blocking binding of hormones to FSH receptors. Analog 5a will be useful for suppressing hyperovarian stimulation. Analogs 6a, 7a, and 8a will be inhibitors of binding to LH and FSH receptors. These will be useful for suppressing hyperovarian stimulation and for blocking premature luteinization.

The coding vectors for Analogs 3a and 4a can be made by SOEing PCR (63) in which Analogs 13 and 14 serve as templates. The strategy for design of the primers is similar as that described for the preparation of primers used to modify the expression vector for Analog 1a. When Analogs 3a and 4a are expressed in COS-7 cells, the proteins that are made will be recognized by the same antibodies and antisera as Analogs 3 and 4, respectively. Analog 3a will be useful for inhibiting the activity of hormones that bind to LH receptors. As such it will stimulate fertility when given early in the follicular phase. Analog 4a will be useful for inhibiting the activity of FSH. Analog 3a will be useful as a starting molecule for designing the vaccine to be used to increase fertility using the template strategy and antibodies that are able to partially neutralize the activity of LH. Analog 3a will also be useful as a starting molecule for designing the vaccine to prevent fertility using the template strategy and antibodies that are able to neutralize LH activity. Antibody 4a will also be useful as a starting molecule for designing the anti-FSH vaccine described earlier using the template strategy.

The coding vectors for Analogs 9a and 10a can be prepared from the coding vector for Analog 4a. The coding vector for Analog 4a is digested with BalI and KpnI and the small fragment discarded. The small BalI-KpnI fragments from the coding vectors for analogs 19 and 20 are ligated separately with the large Analog 4a fragment to produce coding vectors for Analogs 9a and 10a. When produced in COS-7 cells, Analogs 9a and 10a will have similar antibody and FSH receptor binding specificities as Analogs 9 and 10. Analogs 9a and 10a will have lower efficacy and will inhibit the activity of FSH. Thus, they will be useful for reducing ovarian hyperstimulation. They will also be useful starting vectors for the design of anti-FSH vaccines using the template strategy.

Example 25

Typical Procedure for Introducing a Glycosylation Site in a Gonadotropin

Due to the positive influence of oligosaccharide residues on the stability of hormones in circulation, it is often useful to add extra oligosaccharide chains to the proteins. Addition of oligosaccharides can also be used to prevent unwanted antibody or receptor interactions. Surfaces of the protein that do not interact with receptors are useful places to add oligosaccharide chains that are to be used to stimulate hormone function. This can have a valuable effect in modulating the activities of single chain glycoprotein hormones or of modulating the activities of the α,β-heterodimeric glycoprotein hormones. For example, addition of a glycosylation signal to FSH β-subunit at residues 71–73 to cause the creation of an asparagine-linked oligosaccharide at residue 71 will lead to a hormone that has higher activity. Conversely, addition of a glycosylation residue in this region of the protein after the other glycosylations have been removed will enhance its inhibitory activity. Methods for performing the mutagenesis are standard in the art and range from total synthesis of the coding sequences by block ligation of synthetic oligonucleotides (54) to SOEing PCR (63). Several examples of mutagenesis by SOEing PCR have already been given.

Example 26

Use of Sequences Other than Those Derived from Human Subunits

Analogs 1–20, Analogs 1b–10b and, in particular, Analogs 1A–10a will serve as useful starting compounds for template directed vaccine design. For development of hormone-specific vaccines for use in humans, it is useful to make analogs similar to those listed in Table 1 with a nonhuman α-subunit in place of the human α-subunit. This is because the bovine α-subunit renders the proteins more dissimilar to the human hormones than the analogs listed in Table 1. The approach to designing single chain glycoprotein hormones is similar to that listed in Examples 12–21 except that the coding sequences for the nonhuman α-subunits are substituted for the human α-subunit sequences illustrated. Similarly, the glycosylation signals can be removed by altering the codons for asparagine or serine or threonine or inserting a proline between asparagine and the serine or threonine.

In addition, when using the template strategy to design immunogens it is often desirable to start with a nonhuman molecule that has little, if any affinity for the templates used in positive selection and to introduce residues that will result in selection. These analogs can be prepared by substituting the FSH, LH, or TSH subunit sequences from nonhuman sources in place of the human FSH, LH, and hCG sequences illustrated in Examples 12–25 and Table 1.

TABLE 1

Structures of Single Chain Gonadotropins

| Analog | Composition |
|---|---|
| 1 | n-hCGβ(1–145)-Linker-humanα(1–92)-c |
| 2 | n-hCGβ(1–114)-Linker-humanα(1–92)-c |
| 3 | n-hLHβ(1–114)-Linker-humanα(1–92)-c |
| 4 | n-hFSHβ(1–111)-Linker-humanα(1–92)-c |
| 5 | n-hCGβ(1–93)-hFSHβ(88–111)-Linker-humanα(1–92)-c |
| 6 | n-hCGβ(1–100)-hFSHβ(95–111)-Linker-humanα(1–92)-c |
| 7 | n-hCGβ(1–100)-hFSHβ(95–108)-Linker-humanα(1–92)-c |
| 8 | n-hCGβ(1–100)-hFSHβ(95–103)-DDPR-Linker-humanα(1–92)-c |
| 9 | n-hFSHβ(1–108)-Linker-humanα(1–92)-c |
| 10 | n-hFSHβ(1–104)-Linker-humanα(1–92)-c |
| 1a | n-bCGβ(1–145)[N13X,N30X]-Linker-humanα(1–92)[N52X,N78X]-c |
| 2a | n-hCGβ(1–114)[N13X,N30X]-Linker-humanα(1–92)[N52X,N78X]-c |
| 3a | n-hLHβ(1–114)[N30X]-Linker-humanα(1–92)[N52X,N78X]-c |
| 4a | n-hFSHβ(1–111)[N7X,N24X]-Linker-humanα(1–92)[N52X,N78X]-c |
| 5a | n-hCGβ(1–93)[N13X,N30X]-hFSHβ(88–111)-Linker-humanα(1–92)[N52X,N78X]-c |
| 6a | n-hCGβ(1–100)[N13X,N30X]-hFSHβ(95–111)-Linker-humanα1–92)[N52X,N78X]-c |
| 7a | n-hCGβ(1–100)[N13X,N30X]-hFSHβ(95–108)-Linker-humanα(1–92)[N52X,N78X]-c |
| 8a | n-hCGβ(1–100)[N13X,N30X]-hFSHβ(95–103)-DDPR-Linker-humanα(1–92)[N52X,N78X]-c |
| 9a | n-hFSHβ(1–108)-Linker-humanα(1–92)-[N52X,N78X]-c |
| 10a | n-hFSHβ(1–104)[N7X,N24X]-Linker-humanα(1–92)-c |
| 1b | n-hCGβ(1–145)[N13X,N30X,P78X,V79T]-Linker-humanα(1–92)[N52X,N78X]-c |
| 2b | n-hCGβ(1–114)[N13X,N30X,P78X,V79T]-Linker-humanα(1–92)[N52X,N78X]-c |
| 3b | n-hLHβ(1–114)[N30X,P78X,V79T]-Linker-humanα(1–92)[N52X,N78X]-c |
| 4b | n-hFSHβ(1–111)[N7X,N24X,D71N,L73T]-Linker-humanα(1–92)[N52X,N78X]-c |
| 5b | n-hCGβ(1–93)[N13X,N30X,P78X,V79T]-hFSHβ(88–111)-Linker-humanα(1–92)[N52X,N78X]-c |
| 6b | n-hCGβ(1–100)[N13X,N30X,P78X,V79T]-hFSHβ(95–111)-Linker-humanα(1–92)[N52X,N78X]-c |
| 7b | n-bCGβ(1–100)[N13X,N30X,P78X,V79T]-hFSHβ(95–108)-Linker-humanα(1–92)[N52X,N78X]-c |
| 8b | n-hCGβ(1–100)[N13X,N30X,P78X,V79T]-hFSHβ(95–103)-DDPR-Linker-humanα(1–92)[N52X,N78X]-c |
| 9b | n-hFSHβ(1–108)[N7X,N24X,D71N,L73T]-Linker-humanα(1–92)-[N52X,N78X]-c |
| 10b | n-hFSHβ(1–104)[N7X,N24X,D71N,L73T]-Linker-humanα(1–92)-[N52X,N78X]-c |

Definitions of the Letters and Sequences in Table 1

"n-" refers to the N-terminus of the protein.
"-c" refers to the C-terminus of the protein.
"hCGβ(1–145)" refers to the hCG β-subunit amino acid sequence residues 1–145:
SKEPLRPRCRPINATLAVEKEG-CPVCITVNTTICAGYCPTMTRVLQGVLPALP QVVCNYRDVRFESIRLPGCPRGVNPV-VSYAVALSCQCALCRRSTTDCGGPK DHPLTCD-DPRFQDSSSSKAPPPSLPSPSRLPGPSDTPILPQ (SEQ ID NO:25)

"hCGβ(1–114)" refers to the hCG β-subunit amino acid sequence residues 1–114:
SKEPLRPRCRPINATLAVEKEG-CPVCITVNTTICAGYCPTMTRVLQGVLPALP QVVCNYRDVRFESIRLPGCPRGVNPV-VSYAVALSCQCALCRRSTTDCGGPK DHPLTCDDPR (SEQ ID NO:26)

"hCGβ(1–93)" refers to the hCG β-subunit amino acid sequence residues 1–93:
SKEPLRPRCRPINATLAVEKEG-CPVCITVNTTICAGYCPTMTRVLQGVLPALP QVVCNYRDVRFESIRLPGCPRGVNPV-VSYAVALSCQCALC (SEQ ID NO:27)

"hLHβ(1–114)" refers to the hLH β-subunit amino acid sequence residues 1–114:
SREPLRPWCHPINAILAVEKEG-CPVCITVNTTICAGYCPTMMRVLQAVLPPLP QVVCTYRDVRFESIRLPGCPRGVDPVVS-FPVALSCRCGPCRRSTSDCGGPKD HPLTCDHPQ (SEQ ID NO:28)

"hFSHβ(1–111)" refers to the hFSH β-subunit amino acid sequence residues 1–111:
NSCELTNMAVEKEGCGFCITINTTW-CAGYCYTRDLVYKDPARPKIQKTCTF KELVY-ETVRVPGCAHHADSLYTYPVATQCH-CGKCDSDSTDCTVRGLGPSYC SFGEMKE (SEQ ID NO:29)

Definitions of the Letters and Sequences in Table 1
(Continued)

"hFSHβ(1–108)" refers to the hFSH β-subunit amino acid sequence residues 1–108:
NSCELTNIAVEKEGCGFCITINTFW-CAGYCYTRDLVYKDPARPKIQKTCTF KELVY-ETVRVPGCAHHADSLYTYPVATQCH-CGKCDSDSTDCTVRGLGPSYC SFGE (SEQ ID NO:30)

"hFSHβ(1–104)" refers to the hFSH β-subunit amino acid sequence residues 1–104:
NSCELTNMAVEKEGCGFCITINTTW-CAGYCYTRDLVYKDPARPKIQKTCTF KELVY-ETVRVPGCAHHADSLYTYPVATQCH-CGKCDSDSTDCTVRGLGPSYC (SEQ ID NO:31)

"hFSHβ(88–111)" refers to the hFSH β-subunit amino acid sequence residues 88–111:
DSDSTDCTVRGLGPSYCSFGEMKE (SEQ ID NO:32)

"hFSHβ(95–111)" refers to the hFSH β-subunit amino acid sequence residues 95–111:
TVRGLGPSYCSFGEMKE (SEQ ID NO:33)

"hFSHβ(95–108)" refers to the hFSH β-subunit amino acid sequence residues 95–108:
TVRGLGPSYCSFGE (SEQ ID NO:34)

"hFSHβ(95–103)" refers to the hFSH β-subunit amino acid sequence residues 95–103:
TVRGLGPSY (SEQ ID NO:35)
"N13X" refers to the substitution of glutamine or other amino acid for hCG β-subunit residue asparagine 13 and analogs
"N30X" refers to the substitution of glutamine or other amino acid for hCG or hLH β-subunit residue asparagine 30 and analogs Definitions of the Letters and Sequences in Table 1
(Continued)

"N52X" refers to the substitution of glutamine or other amino acid for human α-subunit residue asparagine 52 and analogs
"N78X" refers to the substitution of glutamine or other amino acid for human α-subunit residue asparagine 78 and analogs
"P78X" refers to the substitution of any amino acid except proline for proline 78 in the β-subunits of hCG or hLH and analogs
"V79T" refers to the substitution of threonine or serine for valine 79 in hCG or hLH β-subunits and analogs
"D71N" refers to the substitution of asparagine for aspartic acid 71 in hFSH β-subunits and analogs
"L73T" refers to the substitution of threonine or serine for leucine 73 in hFSH β-subunits and analogs
"humanα(1–92)" refers to the human α-subunit sequence residues 1–92
APDVQDCPECTLQENPFFSQPGAPILQC-MGCCFSRAYPTPLRSKKTMLVQKN VTSESTC-CVAKSYNRVTVMGGFKVENHTACHCSTCYYHKS (SEQ ID NO:36)
"Linker" refers to a sequence containing repeating glycine and serine amino acids such as GS (SEQ ID NO:37), GSGS (SEQ ID NO:38), GSGSGS (SEQ ID NO:39), GSGSGSGS (SEQ ID NO:21), GSGSGSGSGS (SEQ ID NO:40), or any other sequence of amino acids that permits the β- and α-subunit sequences of the single chain gonadotropin to form a complex in which the α- and β-subunit portions combine with the β- and α-subunit portions of the same or other molecule.
"DDPR" (SEQ ID NO:41) refers to the amino acid sequence Asparagine-Asparagine-Proline-Arginine Notes for Table 1

1. The order of the components from left to right in the table is the order in which the components occur in the protein from the amino-terminus to the carboxy-terminus.
2. Due to the high conservation of sequence in all vertebrate gonadotropins that can be seen from the alignment of their cysteine residues, single chain gonadotropins can be prepared by substitution of any homologous residues for the corresponding portions of the hCG, hLH, and hFSH β-subunits.
3. The sequence of the other vertebrate gonadotropin α-subunits can be substituted for humanα(1–92). This includes but is not limited to bovine α-subunit residues 1–96.
4. As shown, the order of the components has the sequences derived from the β-subunit amino-terminal of the sequences derived from the α-subunit. The order of the components in the table can be reversed such that the α-subunit sequences are amino-terminal of the β-subunit sequences.
5. The amino acid sequences are shown in the standard single letter code except as noted.
6. Coding sequences for all these analogs can be made by standard recombinant DNA methods that are well known in the art. One procedure for making these is that provided by Campbell et al. (54). They can be expressed in eukaryotic cells by methods well known in the art using vectors that have been designed for eukaryotic expression and that are available from InVitrogen, San Diego, Calif. Those that do not contain oligosaccharide chains can also be made in *E. coli* by methods well known in the art using vectors such as the pET vectors that can be obtained from Novagen.
7. The glycosylation sites at hCG β-subunit asparagines 13 and/or 30 can be destroyed by substitution of the asparagine as illustrated and/or by substitution of residues 14 and/or 31 with a proline and/or by substitution of residues 15 and/or 32 with any other amino acid other than serine or threonine.
8. The glycosylation site at hLH β-subunit asparagine 30 can be destroyed by substitution of the asparagine as illustrated and/or by substitution of residue 31 with a proline and/or by substitution of residue 32 with any other amino acid other than serine or threonine.
9. The glycosylation sites at human β-subunit asparagines 52 and/or 78 can be destroyed by substitution of the asparagine as illustrated and/or by substitution of residues 53 and/or 79 with a proline and/or by substitution of residues 54 and/or 80 with any other amino acid other than serine or threonine.
10. The glycosylation sites at nonhuman α-subunit asparagines 56 and/or 82 can be destroyed by substitution of the asparagine with any other amino acid and/or by substitution of residues 57 and/or 83 with a proline and/or by substitution of residues 58 and/or 84 with any other amino acid other than serine or threonine.

TABLE 2

Properties and uses of the analogs illustrated in Table 1.

| Analog | Activity | Use |
| --- | --- | --- |
| 1 | LH | Induce ovulation: Increase male fertility |
| 2 | LH | Induce ovulation: Increase male fertility |
| 3 | LH | Induce ovulation: Increase male fertility |
| 4 | FSH | Induce follicle development; Increase male fertility |
| 5 | FSH | Induce follicle development; Increase male fertility |
| 6 | FSH and LH | Induce follicle development; Increase male fertility |
| 7 | FSH and LH | Induce follicle development; Increase male fertility |
| 8 | FSH and LH | Induce follicle development; Increase male fertility |
| 9 | FSH | Induce follicle development; Increase male fertility |
| 10 | FSH | Induce follicle development; Increase male fertility |
| 1a | Anti-LH | *Facilitate ovulation; Terminate pregnancy; Reduce androgen secretion |
| 2a | Anti-LH | Facilitate ovulation; Terminate pregnancy; Reduce androgen ecretion |
| 3a | Anti-LH | *Facilitate ovulation; Terminate pregnancy; Reduce androgen secretion |
| 4a | Anti-FSH | Treat ovarian hyperstimulation; Reduce spermatogenesis |
| 5a | Anti-FSH | Treat ovarian hyperstimulation; Reduce spermatogenesis |
| 6a | Anti-FSH and Anti-LH | Treat ovarian hyperstimulation; Reduce spermatogenesis |
| 7a | Anti-FSH and Anti-LH | Treat ovarian hyperstimulation; Reduce spermatogenesis |

TABLE 2-continued

Properties and uses of the analogs illustrated in Table 1.

| Analog | Activity | Use |
|---|---|---|
| 8a | Anti-FSH and Anti-LH | Treat ovarian hyperstimulation; Reduce spermatogenesis |
| 9a | Anti-FSH | Treat ovarian hyperstimulation; Reduce spermatogenesis |
| 10a | Anti-FSH | Treat ovarian hyperstimulation; Reduce spermatogenesis |
| 1b | Anti-LH | *Facilitate ovulation; Terminate pregnancy; Reduce androgen secretion |
| 2b | Anti-LH | *Facilitate ovulation; Terminate pregnancy; Reduce androgen secretion |
| 3b | Anti-LH | *Facilitate ovulation; Terminate pregnancy; Reduce androgen secretion |
| 4b | Anti-FSH | Treat ovarian hyperstimulation; Reduce spermatogeneais |
| 5b | Anti-FSH | Treat ovarian hyperstimulation; Reduce spermatogenesis |
| 6b | Anti-FSH and Anti-LH | Treat ovarian hyperstimulation; Reduce spermatogenesis |
| 7b | Anti-FSH and Anti-LH | Treat ovarian hyperstimulation; Reduce spermatogenesis |
| 8b | Anti-FSH and Anti-LH | Treat ovarian hyperstimulation; Reduce spermatogenesis |
| 9b | Anti-FSH | Treat ovarian hyperstimulation; Reduce spermatogenesis |
| 10b | Anti-FSH | Treat ovarian hyperstimulation; Reduce spermatogenesis. |

The compounds of the present invention can be administered to mammals, e.g., animals or humans, in amounts effective to provide the desired therapeutic effect. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient.

Throughout this application, various publications have been referenced. The disclosures in these publications are incorporated herein by reference in order to more fully describe the state of the art.

Appendium of References

1. Pierce J G, Parsons T F (1981) Glycoprotein hormones: structure and function. Ann Rev Biochem 50:465–495.
2. Yen S S C, Jaffe R B (1986) Reproductive Endocrinology: Physiology, Pathophysiology and Clinical Management. W.B. Saunders, Philadelphia.
3. Moyle W R (1980) Biochemistry of gonadotropin receptors. In: Oxford Reviews of Reproductive Biology Volume 2, edited by Finn C A. Oxford University Press, New York, pp 123–204.
4. Hsuch A J W, Adashi E Y, Jones P B C, Welsh T H, Jr. (1984) Hormonal regulation of the differentiation of cultured ovarian granulosa cells. Endocr Rev 5:76–127.
5. Hodgen G D, Itskovitz J (1988) Recognition and maintenance of pregnancy. In: The physiology of reproduction, edited by Knobil E, Neill J D. Raven Press, New York, pp 1995–2021.
6. DiZerega G S, Hodgen G D (1981) Folliculogenesis in the primate ovarian cycle. Endocr Rev 2:27–49.
7. Vaishnav M Y, Moudgal N R (1991) Effect of specific FSH or LH deprivation on testicular function of the adult rat. Indian J Biochem Biophys 28:513–520.
8. Aravindan G R, Ravindranath N, Moudgal N R (1991) Use of DNA Flowcytometry in assessing gonadotropin regulation of spermatogenesis in monkeys. In: Perspectives in Primate Reproductive Biology, edited by Moudgal N R, Yoshinaga K, Rao A J, Adiga P R. Wiley Eastern Limited, New Delhi, pp 189–199.
9. Steinberger E (1971) Hormonal control of mammalian spermatogenesis. Physiol Rev 51:1–22.
10. Moudgal N R, Macdonald G J, Greep R O (1972) Role of endogenous primate LH in maintaining corpus luteum function of the monkey. J Clin Endocrinol Metab 35:113–116.
11. Moudgal N R (1976) Passive immunization with anti-gonadotropin antisera as a method of menstrual regulation in the primate. In: Immunization with hormones in reproduction research, edited by Nieschlag E. North-Holland, Amsterdam, pp 233.
12. Moudgal N R, Sairam M R. Mahoney J (1985) On the immunogenicity of the beta subunit of ovine luteinizing hormone (oLH beta) and equine chorionic gonadotropin (eCG) in the chimpanzee (Pan troglodytes): effect of antiserum on monkey cycle and early pregnancy. Am J Reprod Immunol Microbiol 8:120–124.
13. Moudgal N R, Macdonald G J, Greep R O (1971) Effects of HCG antiserum on ovulation and corpus luteum formation in the monkey (Macaca fascicularis). J Clin Endocrinol Metab 32:579–581.
14. Stevens V C (1990) Birth control vaccines and immunological approaches to the therapy of noninfectious diseases. Inf Dis Clin North Am 4:343–354.
15. Dunbar B S, Lo C, Powell J, Stevens V C (1989) Use of a synthetic peptide adjuvant for the immunization of baboons with denatured and deglycosylated pig zona pellucida glycoproteins. Fertil Steril 52:311–318.
16. Stevens V C (1986) Use of synthetic peptides as immunogens for developing a vaccine against human chorionic gonadotropin. Ciba Found Symp 119:200–225.
17. Moyle W R, Pressey A, Dean Emig D, Anderson D M, Demeter M, Lustbader J, Ehrlich P (1987) Detection of conformational changes in human chorionic gonadotropin upon binding to rat gonadal receptors. J Biol Chem 262: 16920–16926.
18. Singh 0, Rao L V, GaLir A, Sharma N C, Alam A, Talwar G P 99) Antibody response and characteristics of antibodies in women immunized with three contraceptive vaccines inducing antibodies against human chorionic gonadotropin. Fertil Steril 52:739–744.
19. Kumar S, Talwar G P, Biswas D K (1992) Necrosis and inhibition of growth of human lung tumor by anti-α-human chorionic gonadotropin antibody. JNCI 84:42–47.
20. Gaur A, Arunan K, Singh 0, Talwar G P (1990) Bypass by an alternate 'carrier' of acquired unresponsiveness to hCG upon repeated immunization with tetanus-conjugated vaccine. Int Immunol 2:151–155.
21. Hojo H, Ryan R J (1985) Monoclonal antibodies against human follicle-stimulating hormone. Endocrinology 117: 2428–2434.
22. Moyle W R, Ehrlich P H, Canfield R E (1982) Use of monoclonal antibodies to hCG subunits to examine the orientation of hCG in the hormone-receptor complex. Proc Natl Acad Sci USA 79:2245–2249.
23. Ryan R J, Keutmann H T, Charlesworth M C, McCormick D J, Milius R P, Calvo F O, Vutyavanich T (1987) Structure-function relationships of gonadotropins. Recent Prog Horm Res 43:383–429.
24. Keutmann H T, Charlesworth M C, Mason K A, Ostrea T, Johnson L, Ryan R J (1987) A receptor-binding region in human choriogonadotropin/lutropin beta subunit. Proc Natl Acad Sci USA 84:2038–2042.
25. Moyle W R, Dean Emig D M, Lustbader J V, Keutmann H T (1988) Identification of an epitope on the β-subunit of human chorionic gonadotropin (hCG) near the receptor binding site. ICSU Short Rep 8:116.
26. Moyle W R, Matzuk M M, Campbell R K, Cogliani E, Dean Emig D M, Krichevsky A, Barnett R W, Boime I (1990) Loation of residues that confer antibody binding specificity using human chorionic gonadotropin/luteinizing hormone beta subunit chimeras and mutants. J Biol Chem 265:8511–8518.
27. Krichevsky A, Birken S, O'Connor J, Bikel K, Schlatterer J, Yi C, Agosto G, Canfield R (1991) Development and characterization of a new, highly specific antibody to the human chorionic gonadotropin-beta fragment. Endocrinology 128:1255–1264.
28. Ehrlich P H, Moustafa Z A, Krichevsky A, Birken S, Armstrong E G, Canfield R E (1985) Characterization and relative orientation of epitopes for monoclonal antibodies and antisera to human chorionic gonadotropin. Am J Reprod Immunol Microbiol 8:48–54.
29. Matteri R L, Roser J F, Baldwin D M, Lipovetsky V, Papkoff H (1987) Characterization of a monoclonal antibody which detects luteinizing hormones from diverse mammalian species. Domest Anim Endocrinol 4:157–165.
30. Ehrlich P H, Moyle W R, Canfield R E (1983) Monoclonal antibodies to gonadotropin subunits. Methods Enzymol 50:638–655.
31. Moyle W R, Anderson D M, Macdonald G J, Armstrong E G (1988) Bioimmunoassay (BIA): A sandwich immunoassay scheme employing monoclonal antibodies and hormone receptors to quantify anaytes. J Receptor Res 8:419–436.
32. Fiedler R, Verbitskii M S (1990) Monoclonal antibodies to human chorionic gonadotropin and certain human and animal hormones of the adenohypophysis. Biomedical Science 1:251–255.
33. Winter G, Milstein C (1991) Man-made antibodies. Nature 349:293–299.
34. Bass S, Greene R, Wells J A (1990) Hormone phage: an enrichment method for variant proteins with altered binding properties. Proteins 8:309–314.
35. Barrett R W, Cwirla S E, Ackerman M S, Olson A M, Peters E A, Dower W J (1992) Selective enrichment and characterization of high affinity ligands from collections of random peptides on filamentous phage. Analytical Biochemistry 204:357–364.
36. Huse W D, Sastry L, Iverson S A, Kang. A S, Alting-Mees M, Burton D R, Benkovic S J, Lerner R A (1992) Generation of a large combinatorial library of the immunoglobulin repertoire in phage lambda. 1989 Biotechnology 24:517–523.
37. Moyle W R, Bahl O P, Marz L (1975) Role of the carbohydrate of human choriogonadotropin in the mechanism of hormone action. J Biol Chem 250:9163–9169.
38. Lesk A M, Tramontano A (1992) Antibody structure and structural predictions useful in guiding antibody engineering. In: Antibody engineering: a practical guide, edited by Borrebaeck C A K. W. H. Freeman and Co., New York, pp 1–38.
39. Cheetham J C (1992) Engineering antibody affinity. In: Antibody engineering: a practical guide, edited by Borrebaeck C A K. W. H. Freeman and Co., New York, pp 39–68.
40. Morrison S L, Johnson M J, Herzenberg L A, Oi V T (1984) Chimeric human antibody molecules: mouse antigen-binding domains with human constant regions. Proc Natl Acad Sci USA 81:6851–6855.
41. Newman R, Alberts J, Anderson D, Carner K, Heard C, Norton F, Raab R, Reff M, Shuey S, Hanna N (1992) "Primitization" of recombinant antibodies for immunotherapy of human diseases: a mccaque/human chimeric antibody against human CD4. Biotechnology 10: 1455–1460.
42. Danielsson L, Borrebaeck C A K (1992) Amplification of rearranged Ig variable region DNA from single cells. In: Antibody engineering: a practical guide, edited by Borrebaeck C A K. W. H. Freeman and Co., New York, pp 89–102.
43. Cruz R1, Anderson D M, Armstrong E G, Moyle W R (1987) Nonreceptor binding of human chorionic gonadotropin (hCG): detection of hCG or a related molecule bound to endometrial tissue during pregnancy using labeled monoclonal antibodies that bind to exposed epitopes on the hormone. J Clin Endocrinol Metab 64:433–440.
44. Moyle W R, Anderson D M, Macdonald G J, Armstrong E G (1988) Bioimmunoassay (BIA): a sandwich immunoassay scheme employing monoclonal antibodies and hormone receptors to quantify analytes. J Recept Res 8:419–436.
45. McFarland K C, Sprengel R, Phillips H S, Kohler M, Rosemblit N, Nikolics K, Segaloff D L, Seeburg P H (1989) Lutropin-choriogonadotropin receptor: an unusual member of the G protein-coupled receptor family. Science 245:494–499.
46. Jia X, Oikawa M, Bo M, Tanaka T, Ny T, Boime I, Hsuch A J W (1991) Expression of human luteinizing hormone (LH) receptor: Interaction with LH and chorionic gonadotropin from human but not equine, rat, and ovine species. Mol Endocrinol 5:759–768.
47. Loosfelt H, Misrahi M, Atger M, Salesse R, Vu Hai Luu Thi M T, Jolivet A, Guiochon Mantel A, Sar S, Jallal B, Garnier J, et al (1989) Cloning and sequencing of porcine LH-hCG receptor cDNA: variants lacking transmembrane domain. Science 245:525–528.
48. Maniatis T, Fritsch E F, Sambrook J (1989) Molecular cloning: a laboratory manual. Cold Sspring Harbor Laboratory, Cold Spring Harbor, N.Y.
49. Kriegler M (1990) Gene Transfer and Expression: A Laboratory Manual. Stockton Press, New York.
50. Cosowsky L N, Campbell R K, Papkoff H R, Moyle W R, Macdonald G J (1991) Use of hormone chimeras to identify the binding site for a monoclonal antibody which binds to a highly conserved site on mammalian LH and LH receptor complexes. Biol Reprod 44, Supplement #1:70.
51. Stevens V C (1990) Birth control vaccines and immunological approaches to the therapy of noninfectious diseases. Infect Dis Clin North Am 4:343–354.
52. Jones W R, Bradley J, Judd S J, Denholm E H, 1 ng RM, Mueller U W, Powell J, Griffin P D, Stevens V C (1988) Phase I clinical trial of a World Health Organisation birth control vaccine. Lancet 1: 1295–1298.
53. Bidart J M, Bellet D H, Alberici G F, Van Besien F, Bohuon C (1987) The immune response to a synthetic peptide analogous to the 109–145 beta hCG carboxyl-terminus is directed against two major and two minor regions. Mol Immunol 24:339–345.

54. Campbell R K, Erfle H, Barnett R W, Moyle W R (1992) Assembly and expression of a synthetic gene encoding the bovine glycoprotein hormone α-subunit. Mol Cell Endocrinol 83:195–200.
55. Lowman H B, Bass S H, Simpson N, Wells J A (1991) Selecting high-affinity binding proteins by monovalent phage display. Biochemistry 30:10832–10838.
56. Hoogenboom H R, Winter G (1992) By-passing immunisation. Human antibodies from synthetic repertoires of germline VH gene segments rearranged in vitro. J Mol Biol 227:381–388.
57. Fersht A, Winter G (1992) Protein engineering. Trends Biochem Sci 17:292–295.
58. Scott J K, Smith G P (1990) Searching for peptide ligands with an epitope library. Science 249:386–390.
59. Skerra A, Dreher M L, Winter G (1991) Filter screening of antibody Fab fragments secreted from individual bacterial colonies: specific detection of antigen binding with a two-membrane system. Anal Biochem 196:151–155.
60. Cohen, C. and Parry, D. A. D. (1990) α-Helical coiled coils and bundles: how to design an α-helical protein. Proteins: structure, function, and genetics 7: 1–15.
61. Hu, J. C., Newell, N. E., Tidor, B., and Sauer, R. T. (1993) Probing the roles of residues at the e and g positions of the GCN4 leucine zipper by combinatorial mutagenesis. Protein Science 2: 1072–1084.
62. King, R. J. B. and Whitehead, M. I. (1986j Assessment of the potency or orally administered progestins in women. Fertility and Sterility 46: 1062–1066.
63. Ho, S. N., Hunt, H. D., Horton, R. M., Pullen, J. K. and Pease, L. R. (1989) Site directed mutagenesis by overlap extension using the polymerase chain reaction. Gene 77: 51–59.
64. Campbell R K, Dean Emig D M, Moyle W R (1991) Conversion of human choriogonadotropin into a follitropin by protein engineering. Proc Natl Acad Sci USA 88:760–764
65. Skaf R, Macdonald G J, Sheldon R M, Moyle W R (1985) Use of antisera to follicle-stimulating hormone (FSH) to detect non-FSH factors in human serum which modulate rat granulosa cell steroidogenesis. Endocrinology 117:106–113

The invention being thus described, it will be obvious that the same may be varied in many ways. Such variations are not to be regarded as a departure from the spirit and scope of the invention and all such modifications are intended to be included within the scope of the following claims.

I claim:

1. A method for stimulating fertility in human females which comprises administering to the human female a therapeutically effective amount of an antibody or the portion of an antibody which retains the ability to bind to luteinizing hormone in serum and thereby reduces the biological activity of circulating luteinizing hormone.

2. The method according to claim 1, wherein the antibody or the portion of the antibody is a humanized antibody.

3. The method according to claim 1, wherein the antibody or the portion of the antibody binds to an epitope on the beta-subunit of luteinizing hormone at a position that remains exposed when luteinizing hormone binds to a luteinizing hormone receptor.

4. The method according to claim 3, wherein the antibody or the portion of the antibody binds one of the residues between positions 70–80 of the beta-subunit of luteinizing hormone.

5. The method according to claim 4, wherein the antibody or the portion of the antibody binds one of the residues between positions 74–77 of the beta-subunit of luteinizing hormone.

6. The method according to claim 1, wherein the antibody or the portion of the antibody is nonneutralizing and the method further comprises reducing but not eliminating the activity of luteinizing hormone.

7. The method according to claim 1, wherein the method comprises regulating ovulation in human females.

8. The method according to claim 6, wherein the nonneutralizing antibody or the portion of the antibody reduces the activity of luteinizing hormone 2–4 fold.

9. A method for stimulating fertility in human females by reducing the activity of luteinizing hormone in circulation, which comprises administering to the human female a therapeutically effective amount of an antibody or a portion of an antibody which binds to luteinizing hormone, thereby reducing the ability of a luteinizing hormone to interact with luteinizing hormone receptors.

10. A method for stimulating fertility in human females by reducing the activity of luteinizing hormone in circulation and thereby stimulating the production of follicle stimulating hormone, which comprises administering to the human female a therapeutically effective amount of an antibody or a portion of an antibody which binds to luteinizing hormone, thereby reducing the ability of a luteinizing hormone to interact with luteinizing hormone receptors.

11. The method according to claim 10, wherein the antibody or the portion of the antibody recognizes and epitope on luteinizing hormone that can be detected when luteinizing hormone is bound to the luteinizing hormone receptor.

* * * * *

SEQUENCE LISTING

```
<160> NUMBER OF SEQ ID NOS: 39

<210> SEQ ID NO 1
<211> LENGTH: 265
<212> TYPE: PRT
<213> ORGANISM: Rat leukemia virus

<400> SEQUENCE: 1

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
        50                  55                  60

Leu Gln Gly Val Leu Arg Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Gly Ser Ala Pro Asp
                165                 170                 175

Val Gln Asp Cys Pro Glu Cys Thr Leu Gln Glu Asn Pro Phe Phe Ser
                180                 185                 190
```

```
Gln Pro Gly Ala Pro Ile Leu Gln Cys Met Gly Cys Cys Phe Ser Arg
            195                 200                 205
Ala Tyr Pro Thr Pro Leu Arg Ser Lys Lys Thr Met Leu Val Gln Lys
        210                 215                 220
Asn Val Thr Ser Glu Ser Thr Cys Cys Val Ala Lys Ser Tyr Asn Arg
225                 230                 235                 240
Val Thr Val Met Gly Gly Phe Lys Val Glu Asn His Thr Ala Cys His
                245                 250                 255
Cys Ser Thr Cys Tyr Tyr His Lys Ser
            260                 265

<210> SEQ ID NO 2
<211> LENGTH: 836
<212> TYPE: DNA
<213> ORGANISM: Rat leukemia virus

<400> SEQUENCE: 2
```

| | | | | | |
|---|---|---|---|---|---|
| atgaaatcga | cggaatcaga | ctcgagccaa | ggatggagat | gttccagggg | ctgctgctgt | 60 |
| tgctgctgct | gagcatgggc | gggacatggg | catccaagga | gccgcttcgg | ccacggtgcc | 120 |
| gccccatcaa | tgccaccctg | ctgtggagaa | ggagggctg | ccccgtgtgc | atcaccgtca | 180 |
| acaccaccat | ctgtgccggc | tactgcccca | ccatgacccg | cgtgctgcag | ggggtcctgc | 240 |
| cggccctgcc | tcaggtggtg | tgcaactacc | gcgatgtgcg | cttcgagtcc | atccggctcc | 300 |
| ctggctgccc | gcgcgcgtg | aaccccgtgg | tctcctacgc | cgtggctctc | agctgtcaat | 360 |
| gtgcactctg | ccgccgcagc | accactgact | gcggggtcc | caaggaccac | cccttgacct | 420 |
| gtgatgaccc | ccgcttccag | gactcctctt | cctcaaaggc | cctcccccc | agccttccaa | 480 |
| gcccatcccg | actcccgggg | ccctcggaca | ccccgatcct | cccccaagga | tccggtagcg | 540 |
| gatctggtag | cgctcctgat | gtgcaggatt | gcccagaatg | cacgctacag | gaaaacccat | 600 |
| tcttctccca | gccgggtgcc | ccaatacttc | agtgcatggg | ctgctgcttc | tctagagcat | 660 |
| atcccactcc | actaaggtcc | aagaagacga | tgttggtcca | aaagaacgtc | acctcagagt | 720 |
| ccacttgctg | tgtagctaaa | tcatataaca | gggtcacagt | aatgggggt | ttcaaagtgg | 780 |
| agaaccacac | ggcgtgccac | tgcagtactt | gttattatca | caaatcttaa | ggtacc | 836 |

```
<210> SEQ ID NO 3
<211> LENGTH: 834
<212> TYPE: DNA
<213> ORGANISM: Rat leukemia virus

<400> SEQUENCE: 3
```

| | | | | | |
|---|---|---|---|---|---|
| ggttcctacc | tctacaaggt | ccccgacgac | gacaacgacg | acgactcgta | cccgccctgt | 60 |
| acccgtaggt | tcctcggcga | agccggtgcc | acggcggggt | agttacggtg | ggaccgacac | 120 |
| ctcttcctcc | cgacggggca | cacgtagtgg | cagttgtggt | ggtagacacg | gccgatgacg | 180 |
| gggtggatct | gggcgcacga | cgtcccccag | gacggccggg | acggagtcca | ccacacgttg | 240 |
| atggcgctac | acgcgaagct | caggtaggcc | gagggaccga | cgggcgcgcc | gcacttgggg | 300 |
| caccagagga | tgcggcaccg | acagtcgaca | gttacacgtg | agacggcggc | gtcgtggtga | 360 |
| ctgacgcccc | cagggttcct | ggtggggaac | tggacactac | tggggcgaa | ggtcctgagg | 420 |
| agaaggagtt | tccggggagg | ggggtcggaa | ggttcgggta | gggctgaggg | ccccgggagc | 480 |
| ctgtggggct | aggaggggggt | tcctaggcca | tcgcctagac | catcgcgagg | actacacgtc | 540 |
| ctaacgggtc | ttacgtgcga | tgtccttttg | ggtaagaaga | gggtcggccc | acggggttat | 600 |

-continued

| gaagtcacgt acccgacgac gaagagatct cgtataggt gaggtgattc caggttcttc | 660 |
| tgctacaacc aggttttctt gcagtggagt ctcaggtgaa cgacacatcg atttagtata | 720 |
| ttgtcccagt gtcattaccc cccaaagttt cacctcttgg tgtgccgcac ggtgacgtca | 780 |
| tgaacaataa tagtgtttag aattccatgg cctaggtaga gttcgattag gcct | 834 |

<210> SEQ ID NO 4
<211> LENGTH: 234
<212> TYPE: PRT
<213> ORGANISM: Rat leukemia virus

<400> SEQUENCE: 4

```
Met Glu Met Phe Gln Gly Leu Leu Leu Leu Leu Leu Ser Met Gly
1               5                   10                  15
Gly Thr Trp Ala Ser Lys Glu Pro Leu Arg Pro Arg Cys Pro Ile
            20                  25                  30
Asn Ala Thr Leu Ala Val Glu Lys Glu Gly Cys Pro Val Cys Ile Thr
            35                  40                  45
Val Asn Thr Thr Ile Cys Ala Gly Tyr Cys Pro Thr Met Thr Arg Val
50                  55                  60
Leu Gln Gly Val Leu Arg Ala Leu Pro Gln Val Val Cys Asn Tyr Arg
65                  70                  75                  80
Asp Val Arg Phe Glu Ser Ile Arg Leu Pro Gly Cys Pro Arg Gly Val
                85                  90                  95
Asn Pro Val Val Ser Tyr Ala Val Ala Leu Ser Cys Gln Cys Ala Leu
            100                 105                 110
Cys Arg Arg Ser Thr Thr Asp Cys Gly Gly Pro Lys Asp His Pro Leu
        115                 120                 125
Thr Cys Asp Asp Pro Arg Gly Ser Gly Ser Gly Ser Ala Pro
130                 135                 140
Asp Val Gln Asp Cys Pro Glu Cys Thr Leu Gln Glu Asn Pro Phe Phe
145                 150                 155                 160
Ser Gln Pro Gly Ala Pro Ile Leu Gln Cys Met Gly Cys Cys Phe Ser
                165                 170                 175
Arg Ala Tyr Pro Thr Pro Leu Arg Ser Lys Lys Thr Met Leu Val Gln
            180                 185                 190
Lys Asn Val Thr Ser Glu Ser Thr Cys Cys Val Ala Lys Ser Tyr Asn
        195                 200                 205
Arg Val Thr Val Met Gly Gly Phe Lys Val Glu Asn His Thr Ala Cys
210                 215                 220
His Cys Ser Thr Cys Tyr Tyr His Lys Ser
225                 230
```

<210> SEQ ID NO 5
<211> LENGTH: 743
<212> TYPE: DNA
<213> ORGANISM: Rat leukemia virus

<400> SEQUENCE: 5

| atgaaatcga cggaatcaga ctcgagccaa ggatggagat gttccagggg ctgctgctgt | 60 |
| tgctgctgct gagcatgggc gggacatggg catccaagga gccgcttcgg ccacggtgcc | 120 |
| gccccatcaa tgccaccctg ctgtggaga aggagggctg cccgtgtgc atcaccgtca | 180 |
| acaccaccat ctgtgccggc tactgcccca ccatgacccg cgtgctgcag ggggtcctgc | 240 |
| cggccctgcc tcaggtggtg tgcaactacc gcgatgtgcg cttcgagtcc atccggctcc | 300 |

```
ctggctgccc gcgcggcgtg aaccccgtgg tctcctacgc cgtggctctc agctgtcaat    360
gtgcactctg ccgccgcagc accactgact gcggggtcc caaggaccac cccttgacct    420
gtgatgaccc gcgggatcc ggtagcggat ctggtagcgc tcctgatgtg caggattgcc    480
cagaatgcac gctacaggaa aacccattct ctcccagcg gggtgcccca atacttcagt    540
gcatgggctg ctgcttctct agagcatatc ccactccact aaggtccaag aagacgatgt    600
tggtccaaaa gaacgtcacc tcagagtcca cttgctgtgt agctaaatca tataacaggg    660
tcacagtaat gggggtttc aaagtggaga accacacggc gtgccactgc agtacttgtt    720
attatcacaa atcttaaggt acc                                           743
```

<210> SEQ ID NO 6
<211> LENGTH: 717
<212> TYPE: DNA
<213> ORGANISM: Rat leukemia virus

<400> SEQUENCE: 6

```
ggttcctacc tctacaaggt ccccgacgac gacaacgacg acgactcgta cccgccctgt     60
acccgtaggt tcctcggcga agccggtgcc acggcggggt agttacggtg ggaccgacac    120
ctcttcctcc cgacggggca cacgtagtgg cagttgtggt ggtagacacg gccgatgacg    180
gggtggatct gggcgcacga cgtccccag gacggccggg acggagtcca ccacacgttg    240
atggcgctac acgcgaagct caggtaggcc gagggaccga cgggcgcgcc gcacttgggg    300
caccagagga tgcggcaccg acagtcgaca gttacacgtg agacggcggc gtcgtggtga    360
ctgacgcccc cagggttcct ggtggggaac tggacactac tgggcgcccc taggccatcg    420
cctagaccat cgcgaggact acacgtccta acgggtctta cgtgcgatgt ccttttgggt    480
aagaagaggg tcggcccacg gggttatgaa gtcacgtacc cgacgacgaa gagatctcgt    540
atagggtgag gtgattccag gttcttctgc tacaaccagg ttttcttgca gtggagtctc    600
aggtgaacga cacatcgatt tagtatattg tcccagtgtc attaccccccc aaagtttcac    660 ctcttggtgt gccgcacggt gacgtcatga acaataatag tgtttagaat tccatgg      717
```

<210> SEQ ID NO 7
<211> LENGTH: 234
<212> TYPE: PRT
<213> ORGANISM: Rat leukemia virus

<400> SEQUENCE: 7

```
Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125
```

-continued

```
Thr Cys Asp His Pro Gln Gly Ser Gly Ser Ser Gly Ser Ala Pro
            130                 135                 140
Asp Val Gln Asp Cys Pro Glu Cys Thr Leu Gln Glu Asn Pro Phe Phe
145                 150                 155                 160
Ser Gln Pro Gly Ala Pro Ile Leu Gln Cys Met Gly Cys Cys Phe Ser
                165                 170                 175
Arg Ala Tyr Pro Thr Pro Leu Arg Ser Lys Lys Thr Met Leu Val Gln
            180                 185                 190
Lys Asn Val Thr Ser Glu Ser Thr Cys Cys Val Ala Lys Ser Tyr Asn
        195                 200                 205
Arg Val Thr Val Met Gly Gly Phe Lys Val Glu Asn His Thr Ala Cys
    210                 215                 220
His Cys Ser Thr Cys Tyr Tyr His Lys Ser
225                 230
```

<210> SEQ ID NO 8
<211> LENGTH: 744
<212> TYPE: DNA
<213> ORGANISM: Rat leukemia virus

<400> SEQUENCE: 8

```
atgaaatcga cggaatcaga ctcgagccaa ggaatggaga tgctccaggg gctgctgctg      60
ttgctgctgc tgagcatggg cggggcatgg gcatccaggg agccgcttcg gccatggtgc     120
caccccatca atgccatcct ggctgtggag aaggagggct gccccgtgtg catcaccgtc     180
aacaccacca tctgtgccgg ctactgcccc accatgatgc gcgtgctgca ggcggtcctg     240
ccgcccctgc ctcaggtggt gtgcacctac cgtgatgtgc gcttcgagtc catccggctc     300
cctggctgcc cgcgtggcgt ggaccccgtg gtctccttcc ctgtggctct cagctgtcgc     360
tgtggacccct gccgccgcag cacctctgac tgtgggggtc ccaaagacca cccccttgacc    420
tgtgaccacc cccaaggatc cggtagcgga tctggtagcg ctcctgatgt gcaggattgc     480
ccagaatgca cgctcacagga aaacccattc ttctcccagc cgggtgcccc aatacttcag     540
tgcatgggct gcacgaagag atctcgtata gggtgaggtg attccaggtt cttctgctac     600
aaccaggttt tcttgcagtg gagtctcagg tgaacgacac atcgatttag tatattgtcc     660
cagacagtaa tgggggtttt caaagtggag aaccacacgg cgtgccactg cagtacttgt     720
tattatcaca aatcttaagg tacc                                            744
```

<210> SEQ ID NO 9
<211> LENGTH: 718
<212> TYPE: DNA
<213> ORGANISM: Rat leukemia virus

<400> SEQUENCE: 9

```
ggttccttac ctctacgagg tccccgacga cgacaacgac gacgactcgt acccgccccg      60
tacccgtagg tccctcggcg aagccggtac cacggtgggg atgttacggt aggaccgaca     120
cctcttcctc ccgacgggcg cacgtagtgc cagttgtgtg gtagacacac ggccgatgac     180
ggggtggtac tacgcgcacg acgtccgcca ggacggcggg acggagtcc accacacgtg     240
gatggcacta cacgcgaagc tcaggtaggc gagggaccg acgggcgcac cgcacctggg     300
gcaccagagg aagggacacc gagagtcgac agcgacacct gggacggcgg cgtcgtggag     360
actgacaccc ccaggttttc tggtggggaa ctggacactg gtgggggttc ctaggccatc     420
gcctagacca tcgcgaggac tacacgtcct aacgggtctt acgtgcgatg tccttttggg     480
```

-continued

| | |
|---|---|
| taagaagagg gtcggcccac ggggttatga agtcacgtac ccgacgacga agagatctcg | 540 |
| tataggggtga ggtgattcca ggttcttctg ctacaaccag gttttcttgc agtggagtct | 600 |
| caggtgaacg acacatcgat ttagtatatt gtcccagtgt cattaccccc caaagtttca | 660 |
| cctcttggtg tgccgcacgg tgacgtcatg aacaataata gtgtttagaa ttccatgg | 718 |

<210> SEQ ID NO 10
<211> LENGTH: 229
<212> TYPE: PRT
<213> ORGANISM: Rat leukemia virus

<400> SEQUENCE: 10

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Gly Ser Gly Ser Gly Ser Gly Ser Ala Pro Asp Val Gln Asp Cys
    130                 135                 140

Pro Glu Cys Thr Leu Gln Glu Asn Pro Phe Phe Ser Gln Pro Gly Ala
145                 150                 155                 160

Pro Ile Leu Gln Cys Met Gly Cys Cys Phe Ser Arg Ala Tyr Pro Thr
                165                 170                 175

Pro Leu Arg Ser Lys Lys Thr Met Leu Val Gln Lys Asn Val Thr Ser
            180                 185                 190

Glu Ser Thr Cys Cys Val Ala Lys Ser Tyr Asn Arg Val Thr Val Met
        195                 200                 205

Gly Gly Phe Lys Val Glu Asn His Thr Ala Cys His Cys Ser Thr Cys
    210                 215                 220

Tyr Tyr His Lys Ser
225
```

<210> SEQ ID NO 11
<211> LENGTH: 728
<212> TYPE: DNA
<213> ORGANISM: Rat leukemia virus

<400> SEQUENCE: 11

| | |
|---|---|
| atgaaatcga cggaatcaga ctcgagccaa ggatgaagac actccagttt tcttcctttt | 60 |
| tctgttgctg gaaagcaatc tgctgcaata gctgtgagct gaccaacatc accattgcaa | 120 |
| tagagaaaga agaatgtcgt ttctgcataa gcatcaacac cacttggtgt gctggctact | 180 |
| gctacaccag ggatctggtg tataaggacc cagccagggg gttttaggtc ttttgtacat | 240 |
| ggaagttcct tgaccatata ctttgtcact ctcacgggcc gacacgagtg gtacgtctaa | 300 |

```
ggaacatatg tatgggtcac cggtgggtct gtcactgtgg caagtgtgac agcgacagca      360
ctgattgtac tgtgcgaggc ctggggccca gctactgctc ctttggtgaa atgaaagaag      420
gatccggtag cggatctggt agcgctcctg atgtgcagga ttgcccagaa tgcacgctac      480
aggaaaaccc attcttctcc cagccgggtg ccccaatact tcagtgcatg ggctgctgct      540
tctctagagc atatcccact ccactaaggt ccaagaagac gatgttggtc aaaagaacg       600 tcacctcaga gtccacttgc tgtgtagcta atcatataa cagggtcaca gtaatggggg       660
gtttcaaagt ggagaaccac acggcgtgcc actgcagtac ttgttattat cacaaatctt      720
aaggtacc                                                              728

<210> SEQ ID NO 12
<211> LENGTH: 702
<212> TYPE: DNA
<213> ORGANISM: Rat leukemia virus

<400> SEQUENCE: 12
ggttcctact tctgtgaggt caaaaagaag gaaaagacaa cgacctttcg ttagacgacg       60
ttatcgacac tcgactggtt gtagtggtaa cgttatctct ttcttcttac agcaaagacg      120
taggcgtagt tgtggtgaac cacacgaccg atgacgatgt ggtccctaga ccacatattc      180
ctgggtcggt ccgggtttta ggtcttttgt acatggaagt tccttgacca tatactttgt      240
cactctcacg ggccgacacg agtggtacgc taaggaaca tatgtatggg tcaccggtgg       300
gtcacagtga caccgttcac actgtcgctg tcgtgactaa catgacacgc tccggacccc      360
gggtcgatga cgaggaaacc actttacttt cttcctaggc catcgcctag accatcgcga      420
ggactacacg tcctaacggg tcttacgtgc gatgtccttt tgggtaagaa gagggtcggc      480
ccacggggtt atgaagtcac gtacccgacg acgaagagat ctcgtatagg gtgaggtgat      540
tccaggttct tctgctacaa ccaggttttc ttgcagtgga gtctcaggtg aacgacacat      600
cgatttagta tattgtccca gtgtcattac cccccaaagt ttcacctctt ggtgtgccgc      660
acggtgacgt catgaacaat aatagtgttt agaattccat gg                        702

<210> SEQ ID NO 13
<211> LENGTH: 237
<212> TYPE: PRT
<213> ORGANISM: Rat leukemia virus

<400> SEQUENCE: 13

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Arg Ala Leu Pro Gln Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Asp Ser Asp Ser Thr Asp Cys Thr Val Arg Gly Leu Gly Pro Ser
```

```
            115                 120                 125
Tyr Cys Ser Phe Gly Glu Met Lys Glu Gly Ser Gly Ser Gly
        130                 135                 140

Ser Ala Pro Asp Val Gln Asp Cys Pro Glu Cys Thr Leu Gln Glu Asn
145                 150                 155                 160

Pro Phe Phe Ser Gln Pro Gly Ala Pro Ile Leu Gln Cys Met Gly Cys
                165                 170                 175

Cys Phe Ser Arg Ala Tyr Pro Thr Pro Leu Arg Ser Lys Lys Thr Met
                180                 185                 190

Leu Val Gln Lys Asn Val Thr Ser Glu Ser Thr Cys Cys Val Ala Lys
            195                 200                 205

Ser Tyr Asn Arg Val Thr Val Met Gly Gly Phe Lys Val Glu Asn His
    210                 215                 220

Thr Ala Cys His Cys Ser Thr Cys Tyr Tyr His Lys Ser
225                 230                 235
```

```
<210> SEQ ID NO 14
<211> LENGTH: 752
<212> TYPE: DNA
<213> ORGANISM: Rat leukemia virus

<400> SEQUENCE: 14
atgaaatcga cggaatcaga ctcgagccaa ggatggagat gttccagggg ctgctgctgt    60
tgctgctgct gagcatgggc gggacatggg catccaagga gccgcttcgg ccacggtgcc   120
gccccatcaa tgccaccctg ctgtggaga aggagggctg ccccgtgtgc atcaccgtca    180
acaccaccat ctgtgccggc tactgcccca ccatgacccg cgtgctgcag ggggtcctgc   240
cggccctgcc tcaggtggtg tgcaactacc gcgatgtgcg cttcgagtcc atccggctcc   300
ctggctgccc gcgcggcgtg aaccccgtgg tctcctacgc cgtggctctc agctgtcaat   360
gtgcactctg cgacagcgac agcactgatt gtactgtgcg aggcctgggg cccagctact   420
gctcctttgg tgaaatgaaa gaaggatccg gtagcggatc tggtagcgct cctgatgtgc   480
aggattgccc agaatgcacg ctacaggaaa acccattctt ctcccagccg ggtgccccaa   540
tacttcagtg catgggctgc tgcttctcta gagcatatcc cactccacta aggtccaaga   600
agacgatgtt ggtccaaaag aacgtcacct cagagtccac ttgctgtgta gctaaatcat   660
ataacagggt cacagtaatg gggggtttca agtggagaa ccacacggcg tgccactgca   720
gtacttgtta ttatcacaaa tcttaaggta cc                                 752

<210> SEQ ID NO 15
<211> LENGTH: 726
<212> TYPE: DNA
<213> ORGANISM: Rat leukemia virus

<400> SEQUENCE: 15
ggttcctacc tctacaaggt ccccgacgac gacaacgacg acgactcgta cccgccctgt    60
acccgtaggt tcctcggcga agccggtgcc acggcgggt agttacggtg ggaccgacac   120
ctcttcctcc cgacggggca cacgtagtgg cagttgtggt ggtagacacg gccgatgacg   180
gggtggatct gggcgcacga cgtcccccag gacggccggg acggagtcca ccacacgttg   240
atggcgctac acgcgaagct caggtaggcc gagggaccga cgggcgcgcc gcacttgggg   300
caccagagga tgcggcaccg acagtcgaca gttacacgtg agacgctgtc gctgtcgtga   360
ctaacatgac acgctccgga ccccgggtcg atgacgagga aaccacttta ctttcttcct   420
```

```
aggccatcgc ctagaccatc gcgaggacta cacgtcctaa cgggtcttac gtgcgatgtc      480
cttttgggta agaagagggt cggcccacgg ggttatgaag tcacgtaccc gacgacgaag      540
agatctcgta tagggtgagg tgattccagg ttcttctgct acaaccaggt tttcttgcag      600
tggagtctca ggtgaacgac acatcgattt agtatattgt cccagtgtca ttaccccca      660 aagtttcacc tcttggtgtg ccgcacggtg acgtcatgaa caataatagt gtttagaatt      720
ccatgg                                                                726
```

<210> SEQ ID NO 16
<211> LENGTH: 237
<212> TYPE: PRT
<213> ORGANISM: Rat leukemia virus

<400> SEQUENCE: 16

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Arg Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Thr Val Arg Gly Leu Gly Pro Ser
        115                 120                 125

Tyr Cys Ser Phe Gly Glu Met Lys Glu Gly Ser Gly Ser Gly Ser Gly
    130                 135                 140

Ser Ala Pro Asp Val Gln Asp Cys Pro Glu Cys Thr Leu Gln Glu Asn
145                 150                 155                 160

Pro Phe Phe Ser Gln Pro Gly Ala Pro Ile Leu Gln Cys Met Gly Cys
                165                 170                 175

Cys Phe Ser Arg Ala Tyr Pro Thr Pro Leu Arg Ser Lys Lys Thr Met
            180                 185                 190

Leu Val Gln Lys Asn Val Thr Ser Glu Ser Thr Cys Cys Val Ala Lys
        195                 200                 205

Ser Tyr Asn Arg Val Thr Val Met Gly Gly Phe Lys Val Glu Asn His
    210                 215                 220

Thr Ala Cys His Cys Ser Thr Cys Tyr Tyr His Lys Ser
225                 230                 235
```

<210> SEQ ID NO 17
<211> LENGTH: 752
<212> TYPE: DNA
<213> ORGANISM: Rat leukemia virus

<400> SEQUENCE: 17

```
atgaaatcga cggaatcaga ctcgagccaa ggatggagat gttccagggg ctgctgctgt      60
tgctgctgct gagcatgggc gggacatggg catccaagga gccgcttcgg ccacggtgcc     120
gccccatcaa tgccaccctg ctgtggagag aggagggctg ccccgtgtgc atcaccgtca     180
```

```
acaccaccat ctgtgccggc tactgcccca ccatgacccg cgtgctgcag ggggtcctgc      240
cggccctgcc tcaggtggtg tgcaactacc gcgatgtgcg cttcgagtcc atccggctcc      300
ctggctgccc gcgcggcgtg aaccccgtgg tctcctacgc cgtggctctc agctgtcaat      360
gtgcactctg ccgccgcagc accactgact gcactgtgcg aggcctgggg cccagctact      420
gctcctttgg tgaaatgaaa gaaggatccg gtagcggatc tggtagcgct cctgatgtgc      480
aggattgccc agaatgcacg ctacaggaaa acccattctt ctcccagccg ggtgccccaa      540
tacttcagtg catgggctgc tgcttctcta gagcatatcc cactccacta aggtccaaga      600
agacgatgtt ggtccaaaag aacgtcacct cagagtccac ttgctgtgta gctaaatcat      660
ataacagggt cacagtaatg gggggtttca agtggagaa ccacacggcg tgccactgca      720
gtacttgtta ttatcacaaa tcttaaggta cc                                    752

<210> SEQ ID NO 18
<211> LENGTH: 726
<212> TYPE: DNA
<213> ORGANISM: Rat leukemia virus

<400> SEQUENCE: 18
ggttcctacc tctacaaggt ccccgacgac gacaacgacg acgactcgta cccgccctgt       60
acccgtaggt tcctcggcga agccggtgcc acggcgggt agttacggtg ggaccgacac       120
ctcttcctcc cgacggggca cacgtagtgg cagttgtggt ggtagacacg gccgatgacg      180
gggtggatct gggcgcacga cgtccccag gacggccggg acggagtcca ccacacgttg       240
atggcgctac acgcgaagct caggtaggcc gagggaccga cgggcgcgcc gcacttgggg      300
caccagagga tgcggcaccg acagtcgaca gttacacgtg agacggcggc gtcgtggtga      360
ctgacgtgac acgctccgga ccccgggtcg atgacgagga aaccactta ctttcttcct      420 aggccatcgc ctagaccatc gcgaggacta cacgtcctaa cgggtcttac gtgcgatgtc      480
cttttgggta agaagagggt cggcccacgg ggttatgaag tcacgtaccc gacgacgaag      540
agatctcgta tagggtgagg tgattccagg ttcttctgct acaaccaggt tttcttgcag      600
tggagtctca ggtgaacgac acatcgattt agtatattgt cccagtgtca ttaccccca      660 aagtttcacc tcttggtgtg ccgcacggtg acgtcatgaa caataatagt gtttagaatt      720
ccatgg                                                                 726

<210> SEQ ID NO 19
<211> LENGTH: 234
<212> TYPE: PRT
<213> ORGANISM: Rat leukemia virus

<400> SEQUENCE: 19

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Arg Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95
```

```
Asn Pro Val Val Ser Tyr Ala Val Ala Leu Ser Cys Gln Cys Ala Leu
             100                 105                 110
Cys Arg Arg Ser Thr Thr Asp Cys Thr Val Arg Gly Leu Gly Pro Ser
        115                 120                 125
Tyr Cys Ser Phe Gly Glu Gly Ser Gly Ser Gly Ser Gly Ser Ala Pro
    130                 135                 140
Asp Val Gln Asp Cys Pro Glu Cys Thr Leu Gln Glu Asn Pro Phe Phe
145                 150                 155                 160
Ser Gln Pro Gly Ala Pro Ile Leu Gln Cys Met Gly Cys Cys Phe Ser
                165                 170                 175
Arg Ala Tyr Pro Thr Pro Leu Arg Ser Lys Lys Thr Met Leu Val Gln
            180                 185                 190
Lys Asn Val Thr Ser Glu Ser Thr Cys Cys Val Ala Lys Ser Tyr Asn
        195                 200                 205
Arg Val Thr Val Met Gly Gly Phe Lys Val Glu Asn His Thr Ala Cys
    210                 215                 220
His Cys Ser Thr Cys Tyr Tyr His Lys Ser
225                 230
```

<210> SEQ ID NO 20
<211> LENGTH: 743
<212> TYPE: DNA
<213> ORGANISM: Rat leukemia virus

<400> SEQUENCE: 20

| | | |
|---|---|---|
| atgaaatcga cggaatcaga ctcgagccaa ggatggagat gttccagggg ctgctgctgt | 60 |
| tgctgctgct gagcatgggc gggacatggg catccaagga gccgcttcgg ccacggtgcc | 120 |
| gccccatcaa tgccaccctg ctgtggagaa ggagggctg ccccgtgtgc atcaccgtca | 180 |
| acaccaccat ctgtgccggc tactgcccca ccatgacccg cgtgctgcag ggggtcctgc | 240 |
| cggccctgcc tcaggtggtg tgcaactacc gcgatgtgcg cttcgagtcc atccggctcc | 300 |
| ctggctgccc gcgcggcgtg aaccccgtgg tctcctacgc cgtggctctc agctgtcaat | 360 |
| gtgcactctg ccgccgcagc accactgact gcactgtgcg aggcctgggg cccagctact | 420 |
| gctcctttgg tgaaggatcc ggtagcggat ctggtagcgc tcctgatgtg caggattgcc | 480 |
| cagaatgcac gctacaggaa aacccattct ctcccagcg gggtgcccca atacttcagt | 540 |
| gcatgggctg ctgcttctct agagcatatc ccactccact aaggtccaag aagacgatgt | 600 |
| tggtccaaaa gaacgtcacc tcagagtcca cttgctgtgt agctaaatca tataacaggg | 660 |
| tcacagtaat gggggggtttc aaagtggaga accacacggc gtgccactgc agtacttgtt | 720 |
| attatcacaa atcttaaggt acc | 743 |

<210> SEQ ID NO 21
<211> LENGTH: 717
<212> TYPE: DNA
<213> ORGANISM: Rat leukemia virus

<400> SEQUENCE: 21

| | | |
|---|---|---|
| ggttcctacc tctacaaggt ccccgacgac gacaacgacg acgactcgta cccgccctgt | 60 |
| acccgtaggt tcctcggcga agccggtgcc acggcgggt agttacgtg ggaccgacac | 120 |
| ctcttcctcc cgacggggca cacgtagtgg cagttgtggt ggtagacacg gccgatgacg | 180 |
| gggtggatct gggcgcacga cgtccccag gacggccggg acgagtcca ccacacgttg | 240 |
| atggcgctac acgcgaagct caggtaggcc gagggaccga cgggcgcgcc gcacttgggg | 300 |

```
caccagagga tgcggcaccg acagtcgaca gttacacgtg agacggcggc gtcgtggtga      360
ctgacgtgac acgctccgga ccccgggtcg atgacgagga aaccacttcc taggccatcg      420
cctagaccat cgcgaggact acacgtccta acgggtctta cgtgcgatgt cctttgggt       480 aagaagaggg tcggcccacg gggttatgaa gtcacgtacc cgacgacgaa gagatctcgt      540 ataggtgag gtgattccag gttcttctgc tacaaccagg ttttcttgca gtggagtctc       600
aggtgaacga cacatcgatt tagtatattg tcccagtgtc attacccccc aaagtttcac      660
ctcttggtgt gccgcacggt gacgtcatga acaataatag tgtttagaat tccatgg         717
```

<210> SEQ ID NO 22
<211> LENGTH: 234
<212> TYPE: PRT
<213> ORGANISM: Rat leukemia virus

<400> SEQUENCE: 22

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Arg Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Thr Val Arg Gly Leu Gly Pro Ser
        115                 120                 125

Tyr Cys Asp Asp Pro Arg Gly Ser Gly Ser Gly Ser Ala Pro
    130                 135                 140

Asp Val Gln Asp Cys Pro Glu Cys Thr Leu Gln Glu Asn Pro Phe Phe
145                 150                 155                 160

Ser Gln Pro Gly Ala Pro Ile Leu Gln Cys Met Gly Cys Cys Phe Ser
                165                 170                 175

Arg Ala Tyr Pro Thr Pro Leu Arg Ser Lys Lys Thr Met Leu Val Gln
            180                 185                 190

Lys Asn Val Thr Ser Glu Ser Thr Cys Cys Val Ala Lys Ser Tyr Asn
        195                 200                 205

Arg Val Thr Val Met Gly Gly Phe Lys Val Glu Asn His Thr Ala Cys
    210                 215                 220

His Cys Ser Thr Cys Tyr Tyr His Lys Ser
225                 230
```

<210> SEQ ID NO 23
<211> LENGTH: 743
<212> TYPE: DNA
<213> ORGANISM: Rat leukemia virus

<400> SEQUENCE: 23

```
atgaaatcga cggaatcaga ctcgagccaa ggatggagat gttccagggg ctgctgctgt      60
tgctgctgct gagcatgggc gggacatggg catccaagga gccgcttcgg ccacggtgcc     120
```

-continued

```
gccccatcaa tgccaccctg gctgtggaga aggagggctg ccccgtgtgc atcaccgtca     180
acaccaccat ctgtgccggc tactgcccca ccatgacccg cgtgctgcag ggggtcctgc     240
cggccctgcc tcaggtggtg tgcaactacc gcgatgtgcg cttcgagtcc atccggctcc     300
ctggctgccc gcgcggcgtg aaccccgtgg tctcctacgc cgtggctctc agctgtcaat     360
gtgcactctg ccgccgcagc accactgact gcactgtgcg aggcctgggg ccagctact      420 gcgatgaccc gcggggatcc ggtagcggat ctggtagcgc tcctgatgtg caggattgcc     480
cagaatgcac gctacaggaa aacccattct ctcccagcc gggtgcccca atacttcagt      540
gcatgggctg ctgcttctct agagcatatc ccactccact aaggtccaag aagacgatgt     600
tggtccaaaa gaacgtcacc tcagagtcca cttgctgtgt agctaaatca tataacaggg     660
tcacagtaat gggggttttc aaagtggaga accacacggc gtgccactgc agtacttgtt     720
attatcacaa atcttaaggt acc                                              743
```

<210> SEQ ID NO 24
<211> LENGTH: 717
<212> TYPE: DNA
<213> ORGANISM: Rat leukemia virus

<400> SEQUENCE: 24

```
ggttcctacc tctacaaggt ccccgacgac gacaacgacg acgactcgta cccgccctgt      60
acccgtaggt tcctcggcga agccggtgcc acggcggggt agttacggtg ggaccgacac     120
ctcttcctcc cgacggggca cacgtagtgg cagttgtggt ggtagacacg gccgatgacg     180
gggtggatct gggcgcacga cgtcccccag gacggccggg acggagtcca ccacacgttg     240
atggcgctac acgcgaagct caggtaggcc gagggaccga cgggcgcgcc gcacttgggg     300
caccagagga tgcggcaccg acagtcgaca gttacgcgtg agacggcggc gtcgtggtga     360
ctgacgtgac acgctccgga ccccgggtcg atgacgctac tgggcgcccc taggccatcg     420
cctagaccat cgcgaggact acacgtccta acgggtctta cgtgcgatgt cctttgggt      480 aagaagaggg tcgccccacg gggttatgaa gtcacgtacc cgacgacgaa gagatctcgt     540 ataggtgag gtgattccag gttcttctgc tacaaccagg ttttcttgca gtggagtctc      600
aggtgaacga cacatcgatt tagtatattg tcccagtgtc attacccccc aaagtttcac     660
ctcttggtgt gccgcacggt gacgtcatga acaataatag tgtttagaat tccatgg        717
```

<210> SEQ ID NO 25
<211> LENGTH: 226
<212> TYPE: PRT
<213> ORGANISM: Rat leukemia virus

<400> SEQUENCE: 25

```
Met Lys Thr Leu Gln Phe Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
```

-continued

```
            85                  90                  95
Ala Thr Gln Cys His Cys Gly Lys Cys Asp Ser Asp Ser Thr Asp Cys
        100                 105                 110

Thr Val Arg Gly Leu Gly Pro Ser Tyr Cys Ser Phe Gly Glu Gly Ser
        115                 120                 125

Gly Ser Gly Ser Gly Ser Ala Pro Asp Val Gln Asp Cys Pro Glu Cys
        130                 135                 140

Thr Leu Gln Glu Asn Pro Phe Phe Ser Gln Pro Gly Ala Pro Ile Leu
145                 150                 155                 160

Gln Cys Met Gly Cys Cys Phe Ser Arg Ala Tyr Pro Thr Pro Leu Arg
                165                 170                 175

Ser Lys Lys Thr Met Leu Val Gln Lys Asn Val Thr Ser Glu Ser Thr
            180                 185                 190

Cys Cys Val Ala Lys Ser Tyr Asn Arg Val Thr Val Met Gly Gly Phe
        195                 200                 205

Lys Val Glu Asn His Thr Ala Cys His Cys Ser Thr Cys Tyr Tyr His
    210                 215                 220

Lys Ser
225

<210> SEQ ID NO 26
<211> LENGTH: 719
<212> TYPE: DNA
<213> ORGANISM: Rat leukemia virus

<400> SEQUENCE: 26
atgaaatcga cggaatcaga ctcgagccaa ggatgaagac actccagttt ttcttccttt     60
tctgttgctg gaaagcaatc tgctgcaata gctgtgagct gaccaacatc accattgcaa   120
tagagaaaga agaatgtcgt ttctgcataa gcatcaacac cacttggtgt gctggctact   180
gctacaccag ggatctggtg tataaggacc cagccaggcc caaaatccag aaaacatgta   240
ccttcaagga actggtatat gaaacagtga gagtgcccgg ctgtgctcac catgcagatt   300
ccttgtatac atacccagtg gccacccagt gtcactgtgg caagtgtgac agcgacagca   360
ctgattgtac tgtgcgaggc ctggggccca gctactgctc ctttggtgaa ggatccggta   420
gcggatctgg tagcgctcct gatgtgcagg attgcccaga atgcacgcta caggaaaacc   480
cattcttctc ccagccgggt gccccaatac ttcagtgcat gggctgctgc ttctctagag   540
catatcccac tccactaagg tccaagaaga cgatgttggt ccaaaagaac gtcacctcag   600
agtccacttg ctgtgtagct aaatcatata acagggtcac agtaatgggg ggtttcaaag   660
tggagaacca cacggcgtgc cactgcagta cttgttatta tcacaaatct aaggtacc     719

<210> SEQ ID NO 27
<211> LENGTH: 693
<212> TYPE: DNA
<213> ORGANISM: Rat leukemia virus

<400> SEQUENCE: 27
ggttcctact tctgtgaggt caaaaagaag gaaaagacaa cgacctttcg ttagacgacg     60
ttatcgacac tcgactggtt gtagtggtaa cgttatctct tcttcttac agcaaagacg    120 taggcgtagt tgtggtgaac cacacgaccg atgacgatgt ggtccctaga ccacatattc    180
ctgggtcggt ccgggtttta ggtcttttgt acatggaagt tccttgacca tatactttgt    240
cactctcacg ggccgacacg agtggtacgt ctaaggaaca tatgtatggg tcaccggtgg    300
```

-continued

```
gtcacagtga caccgttcac actgtcgctg tcgtgactaa catgacacgc tccggacccc    360
gggtcgatga cgaggaaacc acttcctagg ccatcgccta gaccatcgcg aggactacac    420
gtcctaacgg tcttacgtg cgatgtcctt tgggtaaga agagggtcgg cccacgggt       480 tatgaagtca cgtacccgac gacgaagaga tctcgtatag ggtgaggtga ttccaggttc    540
ttctgctaca accaggtttt cttgcagtgg agtctcaggt gaacgacaca tcgatttagt    600
atattgtccc agtgtcatta cccccaaag tttcacctct tggtgtgccg cacggtgacg     660
tcatgaacaa taatagtgtt tagaattcca tgg                                 693
```

```
<210> SEQ ID NO 28
<211> LENGTH: 222
<212> TYPE: PRT
<213> ORGANISM: Rat leukemia virus

<400> SEQUENCE: 28

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
                35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Gly Ser Gly Ser Gly Ser
                115                 120                 125

Gly Ser Ala Pro Asp Val Gln Asp Cys Pro Glu Cys Thr Leu Gln Glu
    130                 135                 140

Asn Pro Phe Phe Ser Gln Pro Gly Ala Pro Ile Leu Gln Cys Met Gly
145                 150                 155                 160

Cys Cys Phe Ser Arg Ala Tyr Pro Thr Pro Leu Arg Ser Lys Lys Thr
                165                 170                 175

Met Leu Val Gln Lys Asn Val Thr Ser Glu Ser Thr Cys Cys Val Ala
                180                 185                 190

Lys Ser Tyr Asn Arg Val Thr Val Met Gly Gly Phe Lys Val Glu Asn
                195                 200                 205

His Thr Ala Cys His Cys Ser Thr Cys Tyr Tyr His Lys Ser
    210                 215                 220
```

```
<210> SEQ ID NO 29
<211> LENGTH: 707
<212> TYPE: DNA
<213> ORGANISM: Rat leukemia virus

<400> SEQUENCE: 29
atgaaatcga cggaatcaga ctcgagccaa ggatgaagac actccagttt ttcttccttt     60
tctgttgctg gaaagcaatc tgctgcaata gctgtgagct gaccaacatc accattgcaa    120
tagagaaaga agaatgtcgt ttctgcataa gcatcaacac cacttggtgt gctggctact    180
gctacaccag ggatctggtg tataaggacc cagccaggcc caaaatccag aaaacatgta    240
```

-continued

```
ccttcaagga actggtatat gaaacagtga gagtgcccgg ctgtgctcac catgcagatt      300
ccttgtatac ataccccagtg gccacccagt gtcactgtgg caagtgtgac agcgacagca    360
ctgattgtac tgtgcgaggc ctggggccca gctactgcgg atccggtagc ggatctggta    420
gcgctcctga tgtgcaggat tgcccagaat gcacgctaca ggaaaaccca ttcttctccc    480
agccgggtgc cccaatactt cagtgcatgg gctgctgctt ctctagagca tatcccactc    540
cactaaggtc caagaagacg atgttggtcc aaaagaacgt cacctcagag tccacttgct    600
gtgtagctaa atcatataac agggtcacag taatgggggg tttcaaagtg gagaaccaca    660
cggcgtgcca ctgcagtact tgttattatc acaaatctta aggtacc                   707
```

<210> SEQ ID NO 30
<211> LENGTH: 680
<212> TYPE: DNA
<213> ORGANISM: Rat leukemia virus

<400> SEQUENCE: 30

```
ggttcctact tctgtgaggt caaaaagaag gaaaagacaa cgacctttcg ttagacgacg      60
ttatcgacac tcgactggtt gtagtggtaa cgttatctct ttcttcttac agcaaagacg    120
taggcgtagt tgtggtgaac cacacgaccg atgacgatgt ggtccctaga ccacatattc    180
ctgggtcggt ccgggtttta ggtcttttgt acatggaagt tccttgacca tatactttgt    240
cactctcacg ggccgacacg agtggtacgc taaggaaca tatgtatggg tcaccggtgg    300
gtcacagtga caccgttcac actgtcgctg tcgtgactaa catgacacgc tccggacccc    360
gggtcgatga cgcctaggcc atcgcctaga ccatcgcgag gactacacgt cctaacgggt    420
cttacgtgcg atgtcctttt gggtaagaag agggtcggcc cacggggtta tgaagtcacg    480
tacccgacga cgaagagatc tcgtataggg tgaggtgatt ccaggttctt ctgctacaac    540
caggttttct tgcagtggag tctcaggtga acgacacatc gatttagtat attgtcccag    600
tgtcattacc ccccaaagtt tcacctcttg gtgtgcgcac ggtgacgtca tgaacaataa    660
tagtgtttag aattccatgg                                                  680
```

<210> SEQ ID NO 31
<211> LENGTH: 101
<212> TYPE: PRT
<213> ORGANISM: Rat leukemia virus

<400> SEQUENCE: 31

```
Cys Gly Ser Gly Ser Gly Ser Gly Ser Ala Pro Asp Val Gln Asp Cys
 1               5                  10                  15

Pro Glu Cys Thr Leu Gln Glu Asn Pro Phe Phe Ser Gln Pro Gly Ala
                20                  25                  30

Pro Ile Leu Gln Cys Met Gly Cys Cys Phe Ser Arg Ala Tyr Pro Thr
            35                  40                  45

Pro Leu Arg Ser Lys Lys Thr Met Leu Val Gln Lys Gln Val Thr Ser
        50                  55                  60

Glu Ser Thr Cys Cys Val Ala Lys Ser Tyr Asn Arg Val Thr Val Met
65                  70                  75                  80

Gly Gly Phe Lys Val Glu Gln His Thr Ala Cys His Cys Ser Thr Cys
                85                  90                  95

Tyr Tyr His Lys Ser
            100
```

<210> SEQ ID NO 32
<211> LENGTH: 312
<212> TYPE: DNA
<213> ORGANISM: Rat leukemia virus

<400> SEQUENCE: 32

```
tgcggatccg gtagcggatc tggtagcgct cctgatgtgc aggattgccc agaatgcacg      60
ctacaggaaa acccattctt ctcccagccg ggtgccccaa tacttcagtg catgggctgc     120
tgcttctcta gagcatatcc cactccacta aggtccaaga agacgatgtt ggtccaaaag     180
caagtcacct cagagtccac ttgctgtgta gctaaatcat ataacagggt cacagtaatg     240
ggggtttca aagtggagca acacacggcg tgccactgca gtacttgtta ttatcacaaa     300
tcttaaggta cc                                                        312
```

<210> SEQ ID NO 33
<211> LENGTH: 317
<212> TYPE: DNA
<213> ORGANISM: Rat leukemia virus

<400> SEQUENCE: 33

```
acgcctaggc catcgcctag accatcgcga ggactacacg tcctaacggg tcttacgtgc      60
gatgtccttt tgggtaagaa gagggtcggc ccacggggtt atgaagtcac gtacccgacg     120
acgaagagat ctcgtatagg gtgaggtgat tccaggttct tctgctacaa ccaggttttc     180
gtgcagtgga gtctcaggtg aacgacacat cgatttagta tattgtccca gtgtcattac     240
cccccaaagt ttcacctcgt tgtgtgccgc acggtgacgt catgaacaat aatagtgttt     300
agaattccat ggccatg                                                   317
```

<210> SEQ ID NO 34
<211> LENGTH: 181
<212> TYPE: PRT
<213> ORGANISM: Rat leukemia virus

<400> SEQUENCE: 34

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Gln Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Arg Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Gly Ser Ala Pro Asp
                165                 170                 175
```

Val Gln Asp Cys Pro
            180

<210> SEQ ID NO 35
<211> LENGTH: 575
<212> TYPE: DNA
<213> ORGANISM: Rat leukemia virus

<400> SEQUENCE: 35

| | | | | | |
|---|---|---|---|---|---|
| atgaaatcga | cggaatcaga | ctcgagccaa | ggatggagat | gttccagggg ctgctgctgt | 60 |
| tgctgctgct | gagcatgggc | gggacatggg | catccaagga | gccgcttcgg ccacggtgcc | 120 |
| gccccatcca | agccaccctg | gctgtggaga | aggagggctg | ccccgtgtgc atcaccgtca | 180 |
| acaccaccat | ctgtgccggc | tactgcccca | ccatgacccg | cgtgctgcag ggggtcctgc | 240 |
| cggccctgcc | tcaggtggtg | tgcaactacc | gcgatgtgcg | cttcgagtcc atccggctcc | 300 |
| ctggctgccc | gcgcggcgtg | aaccccgtgg | tctcctacgc | cgtggctctc agctgtcaat | 360 |
| gtgcactctg | ccgccgcagc | accactgact | gcggggtcc | caaggaccac cccttgacct | 420 |
| gtgatgaccc | ccgcttccag | ctgaggagaa | ggagtttccg | ggagggggg tcggaaggtt | 480 |
| cgggtagggc | tgagggcccc | gggagcctgt | ggggctagga | gggggttcct aggccatcgc | 540 |
| ctagaccatc | ggctcctgat | gtgcaggatt | gccca | | 575 |

<210> SEQ ID NO 36
<211> LENGTH: 549
<212> TYPE: DNA
<213> ORGANISM: Rat leukemia virus

<400> SEQUENCE: 36

| | | | | | |
|---|---|---|---|---|---|
| ggttcctacc | tctacaaggt | ccccgacgac | gacaacgacg | acgactcgta cccgccctgt | 60 |
| acccgtaggt | tcctcggcga | agccggtgcc | acggcggggt | aggttcggtg ggaccgacac | 120 |
| ctcttcctcc | cgacggggca | cacgtagtgg | cagttgtggt | ggtagacacg gccgatgacg | 180 |
| gggtggatct | gggcgcacga | cgtcccccag | gacggccggg | acggagtcca ccacacgttg | 240 |
| atggcgctac | acgcgaagct | caggtaggcc | gagggaccga | cgggcgcgcc gcacttgggg | 300 |
| caccagagga | tgcggcaccg | acagtcgaca | gttacacgtg | agacggcggc gtcgtggtga | 360 |
| ctgacgcccc | cagggttcct | ggtggggaac | tggacactac | tgggggcgaa ggtcctgagg | 420 |
| agaaggagtt | ccggggagg | ggggtcggaa | ggttcgggta | gggctgaggg ccccgggagc | 480 |
| ctgtggggct | aggagggggt | tcctaggcca | tcgcctagac | catcgcgagg actacacgtc | 540 |
| ctaacgggt | | | | | 549 |

<210> SEQ ID NO 37
<211> LENGTH: 265
<212> TYPE: PRT
<213> ORGANISM: Rat leukemia virus

<400> SEQUENCE: 37

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

```
Leu Gln Gly Val Leu Arg Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Ala Pro Asp
                165                 170                 175

Val Gln Asp Cys Pro Glu Cys Thr Leu Gln Glu Asn Pro Phe Phe Ser
            180                 185                 190

Gln Pro Gly Ala Pro Ile Leu Gln Cys Met Gly Cys Cys Phe Ser Arg
        195                 200                 205

Ala Tyr Pro Thr Pro Leu Arg Ser Lys Lys Thr Met Leu Val Gln Lys
    210                 215                 220

Gln Val Thr Ser Glu Ser Thr Cys Cys Val Ala Lys Ser Tyr Asn Arg
225                 230                 235                 240

Val Thr Val Met Gly Gly Phe Lys Val Glu Gln His Thr Ala Cys His
                245                 250                 255

Cys Ser Thr Cys Tyr Tyr His Lys Ser
            260                 265

<210> SEQ ID NO 38
<211> LENGTH: 836
<212> TYPE: DNA
<213> ORGANISM: Rat leukemia virus

<400> SEQUENCE: 38
atgaaatcga cggaatcaga ctcgagccaa ggatggagat gttccagggg ctgctgctgt      60
tgctgctgct gagcatgggc gggacatggg catccaagga ccgcttcgg ccacggtgcc     120 gccccatcaa tgccaccctg ctgtggaga aggagggctg cccgtgtgc atcaccgtca      180 acaccaccat ctgtgccggc tactgcccca ccatgacccg cgtgctgcag ggggtcctgc      240
cggccctgcc tcaggtggtg tgcaactacc gcgatgtgcg cttcgagtcc atccggctcc      300
ctggctgccc gcgcggcgtg aaccccgtgg tctcctacgc cgtggctctc agctgtcaat      360
gtgcactctg ccgccgcagc accactgact gcggggtcc caaggaccac cccttgacct      420
gtgatgaccc ccgcttccag gactcctctt cctcaaaggc ccctccccc agccttccaa      480 gcccatcccg actcccgggg ccctcggaca ccccgatcct cccccaagga tccggtagcg      540
gatctggtag cgctcctgat gtgcaggatt gcccagaatg cacgctacag gaaaacccat      600
tcttctccca gccgggtgcc ccaatacttc agtgcatggg ctgctgcttc tctagagcat      660
atcccactcc actaaggtcc aagaagacga tgttggtcca aaagcaagtc acctcagagt      720
ccacttgctg tgtagctaaa tcatataaca gggtcacagt aatgggggt ttcaaagtgg      780 agcaacacac ggcgtgccac tgcagtactt gttattatca caaatcttaa ggtacc          836

<210> SEQ ID NO 39
<211> LENGTH: 834
```

<212> TYPE: DNA
<213> ORGANISM: Rat leukemia virus

<400> SEQUENCE: 39

```
ggttcctacc tctacaaggt ccccgacgac gacaacgacg acgactcgta cccgccctgt      60
acccgtaggt tcctcggcga agccggtgcc acggcggggt agttacggtg ggaccgacac     120
ctcttcctcc cgacggggca cacgtagtgg cagttgtggt ggtagacacg gccgatgacg     180
gggtggatct gggcgcacga cgtcccccag gacggccggg acggagtcca ccacacgttg     240
atggcgctac acgcgaagct caggtaggcc gagggaccga cgggcgcgcc gcacttgggg     300
caccagagga tgcggcaccg acagtcgaca gttacacgtg agacggcggc gtcgtggtga     360
ctgacgcccc cagggttcct ggtggggaac tggacactac tgggggcgaa ggtcctgagg     420
agaaggagtt tccggggagg ggggtcggaa ggttcgggta gggctgaggg ccccgggagc     480
ctgtggggct aggaggggt tcctaggcca tcgcctagac catcgcgagg actacacgtc      540
ctaacgggtc ttacgtgcga tgtccttttg ggtaagaaga gggtcggccc acggggttat     600
gaagtcacgt acccgacgac gaagagatct cgtatagggt gaggtgattc caggttcttc     660
tgctacaacc aggttttcgt tcagtggagt ctcaggtgaa cgacacatcg atttagtata     720
ttgtcccagt gtcattaccc cccaaagttt cacctcgttg tgtgccgcac ggtgacgtca     780
tgaacaataa tagtgtttag aattccatgg cctaggtaga gttcgattag gcct          834
```